US007588915B2

(12) United States Patent
Ryan

(10) Patent No.: US 7,588,915 B2
(45) Date of Patent: Sep. 15, 2009

(54) ISOLATED GENOMIC POLYNUCLEOTIDE FRAGMENTS FROM CHROMOSOME 7

(75) Inventor: James W. Ryan, Augusta, GA (US)

(73) Assignee: Ryogen LLC

( * ) Notice: Subject to any disclaimer, the term of this patent is extended or adjusted under 35 U.S.C. 154(b) by 427 days.

(21) Appl. No.: 10/642,946

(22) Filed: Aug. 18, 2003

(65) Prior Publication Data

US 2005/0100912 A1 May 12, 2005

Related U.S. Application Data

(63) Continuation of application No. 09/957,956, filed on Sep. 21, 2001, now abandoned.

(60) Provisional application No. 60/234,422, filed on Sep. 21, 2000.

(51) Int. Cl.
*C12P 21/06* (2006.01)
*C12Q 1/68* (2006.01)
*C12N 15/63* (2006.01)
*C07H 21/02* (2006.01)
*C07H 21/04* (2006.01)

(52) U.S. Cl. ......................... 435/69.1; 435/6; 435/91.1; 435/455; 536/23.1; 536/23.5

(58) Field of Classification Search ..................... 435/6, 435/91.1, 91.31, 455, 458, 69.1, 320.1; 536/23.1, 536/24.5, 23.5
See application file for complete search history.

(56) References Cited

U.S. PATENT DOCUMENTS 5,624,803 A * 4/1997 Noonberg et al. .............. 435/6
5,972,334 A * 10/1999 Denney, Jr. .............. 424/131.1
6,812,339 B1 * 11/2004 Venter et al. ............. 536/24.31

FOREIGN PATENT DOCUMENTS

WO WO95/20678 8/1995
WO WO00/58467 10/2000

OTHER PUBLICATIONS

J. Biol. Chem., vol. 273, No. 25, pp. 15,654-15,660 (1998).*
Sulston et al., Genome Research, vol. 8, No. 11, pp. 1097-1108 (1998).*
U.S. Appl. No. 60/231,498, filed Sep. 8, 2000 (priority appln. Of Venter, US Patent No. 6,812,339.
Table 1 of U.S. Appl. No. 60/231,498.
Table 2 of U.S. Appl. No. 60/231,498.
Table 3 of U.S. Appl. No. 60/231,498.
Table 4 of U.S. Appl. No. 60/231,468.
Table 5 of U.S. Appl. No. 60/231,498.
Table 6 of U.S. Appl. No. 60/231,498.
Table 7 of U.S. Appl. No. 60/231,498.
Table 8 of U.S. Appl. No. 60/231,498.
Table 9 of U.S. Appl. No. 60/231,498.
Table 10 of U.S. Appl. No. 60/231,498.
Table 11 of U.S. Appl. No. 60/231,498.
Table 12 of U.S. Appl. No. 60/231,498.
Table 13 of U.S. Appl. No. 60/231,498.
Table 14 of U.S. Appl. No. 60/231,498.
Table 15 of U.S. Appl. No. 60/231,498.
Table 16 of U.S. Appl. No. 60/231,498.
Table 17 of U.S. Appl. No. 60/231,498.
Table 18 of U.S. Appl. No. 60/231,498.
Table 19 of U.S. Appl. No. 60/231,498.
Table 20 of U.S. Appl. No. 60/231,498.
Table 21 of U.S. Appl. No. 60/231,498.
Table 22 of U.S. Appl. No. 60/231,498.
Table 23 of U.S. Appl. No. 60/231,498.
Table 24 of U.S. Appl. No. 60/231,498.
Table 25 of U.S. Appl. No. 60/231,498.
Waterston et al., Genbank accession No. gi:4337283, submitted Mar. 2, 1999 accessible at http://www.ncbi.nim.nih.gov/entrez/viewer.fcgi?val=433728.
Nuttall et al., Bone, 2000, 177-184, 27.
Muise et al, Biochem. J., 1999, 341-345, 343.
Ahmed et al., PNAS, 1999, 14795-14800, 96.
Waterston et al., RH PubMed Accession No. AC0006456. Subm. Jan. 28, 1999, bases 1-153201.
Layne et al., J. Biol. Chem., 1998, 15654-15660, 273.
McNew et al., J. Biol. Chem., 1997, 17776-17783, 272.
Altschul et al., Nuc. Acids Res., 1997, 3389-3402, 25.
Burge et al., J. Mol. Biol., 1997, 78-94, 268.
Ohno et al., Biochem. Biophys. Res. Comm., 1996, 411-414, 228.
Zhang et al., Genomics, 1995, 179-186, 29.
Maestrini et al., Hum. Mol. Gen., 1993, 761-766,2.
Skidgel et al., TIPS, 1988, 299-304, 9.
Tanizawa et al., 1992, Mol. Endo. 6:1070.
Database EMBL accession No. Q9UES0, May 1, 2000, SNARE protein Ykt6 (Fragment). *Homo sapiens*.

* cited by examiner

*Primary Examiner*—Jane Zara
(74) *Attorney, Agent, or Firm*—Cheryl H. Agris; The Law Offices of Cheryl H. Agris, PC

(57) ABSTRACT

The invention is directed to isolated genomic polynucleotide fragments that encode human SNARE YKT6, human glucokinase, human adipocyte enhancer binding protein (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

6 Claims, No Drawings

ISOLATED GENOMIC POLYNUCLEOTIDE FRAGMENTS FROM CHROMOSOME 7

PRIORITY CLAIM

This application claims priority under 35 U.S.C. §19(e) to provisional application Ser. No. 60/234,422, filed Sep. 21, 2000 and is a continuation of application Ser. No. 09/957,956, filed Sep. 21, 2001 now abandoned, the contents of which are incorporated herein by reference.

FIELD OF THE INVENTION

The invention is directed to isolated genomic polynucleotide fragments that encode human SNARE YKT6, human glucokinase, human adipocyte enhancer binding protein 1 (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

BACKGROUND OF THE INVENTION

Chromosome 7 contains genes encoding, for example, epidermal growth factor receptor, collagen-1-Alpha-1-chain, SNARE YKT6, human glucokinase, human adipocyte enhancer binding protein 1 and DNA polymerase delta small subunit (POLD2). SNARE YKT6, human glucokinase, human adipocyte enhancer binding protein 1 and DNA polymerase delta small subunit (POLD2) are discussed in further detail below.

SNARE YKT6

SNARE YKT6, a substrate for prenylation, is essential for vesicle-associated endoplasmic reticulum-Golgi transport (McNew, J. A. et al. J. Biol. Chem. 272, 17776-17783, 1997). It has been found that depletion of this function stops cell growth and manifests a transport block at the endoplasmic reticulum level.

Human Glucokinase

Human glucokinase (ATP:D-hexose 6-phosphotransferase) is thought to play a major role in glucose sensing in pancreatic islet beta cells (Tanizawa et al., 1992, Mol. Endocrinol. 6:1070-1081) and in the liver. Glucokinase defects have been observed in patients with noninsulin-dependent diabetes mellitus (NIDDM) patients. Mutations in the human glucokinase gene are thought to play a role in the early onset of NIDDM. The gene has been shown by Southern Blotting to exist as a single copy on chromosome 7. It was further found to contain 10 exons including one exon expressed in islet beta cells and the other expressed in liver.

Human Adipocyte Enhancer Binding Protein 1

The adipocyte-enhancer binding protein 1 (AEBP1) is a transcriptional repressor having carboxypeptidase B-like activity which binds to a regulatory sequence (adipocyte enhancer 1, AE-1) located in the proximal promoter region of the adipose P2 (aP2) gene, which encodes the adipocyte fatty acid binding protein (Muise et al., 1999, Biochem. J. 343: 341-345). B-like carboxypeptidases remove C-terminal arginine and lysine residues and participate in the release of active peptides, such as insulin, alter receptor specificity for polypeptides and terminate polypeptide activity (Skidgel, 1988, Trends Pharmacol. Sci. 9:299-304). For example, they are thought to be involved in the onset of obesity (Naggert et al., 1995, Nat. Genet. 10:1335-1342). It has been reported that obese and hyperglycemic mice homozygous for the fat mutation contain a mutation in the CP-E gene.

Full length cDNA clones encoding AEBP1 have been isolated from human osteoblast and adipose tissue (Ohno et al., 1996, Biochem. Biophys Res. Commun. 228:411-414). Two forms have been found to exist due to alternative splicing. This gene appears to play a significant role in regulating adipogenesis. In addition to playing a role in obesity, adipogenesis may play a role in ostopenic disorders. It has been postulated that adipogenesis inhibitors may be used to treat osteopenic disorders (Nuttal et al., 2000, Bone 27:177-184).

DNA Polymerase Delta Small Subunit (POLD2)

DNA polymerase delta core is a heterodimeric enzyme with a catalytic subunit of 125 kD and a second subunit of 50 kD and is an essential enzyme for DNA replication and DNA repair (Zhang et al., 1995, Genomics 29:179-186). cDNAs encoding the small subunit have been cloned and sequenced. The gene for the small subunit has been localized to human chromosome 7 via PCR analysis of a panel of human-hamster hybrid cell lines. However, the genomic DNA has not been isolated and the exact location on chromosome 7 has not been determined.

OBJECTS OF THE INVENTION

Although cDNAs encoding the above-disclosed proteins have been isolated, their location on chromosome 7 has not been determined. Furthermore, genomic DNA encoding these polypeptides have not been isolated. Noncoding sequences can play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to an isolated genomic polynucleotide, said polynucleotide obtainable from human chromosome 7 having a nucleotide sequence at least 95% identical to a sequence selected from the group consisting of:

(a) a polynucleotide encoding a polypeptide selected from the group consisting of human SNARE YKT6 depicted in SEQ ID NO:1, human glucokinase depicted in SEQ ID NO:2, human adipocyte enhancer binding protein 1 (AEBP1) depicted in SEQ ID NO:3 and DNA directed 50 kD regulatory subunit (POLD2) depicted in SEQ ID NO:4;

(b) a polynucleotide selected from the group consisting of SEQ ID NO:5 which encodes human SNARE YKT6 depicted in SEQ ID NO:1, SEQ ID NO:6 which encodes human glucokinase depicted in SEQ ID NO:2, SEQ ID NO:8 which encodes human adipocyte enhancer binding protein 1 depicted in SEQ ID NO:3 and SEQ ID NO:7 which encodes DNA directed 50 kD regulatory subunit (POLD2) depicted in SEQ ID NO:4;

(c) a polynucleotide which is a variant of SEQ ID NOS:5, 6, 7, or 8;

(d) a polynucleotide which is an allelic variant of SEQ ID NOS:5, 6, 7, or 8;

(e) a polynucleotide which encodes a variant of SEQ ID NOS:1, 2, 3, or 4;

(f) a polynucleotide which hybridizes to any one of the polynucleotides specified in (a)-(e);

(g) a polynucleotide that is a reverse complement to the polynucleotides specified in (a)-(f) and (h) containing at least 10 transcription factor binding sites selected from the group consisting of AP1FJ-Q2, AP1-C, AP1-Q2, AP1-Q4, AP4-Q5, AP4-Q6, ARNT-01, CEBP-01, CETS1P54-01, CREL-01, DELTAEF1-01, FREAC7-01, GATA1-02, GATA1-03, GATA1-04, GATA1-06, GATA2-02, GATA3-02, GATA-C, GC-01, GFII-01, HFH2-01, HFH3-01, HFH8-01, IK2-01, LMO2COM-01, LMO2COM-02, LYF1-01, MAX-01, NKX25-01, NMYC-01, S8-01, SOX5-01, SP1-Q6, SAEBP1-01, SRV-02, STAT-01, TATA-01, TCF11-01, USF-01, USF-C and USF-Q6 as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

DETAILED DESCRIPTION OF THE INVENTION

The invention is directed to isolated genomic polynucleotide fragments that encode human SNARE YKT6, human glucokinase, human adipocyte enhancer binding protein 1 and DNA directed 50 kD regulatory subunit (POLD2), which in a specific embodiment are the SNARE YKT6, human glucokinase, human adipocyte enhancer binding protein 1 and DNA directed 50 kD regulatory subunit (POLD2) genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or could be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The human SNARE YKT6 polypeptide has the amino acid sequence depicted in SEQ ID NO:1 and is encoded by the genomic DNA sequence shown in SEQ ID NO:5.

The genomic DNA for SNARE YKT6 gene is 39,000 base pairs in length and contains seven exons (see Table 4 below for location of exons). As will be discussed in further detail below, the SNARE YKT6 gene is situated in genomic clone AC006454 at nucleotides 36,001-75,000.

The human glucokinase is depicted in SEQ ID NO:2 and is encoded by the genomic DNA sequence shown in SEQ ID NO:6. The human glucokinase genomic DNA is 46,000 base pairs in length and contains ten exons (see Table 3 below for location of exons).

The human adipocyte enhancer binding protein 1 has the amino acid sequence depicted in SEQ ID NO:3 and is encoded by the genomic DNA sequence shown in SEQ ID NO:8. The adipocyte enhancer binding protein 1 is 16,000 base pairs in length and contains 21 exons (see Table 2 below for location of exons). As will be discussed in further detail below, the human AEBP1 gene is situated in genomic clone AC006454 at nucleotides 137,041-end.

POLD2 has an amino acid sequence depicted in SEQ ID NO:4 and a genomic DNA sequence depicted in SEQ ID NO:7. The POLD2 gene is 19,000 base pairs in length and contains ten exons (see Table 1 below for location of exons). As will be discussed in further detail below, the POLD2 gene is situated in genomic clone AC006454 at nucleotides 119,001-138,000.

The polynucleotides of the invention have at least a 95% identity and may have a 96%, 97%, 98% or 99% identity to the polynucleotides depicted in SEQ ID NOS:5, 6, 7 or 8 as well as the polynucleotides in reverse sense orientation, or the polynucleotide sequences encoding the SNARE YKT6, human glucokinase, AEBP1, or POLD2 polypeptides depicted in SEQ ID NOS:1, 2, 3, or 4 respectively.

A polynucleotide having 95% "identity" to a reference nucleotide sequence of the present invention, is identical to the reference sequence except that the polynucleotide sequence may include on average up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 95 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 5% of the sequence (number of bases at the 5' and 3' ends not matched/total numbers of bases in the query sequence) so 5% is subtracted from the percent identity score calculated by the FASTDB program. If the remaining 95 bases were perfectly matched the final percent identity would be 95%. In another example, a 95 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 5, 6, 7 or 8. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3 or 4 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the SNARE YKT6, AEBP1, human glucokinase and POLD2 genes. These include but are not limited to an intron, a 5' non-coding region, a 3' non-coding region and splice junctions (see Tables 1-4), as well as transcription factor binding sites (see Table 5). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of Polymerase, DNA directed, 50 kD regulatory subunit (POLD2) Genomic DNA

| EXONS | LOCATION (nucleotide no.) | (Amino acid no.) |
|---|---|---|
| 1. | 11546 | 11764 |
| | 1 | 73 |
| 2. | 15534 | 15656 |
| | 74 | 114 |
| 3. | 15857 | 15979 |
| | 115 | 155 |
| 4. | 16351 | 16464 |
| | 156 | 193 |
| 5. | 16582 | 16782 |
| | 194 | 260 |
| 6. | 17089 | 17169 |
| | 261 | 287 |
| 7. | 17327 | 17484 |
| | 288 | 339 |
| 8. | 17704 | 17829 |
| | 340 | 381 |
| 9. | 18199 | 18303 |
| | 382 | 416 |
| 10. | 18653 | 18811 |
| | 417 | 469 |

'tga' at 18812-14
Poly A at 18885-90

TABLE 2

AEBP1 (adipocyte enhancer binding protein 1), vascular smooth muscle-type. Reverse strand coding.

| EXONS | LOCATION (nucleotide no.) | (Amino acid no.) |
|---|---|---|
| 21. | 1301 | 1966 |
| | 1158 | 937 |
| 20. | 2209 | 2304 |
| | 936 | 905 |
| 19. | 2426 | 2569 |
| | 904 | 857 |
| 18. | 2651 | 3001 |
| | 856 | 740 |
| 17. | 3238 | 3417 |
| | 739 | 680 |
| 16. | 3509 | 3706 |
| | 679 | 614 |
| 15. | 3930 | 4052 |
| | 613 | 573 |
| 14. | 4320 | 4406 |
| | 572 | 544 |
| 13. | 4503 | 4646 |
| | 543 | 496 |

TABLE 2-continued

AEBP1 (adipocyte enhancer binding protein 1), vascular smooth muscle-type. Reverse strand coding.

| EXONS | LOCATION (nucleotide no.) | (Amino acid no.) |
|---|---|---|
| 12. | 4750 | 4833 |
| | 495 | 468 |
| 11. | 5212 | 5352 |
| | 467 | 421 |
| 10. | 5435 | 5545 |
| | 420 | 384 |
| 9. | 6219 | 6272 |
| | 383 | 366 |
| 8. | 6376 | 6453 |
| | 365 | 340 |
| 7. | 6584 | 6661 |
| | 339 | 314 |
| 6. | 7476 | 7553 |
| | 313 | 288 |
| 5. | 7629 | 7753 |
| | 287 | 247 |
| 4. | 7860 | 7931 |
| | 246 | 223 |
| 3. | 8050 | 8121 |
| | 222 | 199 |
| 2. | 8673 | 9014 |
| | 198 | 85 |
| 1. | 10642 | 10893 |
| | 84 | 1 |

Stop codon 1298-1300
Poly A-site 1013-18

TABLE 3

Glucokinase

| EXONS | LOCATION (nucleotide no.) | (Amino acid no.) |
|---|---|---|
| 1. | 20485 | 20523 |
| | 1 | 13 |
| 2. | 25133 | 25297 |
| | 14 | 68 |
| 3. | 26173 | 26328 |
| | 69 | 120 |
| 4. | 27524 | 27643 |
| | 121 | 160 |
| 5. | 28535 | 28630 |
| | 161 | 192 |
| 6. | 28740 | 28838 |
| | 193 | 225 |
| 7. | 30765 | 30950 |
| | 226 | 287 |
| 8. | 31982 | 32134 |
| | 288 | 338 |
| 9. | 32867 | 33097 |
| | 339 | 415 |
| 10. | 33314 | 33460 |
| | 416 | 464 |

Stop codon 33461-3

TABLE 4

SNARE YKT6. Reverse strand coding.

| EXONS | LOCATION (nucleotide no.) | (Amino acid no.) |
|---|---|---|
| 7. | 4320 | 4352 |
| | 198 | 188 |
| 6. | 5475 | 5576 |
| | 187 | 154 |
| 5. | 8401 | 8466 |
| | 153 | 132 |
| 4. | 9107 | 9211 |
| | 131 | 97 |
| 3. | 10114 | 10215 |
| | 96 | 63 |
| 2. | 11950 | 12033 |
| | 62 | 35 |
| 1. | 15362 | 15463 |
| | 34 | 1 |

Stop codon at 4817-19
Poly A-site: 4245-4250

TABLE 5

TRANSCRIPTION FACTOR BINDING SITES

| BINDING SITES | SNARE YKT6 | GLUCOKINASE | POLD2 | AEBP1 |
|---|---|---|---|---|
| AP1FJ-Q2 | 11 | | | 11 |
| AP1-C | 15 | 15 | 7 | 6 |
| AP1-Q2 | 9 | | | 5 |
| AP1-Q4 | 7 | | | 4 |
| AP4-Q5 | 36 | | 5 | 43 |
| AP4-Q6 | 17 | | | 23 |
| ARNT-01 | 7 | | | 5 |
| CEBP-01 | 7 | | | |
| CETS1P54-01 | 6 | | | |
| CREL-01 | 7 | | | |
| DELTAEF1-01 | 64 | 12 | 5 | 50 |
| FREAC7-01 | | 4 | | |
| GATA1-02 | 19 | | | |
| GATA1-03 | 12 | | | 6 |
| GATA1-04 | 25 | 6 | | |
| GATA1-06 | 8 | 5 | | |
| GATA2-02 | 10 | | | |
| GATA3-02 | 5 | | | |
| GATA-C | 11 | 6 | | |
| GC-01 | | | | 4 |
| GFII-01 | 6 | | | |
| HFH2-01 | 5 | | | |
| HFH3-01 | 10 | | | |
| HFH8-01 | 4 | | | |
| IK2-01 | 49 | | | 29 |
| LMO2COM-01 | 41 | 6 | | 27 |
| LMO2COM-02 | 31 | 5 | | 7 |
| LYF1-01 | 10 | 13 | 6 | |
| MAX-01 | 4 | | | |
| MYOD-01 | 7 | | | |
| MYOD-Q6 | 32 | 19 | 7 | 12 |
| MZF1-01 | 99 | 40 | 15 | 94 |
| NF1-Q6 | 5 | | | 7 |
| NFAT-Q6 | 43 | 8 | 7 | 8 |
| NFKAPPAB50-01 | | 4 | | |
| NKX25-01 | 13 | 14 | 5 | |
| NMYC-01 | 12 | | | 8 |
| S8-01 | | 30 | 4 | |
| SOX5-01 | 21 | 20 | 4 | 4 |
| SP1-Q6 | | | | 8 |
| SAEBP1-01 | 4 | | | |
| SRV-02 | 5 | | | |
| STAT-01 | 6 | | | |
| TATA-01 | 8 | | | |
| TCF11-01 | 47 | 28 | 5 | 19 |
| USF-01 | 12 | 8 | 6 | 8 |
| USF-C | 16 | 12 | 12 | 8 |
| USF-Q6 | 6 | | | |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

Expression of Polypeptides

Isolated Polynucleotide Sequences

The human chromosome 7 genomic clone of accession number AC006454 has been discovered to contain the SNARE YKT6 gene, the human glucokinase gene, the AEBP1 gene, and the POLD2 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC006454 was compared to the SNARE YKT6 cDNA sequence, accession number NM_006555 (McNew et al., 1997, J. Biol. Chem. 272:17776-177783), the human glucokinase cDNA sequence (Tanizawa et al., 1992, Mol. Endocrinol. 6:1070-1081), accession number NM_000162 (major form) and M69051 (minor form), , AEBP1 cDNA sequence, accession number NM_001129 (accession number D86479 for the osteoblast type) (Layne et al., 1998, J. Biol. Chem. 273:15654-15660) and the POLD2 cDNA sequence, accession number NM_006230 (Zhang et al., 1995, Genomics 29:179-186).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long chain PCR may be used. In a specific embodiment, 5' or 3' non-coding portions of each gene may be identified by methods including but are not limited to, filter probing, clone enrichment using specific probes and protocols similar or identical to 5' and 3' "RACE" protocols which are well known in the art. For instance, a method similar to 5' RACE is available for generating the missing 5' end of a desired full-length transcript. (Fromont-Racine et al., 1993, Nucl. Acids Res. 21:1683-1684).

Once the DNA fragments are generated, identification of the specific DNA fragment containing the desired SNARE YKT6 gene, the human glucokinase gene, the AEBP1 gene, or POLD2 gene may be accomplished in a number of ways. For example, if an amount of a portion of a SNARE YKT6 gene, the human glucokinasegene, the POLD2 gene or AEBP1 gene, or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:5, 6, 7 or 8. Preferably, a fragment is selected that is highly unique to the encoded polypeptides. Those DNA fragments with substantial homology to the probe will hybridize. As noted above, the greater the degree of homology, the more stringent hybridization conditions can be used. In one embodiment, low stringency hybridization conditions are used to identify a homologous SNARE YKT6, the human glucokinase, the AEBP1, or POLD2 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:5, 6, 7 or 8 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the SNARE YKT6, the human glucokinase, the AEBP1, or POLD2 polynucleotide.

A gene encoding SNARE YKT6, the human glucokinase, the AEBP1, or POLD2 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the SNARE YKT6 gene (nucleotides 4320-15463 of SEQ ID NO:5), human glucokinase gene (nucleotides 20485-33460 of SEQ ID NO:6), AEBP1 gene (nucleotides 1301-10893 of SEQ ID NO:8) or POLD2 gene (nucleotides 11546-18811 of SEQ ID NO:7) operably linked to one or more control sequences which direct the expression of the coding sequence in a suitable cell under conditions compatible with the control sequences.

The invention is further directed to a nucleic acid construct comprising expression control sequences derived from SEQ ID NOS: 5, 6, 7 or 8 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl Acad. of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM§1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. ÒYeastÓ as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182-187, Academic Press, Inc., New York; Ito et al., 1983, *Journal of Bacteriology* 153: 163; and Hinnen et al., 1978, *Proc. e Natl Acad. f Sci.s USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, AEBP1 activity can be determined by measuring carboxypeptidase activity as described by Muise and Ro, 1999, Biochem. J. 343:341-345. Here, the conversion of hippuryl-L-arginine, hippuryl-L-lysine or hippuryl-L-phenylalanine to hippuric acid may be monitored spectrophotometrically. POLD2 activity may be detected by assaying for DNA polymerase_activity (see, for example, Ng et al., 1991, J. Biol. Chem. 266:11699-11704).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the SNARE YKT6, human glucokinase, AEBP1 or POLD2 polypeptides produced according to the method of the present invention may be used as an immunogen to generate any of these polypeptides. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the SNARE YKT6, human glucokinase, AEBP1 or POLD2 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the SNARE YKT6, human glucokinase, AEBP1 or POLD2 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the SNARE YKT6, AEBP1, human glucokinase or POLD2 polypeptides.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2, fragment,and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al.,"Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:5, 6, 7 or 8 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis.

Polynucleotides containing noncoding regions may be used as PCR primers and may be used to amplify the genomic DNA isolated from the patients. Additionally, primers may be obtained by routine or long range PCR, that can yield products containing more than one exon and intervening intron. The sequence of the amplified genomic DNA from the patient may be determined using methods known in the art. Such probes may be between 10-100 nucleotides in length and may preferably be between 20-50 nucleotides in length.

Thus the invention is thus directed to kits comprising these polynucleotide probes. In a specific embodiment, these probes are labeled with a detectable substance.

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

The antisense oligonucleotides or mimetics of the present invention may be used to decrease levels of a polypeptide. For example, SNARE YKT6 has been found to be essential for vesicle-associated endoplasmic reticulum-Golgi transport and cell growth. Therefore, the SNARE YKT6 antisense oligonucleotides of the present invention could be used to inhibit cell growth and in particular, to treat or prevent tumor growth. POLD2 is necessary for DNA replication. POLD2 antisense sequences could also be used to inhibit cell growth. Glucokinase and AEBP1 antisense sequences may be used to treat hyperglycemia.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers,dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, SNARE YKT6 is necessary for cell growth, POLD2 is involved in DNA replication and repair, AEBP1 is involved in repressing adipogenesis and glucokinase is involved in glucose sensing in pancreatic islet beta cells and liver. Therefore, the SNARE YKT6 gene may be used to modulate or prevent cell apoptosis and treat such disorders as virus-induced lymphocyte depletion (AIDS); cell death in neurodegenerative disorders characterized by the gradual loss of specific sets of neurons (e.g., Alzheimer's Disease, Parkinson's disease, ALS, retinitis pigmentosa, spinal muscular atrophy and various forms of cerebellar degeneration), cell death in blood cell disorders resulting from deprivation of growth factors (anemia associated with chronic disease, aplastic anemia, chronic neutropenia and myelodysplastic syndromes) and disorders arising out of an acute loss of blood flow (e.g., myocardial infarctions and stroke). The glucokinase gene may be used to treat diabetes mellitus. The AEBP1 gene may be used to modulate or inhibit adipogenesis and treat obesity, diabetes mellitus and/or osteopenic disorders. POLD2 may be used to treat defects in DNA repair such as xeroderma pigmentosum, progeria and ataxia telangiectasia.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.
b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propy1]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci.298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N4-spermine cholesteryl carbamate (GL-67) disclosed in U.S. Pat. No. 5,767,099. Additional preferred lipids include N4—spermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to §2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated genomic nucleic acid molecule, said nucleic acid molecule obtainable from human chromosome 7 consisting of a nucleotide sequence selected from the group consisting of:

(a) a nucleic acid molecule of SEQ ID NO:8 which includes sequence encoding a polypeptide that has human adipocyte enhancer binding protein 1 activity;

(b) a fragment of (a) comprising at least nucleotides 1301-10893 of SEQ ID NO:8 which encodes a polypeptide having human adipocyte enhancer binding protein 1 activity and (c) a nucleic acid molecule which is a complement of the polynucleotides specified in (a)-(b).

2. A nucleic acid construct comprising the nucleic acid molecule of claim 1.

3. An expression vector comprising the nucleic acid molecule of claim 1.

4. A recombinant host cell comprising the nucleic acid molecule of claim 1.

5. A method for obtaining human adipocyte enhancer binding protein 1 comprising:

(a) culturing the recombinant host cell of claim 4 under conditions that provide for the expression of said human adipocyte enhancer binding protein 1 and (b) recovering said expressed human adipocyte enhancer binding protein 1.

6. A composition comprising the nucleic acid molecule of claim 1 and a carrier.

* * * * *

SEQUENCE LISTING

```
<160> NUMBER OF SEQ ID NOS: 8

<210> SEQ ID NO 1
<211> LENGTH: 198
<212> TYPE: PRT
<213> ORGANISM: Homo sapiens

<400> SEQUENCE: 1

Met Lys Leu Tyr Ser Leu Ser Val Leu Tyr Lys Gly Glu Ala Lys Val
1               5                   10                  15

Val Leu Leu Lys Ala Ala Tyr Asp Val Ser Ser Phe Ser Phe Phe Gln
            20                  25                  30

Arg Ser Ser Val Gln Glu Phe Met Thr Phe Thr Ser Gln Leu Ile Val
        35                  40                  45

Glu Arg Ser Ser Lys Gly Thr Arg Ala Ser Val Lys Glu Gln Asp Tyr
    50                  55                  60

Leu Cys His Val Tyr Val Arg Asn Asp Ser Leu Ala Gly Val Val Ile
65                  70                  75                  80

Ala Asp Asn Glu Tyr Pro Ser Arg Val Ala Phe Thr Leu Leu Glu Lys
                85                  90                  95

Val Leu Asp Glu Phe Ser Lys Gln Val Asp Arg Ile Asp Trp Pro Val
            100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
    130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Met
        195


<210> SEQ ID NO 2
<211> LENGTH: 464
<212> TYPE: PRT
<213> ORGANISM: Homo sapiens

<400> SEQUENCE: 2

Met Pro Arg Pro Arg Ser Gln Leu Pro Gln Pro Asn Ser Gln Val Glu
1               5                   10                  15

Gln Ile Leu Ala Glu Phe Gln Leu Gln Glu Glu Asp Leu Lys Lys Val
            20                  25                  30
```

-continued

```
Met Arg Arg Met Gln Lys Glu Met Asp Arg Gly Leu Arg Leu Glu Thr
        35                  40                  45

His Glu Glu Ala Ser Val Lys Met Leu Pro Thr Tyr Val Arg Ser Thr
    50                  55                  60

Pro Glu Gly Ser Glu Val Gly Asp Phe Leu Ser Leu Asp Leu Gly Gly
65                  70                  75                  80

Thr Asn Phe Arg Val Met Leu Val Lys Val Gly Glu Gly Glu Glu Gly
                85                  90                  95

Gln Trp Ser Val Lys Thr Lys His Gln Thr Tyr Ser Ile Pro Glu Asp
            100                 105                 110

Ala Met Thr Gly Thr Ala Glu Met Leu Phe Asp Tyr Ile Ser Glu Cys
        115                 120                 125

Ile Ser Asp Phe Leu Asp Lys His Gln Met Lys His Lys Lys Leu Pro
    130                 135                 140

Leu Gly Phe Thr Phe Ser Phe Pro Val Arg His Glu Asp Ile Asp Lys
145                 150                 155                 160

Gly Ile Leu Leu Asn Trp Thr Lys Gly Phe Lys Ala Ser Gly Ala Glu
                165                 170                 175

Gly Asn Asn Val Val Gly Leu Leu Arg Asp Ala Ile Lys Arg Arg Gly
            180                 185                 190

Asp Phe Glu Met Asp Val Val Ala Met Val Asn Asp Thr Val Ala Thr
        195                 200                 205

Met Ile Ser Cys Tyr Tyr Glu Asp His Gln Cys Glu Val Gly Met Ile
    210                 215                 220

Val Gly Thr Gly Cys Asn Ala Cys Tyr Met Glu Glu Met Gln Asn Val
225                 230                 235                 240

Glu Leu Val Glu Gly Asp Glu Gly Arg Met Cys Val Asn Thr Glu Trp
                245                 250                 255

Gly Ala Phe Gly Asp Ser Gly Glu Leu Asp Glu Phe Leu Leu Glu Tyr
            260                 265                 270

Asp Arg Leu Val Asp Glu Ser Ser Ala Asn Pro Gly Gln Gln Leu Tyr
        275                 280                 285

Glu Lys Leu Ile Gly Gly Lys Tyr Met Gly Glu Leu Val Arg Leu Val
    290                 295                 300

Leu Leu Arg Leu Val Asp Glu Asn Leu Leu Phe His Gly Glu Ala Ser
305                 310                 315                 320

Glu Gln Leu Arg Thr Arg Gly Ala Phe Glu Thr Arg Phe Val Ser Gln
                325                 330                 335

Val Glu Ser Asp Thr Gly Asp Arg Lys Gln Ile Tyr Asn Ile Leu Ser
            340                 345                 350

Thr Leu Gly Leu Arg Pro Ser Thr Thr Asp Cys Asp Ile Val Arg Arg
        355                 360                 365

Ala Cys Glu Ser Val Ser Thr Arg Ala Ala His Met Cys Ser Ala Gly
    370                 375                 380

Leu Ala Gly Val Ile Asn Arg Met Arg Glu Ser Arg Ser Glu Asp Val
385                 390                 395                 400

Met Arg Ile Thr Val Gly Val Asp Gly Ser Val Tyr Lys Leu His Pro
                405                 410                 415

Ser Phe Lys Glu Arg Phe His Ala Ser Val Arg Arg Leu Thr Pro Ser
            420                 425                 430

Cys Glu Ile Thr Phe Ile Glu Ser Glu Glu Gly Ser Gly Arg Gly Ala
        435                 440                 445
```

-continued

```
Ala Leu Val Ser Ala Val Ala Cys Lys Lys Ala Cys Met Leu Gly Gln
    450                 455                 460


<210> SEQ ID NO 3
<211> LENGTH: 1158
<212> TYPE: PRT
<213> ORGANISM: Homo sapiens

<400> SEQUENCE: 3

Met Ala Ala Val Arg Gly Ala Pro Leu Leu Ser Cys Leu Leu Ala Leu
1               5                   10                  15

Leu Ala Leu Cys Pro Gly Gly Arg Pro Gln Thr Val Leu Thr Asp Asp
            20                  25                  30

Glu Ile Glu Glu Phe Leu Glu Gly Phe Leu Ser Glu Leu Glu Pro Glu
        35                  40                  45

Pro Arg Glu Asp Asp Val Glu Ala Pro Pro Pro Pro Glu Pro Thr Pro
    50                  55                  60

Arg Val Arg Lys Ala Gln Ala Gly Gly Lys Pro Gly Lys Arg Pro Gly
65                  70                  75                  80

Thr Ala Ala Glu Val Pro Pro Glu Lys Thr Lys Asp Lys Gly Lys Lys
                85                  90                  95

Gly Lys Lys Asp Lys Gly Pro Lys Val Pro Lys Glu Ser Leu Glu Gly
            100                 105                 110

Ser Pro Arg Pro Pro Lys Lys Gly Lys Glu Lys Pro Pro Lys Ala Thr
        115                 120                 125

Lys Lys Pro Lys Glu Lys Pro Pro Lys Ala Thr Lys Lys Pro Lys Glu
    130                 135                 140

Glu Pro Pro Lys Ala Thr Lys Lys Pro Lys Glu Lys Pro Pro Lys Ala
145                 150                 155                 160

Thr Lys Lys Pro Pro Ser Gly Lys Arg Pro Pro Ile Leu Ala Pro Ser
                165                 170                 175

Glu Thr Leu Glu Trp Pro Leu Pro Pro Pro Pro Ser Pro Gly Pro Glu
            180                 185                 190

Glu Leu Pro Gln Glu Gly Gly Ala Pro Leu Ser Asn Asn Trp Gln Asn
        195                 200                 205

Pro Gly Glu Glu Thr His Val Glu Ala Gln Glu His Gln Pro Glu Pro
    210                 215                 220

Glu Glu Glu Thr Glu Gln Pro Thr Leu Asp Tyr Asn Asp Gln Ile Glu
225                 230                 235                 240

Arg Glu Asp Tyr Glu Asp Phe Glu Tyr Ile Arg Arg Gln Lys Gln Pro
                245                 250                 255

Arg Pro Pro Pro Ser Arg Arg Arg Arg Pro Glu Arg Val Trp Pro Glu
            260                 265                 270

Pro Pro Glu Glu Lys Ala Pro Ala Pro Ala Pro Glu Glu Arg Ile Glu
        275                 280                 285

Pro Pro Val Lys Pro Leu Leu Pro Pro Leu Pro Pro Asp Tyr Gly Asp
    290                 295                 300

Gly Tyr Val Ile Pro Asn Tyr Asp Asp Met Asp Tyr Tyr Phe Gly Pro
305                 310                 315                 320

Pro Pro Pro Gln Lys Pro Asp Ala Glu Arg Gln Thr Asp Glu Glu Lys
                325                 330                 335

Glu Glu Leu Lys Lys Pro Lys Lys Glu Asp Ser Ser Pro Lys Glu Glu
            340                 345                 350

Thr Asp Lys Trp Ala Val Glu Lys Gly Lys Asp His Lys Glu Pro Arg
        355                 360                 365
```

-continued

```
Lys Gly Glu Glu Leu Glu Glu Glu Trp Thr Pro Thr Glu Lys Val Lys
    370                 375                 380

Cys Pro Pro Ile Gly Met Glu Ser His Arg Ile Glu Asp Asn Gln Ile
385                 390                 395                 400

Arg Ala Ser Ser Met Leu Arg His Gly Leu Gly Ala Gln Arg Gly Arg
                405                 410                 415

Leu Asn Met Gln Thr Gly Ala Thr Glu Asp Asp Tyr Tyr Asp Gly Ala
            420                 425                 430

Trp Cys Ala Glu Asp Asp Ala Arg Thr Gln Trp Ile Glu Val Asp Thr
        435                 440                 445

Arg Arg Thr Thr Arg Phe Thr Gly Val Ile Thr Gln Gly Arg Asp Ser
    450                 455                 460

Ser Ile His Asp Asp Phe Val Thr Thr Phe Phe Val Gly Phe Ser Asn
465                 470                 475                 480

Asp Ser Gln Thr Trp Val Met Tyr Thr Asn Gly Tyr Glu Glu Met Thr
                485                 490                 495

Phe His Gly Asn Val Asp Lys Asp Thr Pro Val Leu Ser Glu Leu Pro
            500                 505                 510

Glu Pro Val Val Ala Arg Phe Ile Arg Ile Tyr Pro Leu Thr Trp Asn
        515                 520                 525

Gly Ser Leu Cys Met Arg Leu Glu Val Leu Gly Cys Ser Val Ala Pro
    530                 535                 540

Val Tyr Ser Tyr Tyr Ala Gln Asn Glu Val Val Ala Thr Asp Asp Leu
545                 550                 555                 560

Asp Phe Arg His His Ser Tyr Lys Asp Met Arg Gln Leu Met Lys Val
                565                 570                 575

Val Asn Glu Glu Cys Pro Thr Ile Thr Arg Thr Tyr Ser Leu Gly Lys
            580                 585                 590

Ser Ser Arg Gly Leu Lys Ile Tyr Ala Met Glu Ile Ser Asp Asn Pro
        595                 600                 605

Gly Glu His Glu Leu Gly Glu Pro Glu Phe Arg Tyr Thr Ala Gly Ile
    610                 615                 620

His Gly Asn Glu Val Leu Gly Arg Glu Leu Leu Leu Leu Leu Met Gln
625                 630                 635                 640

Tyr Leu Cys Arg Glu Tyr Arg Asp Gly Asn Pro Arg Val Arg Ser Leu
                645                 650                 655

Val Gln Asp Thr Arg Ile His Leu Val Pro Ser Leu Asn Pro Asp Gly
            660                 665                 670

Tyr Glu Val Ala Ala Gln Met Gly Ser Glu Phe Gly Asn Trp Ala Leu
        675                 680                 685

Gly Leu Trp Thr Glu Glu Gly Phe Asp Ile Phe Glu Asp Phe Pro Asp
    690                 695                 700

Leu Asn Ser Val Leu Trp Gly Ala Glu Glu Arg Lys Trp Val Pro Tyr
705                 710                 715                 720

Arg Val Pro Asn Asn Asn Leu Pro Ile Pro Glu Arg Tyr Leu Ser Pro
                725                 730                 735

Asp Ala Thr Val Ser Thr Glu Val Arg Ala Ile Ile Ala Trp Met Glu
            740                 745                 750

Lys Asn Pro Phe Val Leu Gly Ala Asn Leu Asn Gly Gly Glu Arg Leu
        755                 760                 765

Val Ser Tyr Pro Tyr Asp Met Ala Arg Thr Pro Thr Gln Glu Gln Leu
    770                 775                 780
```

-continued

```
Leu Ala Ala Ala Met Ala Ala Ala Arg Gly Glu Asp Glu Asp Glu Val
785                 790                 795                 800

Ser Glu Ala Gln Glu Thr Pro Asp His Ala Ile Phe Arg Trp Leu Ala
                805                 810                 815

Ile Ser Phe Ala Ser Ala His Leu Thr Leu Thr Glu Pro Tyr Arg Gly
            820                 825                 830

Gly Cys Gln Ala Gln Asp Tyr Thr Gly Gly Met Gly Ile Val Asn Gly
        835                 840                 845

Ala Lys Trp Asn Pro Arg Thr Gly Thr Ile Asn Asp Phe Ser Tyr Leu
    850                 855                 860

His Thr Asn Cys Leu Glu Leu Ser Phe Tyr Leu Gly Cys Asp Lys Phe
865                 870                 875                 880

Pro His Glu Ser Glu Leu Pro Arg Glu Trp Glu Asn Asn Lys Glu Ala
                885                 890                 895

Leu Leu Thr Phe Met Glu Gln Val His Arg Gly Ile Lys Gly Val Val
            900                 905                 910

Thr Asp Glu Gln Gly Ile Pro Ile Ala Asn Ala Thr Ile Ser Val Ser
        915                 920                 925

Gly Ile Asn His Gly Val Lys Thr Ala Ser Gly Gly Asp Tyr Trp Arg
    930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
                965                 970                 975

Gln Cys Asn Phe Ile Leu Ala Arg Ser Asn Trp Lys Arg Ile Arg Glu
            980                 985                 990

Ile Met Ala Met Asn Gly Asn Arg  Pro Ile Pro His Ile  Asp Pro Ser
        995                 1000                1005

Arg Pro  Met Thr Pro Gln Gln  Arg Arg Leu Gln Gln  Arg Arg Leu
    1010                 1015                 1020

Gln His  Arg Leu Arg Leu Arg  Ala Gln Met Arg Leu  Arg Arg Leu
    1025                 1030                 1035

Asn Ala  Thr Thr Thr Leu Gly  Pro His Thr Val Pro  Pro Thr Leu
    1040                 1045                 1050

Pro Pro  Ala Pro Ala Thr Thr  Leu Ser Thr Thr Ile  Glu Pro Trp
    1055                 1060                 1065

Gly Leu  Ile Pro Pro Thr Thr  Ala Gly Trp Glu Glu  Ser Glu Thr
    1070                 1075                 1080

Glu Thr  Tyr Thr Glu Val Val  Thr Glu Phe Gly Thr  Glu Val Glu
    1085                 1090                 1095

Pro Glu  Phe Gly Thr Lys Val  Glu Pro Glu Phe Glu  Thr Gln Leu
    1100                 1105                 1110

Glu Pro  Glu Phe Glu Thr Gln  Leu Glu Pro Glu Phe  Glu Glu Glu
    1115                 1120                 1125

Glu Glu  Glu Glu Lys Glu Glu  Glu Ile Ala Thr Gly  Gln Ala Phe
    1130                 1135                 1140

Pro Phe  Thr Thr Val Glu Thr  Tyr Thr Val Asn Phe  Gly Asp Phe
    1145                 1150                 1155
```

```
<210> SEQ ID NO 4
<211> LENGTH: 469
<212> TYPE: PRT
<213> ORGANISM: Homo sapiens

<400> SEQUENCE: 4
```

-continued

```
Met Phe Ser Glu Gln Ala Ala Gln Arg Ala His Thr Leu Leu Ser Pro
1               5                   10                  15

Pro Ser Ala Asn Asn Ala Thr Phe Ala Arg Val Pro Val Ala Thr Tyr
            20                  25                  30

Thr Asn Ser Ser Gln Pro Phe Arg Leu Gly Glu Arg Ser Phe Ser Arg
        35                  40                  45

Gln Tyr Ala His Ile Tyr Ala Thr Arg Leu Ile Gln Met Arg Pro Phe
    50                  55                  60

Leu Glu Asn Arg Ala Gln Gln His Trp Gly Ser Gly Val Gly Val Lys
65                  70                  75                  80

Lys Leu Cys Glu Leu Gln Pro Glu Glu Lys Cys Cys Val Val Gly Thr
                85                  90                  95

Leu Phe Lys Ala Met Pro Leu Gln Pro Ser Ile Leu Arg Glu Val Ser
            100                 105                 110

Glu Glu His Asn Leu Leu Pro Gln Pro Pro Arg Ser Lys Tyr Ile His
        115                 120                 125

Pro Asp Asp Glu Leu Val Leu Glu Asp Glu Leu Gln Arg Ile Lys Leu
    130                 135                 140

Lys Gly Thr Ile Asp Val Ser Lys Leu Val Thr Gly Thr Val Leu Ala
145                 150                 155                 160

Val Phe Gly Ser Val Arg Asp Asp Gly Lys Phe Leu Val Glu Asp Tyr
                165                 170                 175

Cys Phe Ala Asp Leu Ala Pro Gln Lys Pro Ala Pro Pro Leu Asp Thr
            180                 185                 190

Asp Arg Phe Val Leu Leu Val Ser Gly Leu Gly Leu Gly Gly Gly Gly
        195                 200                 205

Gly Glu Ser Leu Leu Gly Thr Gln Leu Leu Val Asp Val Val Thr Gly
    210                 215                 220

Gln Leu Gly Asp Glu Gly Glu Gln Cys Ser Ala Ala His Val Ser Arg
225                 230                 235                 240

Val Ile Leu Ala Gly Asn Leu Leu Ser His Ser Thr Gln Ser Arg Asp
                245                 250                 255

Ser Ile Asn Lys Ala Lys Tyr Leu Thr Lys Lys Thr Gln Ala Ala Ser
            260                 265                 270

Val Glu Ala Val Lys Met Leu Asp Glu Ile Leu Leu Gln Leu Ser Ala
        275                 280                 285

Ser Val Pro Val Asp Val Met Pro Gly Glu Phe Asp Pro Thr Asn Tyr
    290                 295                 300

Thr Leu Pro Gln Gln Pro Leu His Pro Cys Met Phe Pro Leu Ala Thr
305                 310                 315                 320

Ala Tyr Ser Thr Leu Gln Leu Val Thr Asn Pro Tyr Gln Ala Thr Ile
                325                 330                 335

Asp Gly Val Arg Phe Leu Gly Thr Ser Gly Gln Asn Val Ser Asp Ile
            340                 345                 350

Phe Arg Tyr Ser Ser Met Glu Asp His Leu Glu Ile Leu Glu Trp Thr
        355                 360                 365

Leu Arg Val Arg His Ile Ser Pro Thr Ala Pro Asp Thr Leu Gly Cys
    370                 375                 380

Tyr Pro Phe Tyr Lys Thr Asp Pro Phe Ile Phe Pro Glu Cys Pro His
385                 390                 395                 400

Val Tyr Phe Cys Gly Asn Thr Pro Ser Phe Gly Ser Lys Ile Ile Arg
                405                 410                 415
```

-continued

```
Gly Pro Glu Asp Gln Thr Val Leu Leu Val Thr Val Pro Asp Phe Ser
            420                 425                 430

Ala Thr Gln Thr Ala Cys Leu Val Asn Leu Arg Ser Leu Ala Cys Gln
        435                 440                 445

Pro Ile Ser Phe Ser Gly Phe Gly Ala Glu Asp Asp Asp Leu Gly Gly
    450                 455                 460

Leu Gly Leu Gly Pro
465


<210> SEQ ID NO 5
<211> LENGTH: 39000
<212> TYPE: DNA
<213> ORGANISM: Homo sapiens

<400> SEQUENCE: 5

ccagacatag gcaaggcgca aggtgataca gtaggcagcc accatggggg ccaggaggct      60

ccagcagagg ccacacaacc agcccagaat ccaggacaga gagctggaat ggagacaggg     120

aagccagata ccaggccaga ctggccaggt gctacaggcc tgtgggccag gccaggcttg     180

gggacttcgt cctgggtgtg aaggagacag gcacccctga ggccttccct ctgcatctcc     240

agcccaagct aagcgcaaac tcttaggttg gagtaaggag taaccccctg ccaagtttct     300

cctgtcctca ggctccaccc accacctatg ctgcctggcc ccatggggca cacgctcagg     360

cccagcctgg gaaagcaact gcacctgcct gtgctatgct ggcccttctc agcctcaatg     420

ccctcctccc tccccgacgc accctcgtgg cccccgctgg gccccctgat gcaccctcat     480

gtctccatgg caacctgctc agagtgtggc cctgcccttg gctcccctcc acacctgtgt     540

cccaggcagt gccacggcac tttcctaaac agaaggatgg gcttcaaaac agtcccagac     600

actaaacaca cctgcatttt gggtccaagt aacttctgac aagacgagtg cccctacaca     660

ctctcagtcc tatccactat gggcaaggag cctgaaggat cccccagaac tggctaaagc     720

cctcagtctc ctcctccacc ctgagcacct tcacgcggca gagtggccct ggatgtcagc     780

ttcttgctcc ccatggtctg cacctggaca ggtgctctca ggtgtgtggg tgggcaggtg     840

gcaggtccca agagccaggt gcaaagaatc taggccagtg cccacgagtg ctgcagtgtc     900

tgtccccagc atggtatcta gggctccact tgcctatcag ctgtaatcgg aggaggcttt     960

ccaggccagg cctcccccag gaaggctgca ggcactgcgg atcgtgcgcc ctcacatgca    1020

ttattcctga ggcccttctg cagatgccat cagggcagca actctgatga ggtattaggg    1080

cacagcacac agggctaagc caccctgtac tgggccaagc gctacaggca aaaaggacac    1140

caccgacggg catttcattc atcgctttta tttttatata tttttgagag ggagcctcac    1200

tctgtcgccc aggctggagt gcagtggcgc gatcttggct cactgcaact tctccctcct    1260

gggttcaagt gattctcctg cctcagcctc ccgagtagct gagattacag gtgcccgcca    1320

ccatgcccag ctaacttttg tattttagta gacatggggt ttcaccatgt tggtcaggct    1380

ggtctcgaac tcccgacctc aaatgatctg cctacctcag cctcccaaag tgctgggatt    1440

acaggcatga gccactgcac ccggcccatt catcactttt aaatagcacc ctctgaacaa    1500

agctccctgg gccacatgac cctaagggtt accccatccc accccaaccc aggtctggca    1560

ggtcctcaga acaggaaaag ctgagcactg cccaaggctg cttgctgggc cagtcagaga    1620

ggtctctgcc ttccaggatc agaagtacag gctgaaagca gccttgggcc cgcctccctg    1680

ggaggctaca gaggcttcag agggttccct gaactcaaaa ccagatgtga gacttgaatt    1740

tgacttaccc ctggttcacc tcccaaccaa agcaggggtc agctttggct cctccaggaa    1800
```

-continued

```
ccaggaagct tccaggtacc ctgtggagcc ccctctgctc ctgaaaagtt gccacctgtg   1860
cttggtggga tgccaggtgg tctcagattg accctggggt cagcggtgag ggacaggaag   1920
cctacagcgg gatcaggatg gggatggggc ctcctgtccc atggctctgc agctatgagg   1980
cagctttcct agggtgggtc tcctggctgc agctaagacc aggcaacagg attcagcaat   2040
gacagggctt cttctactcc agggctccct cacctggtta acagcaaaaa agaaaataca   2100
gttcctgcta gcaaggtcta tagaaaggag gtgaaggagt caggcctgca gctacctctc   2160
ctggacagga gctggtcagg ataacttgga cccttgcatg cggcaggccc acaggcacac   2220
agcatgaggc cactctctcc cccgggggaa gggcttggtg aagaaaggat tcccctgaag   2280
cacaaagaaa gcacaggacc actgtgaaat ttcaagacaa ctttatccag acaggcgcct   2340
ctcaaataga acacagggaa gttaggcagc agttactaaa atacagtctc gccaaatgat   2400
ttacaacaga acacaacagg agcaggggat ctgtgggtgg ggctgggctg ggccctctat   2460
ctcacagggc ctgagtcaag ccagcccgcc ctgcaaggca ggggctgacc tgcaagcgga   2520
gatctcactt cctcttaccc caaattcata cctccatttt ccccgccccc atctctcccc   2580
agggtcctca agtgggaaag ggagaggtag catccctcgg atccaggccc actccactcc   2640
gtctccggca ccagtgggca ggctgagtct gggcctcaag gggccctggg cttagggtat   2700
ctatggcagt aggaaaatga catggacagg ctcttcaggg gtaggctaaa gtcctctggc   2760
cagcagtacc cagagaaaat gggcagcagc aggtaaacca gccaggaggt ggagtcctct   2820
gaacccacag cagaccccac cctcctgccc agcccctgcc cacattgggg gtcaggacca   2880
ctgagactct ggtcaggaca gtgggtgctc tcagcagtgt ggcaagctca gagcagagct   2940
cccaaggacc ataccacact ggttcaaaac ccataggtga caccatccca gcagaagctt   3000
ccatgggtgc tggatcccag ggctgcatcc tgagcacagg tgggcagact ggaacataac   3060
actaggaccc aagggatcca gaacatttta ggcccatctc ctgggctgct ccagcctgtt   3120
gccatgactt gggcagtgag tgggcctcct gccaggtggc agggcacagc ttagaccaaa   3180
cccttggcct ccccctctg cagctacctc tgaccaagaa ggaactagca agcctatgct   3240
ggcaagacca taggtggggt gctgggaatc ctcggggccg gctggcaccc actcctggtg   3300
ctcaagggag agacccactt gttcagatgc ataggcctca ggcggttcaa ggcagtctta   3360
gagccacaga gtcaaataaa aatcaatttt gagagaccac agcacctgct gctttgatcg   3420
tgatgttcaa ggcaagttgc aagtcaaggc aagtgtccca gaggccctgg gcagctgagt   3480
gcacctgtgt ttgatcttcc cctgatgatg gacactccca gctgaccatc caaacaccag   3540
gaaaacatcc cccttttcctg ggctcagttc ctagtctact tgctggtacg aacccaaccc   3600
acacactccc cgcccacaat gcagctcctt ccaaatcctc ccacaagcca cctttgtggg   3660
acttggaagc tgcttaggat gggccctgcc ctctgcggga agccaatcct agcagaaagg   3720
taagctaaac aacagtctca gaatctgaga cccagtgact gttccccccg ccccaggcct   3780
tgggcctgaa gtgggggcct gcctgtggcc tctgtggtgg gctcactccc acccccaaca   3840
gtggccccag gagaggcttt cccaagagtc ttcaaactcc acccacccca gccctagcat   3900
cagggactcc ccacccccca ctggagtgtt aatatcatta atgtacaaat aagatccaaa   3960
gatataccaa agatcgagaa acagctggct ccgacctccc tcccacagag ccttcccagg   4020
gttagctgaa aaagagccct ttggcatcta cagaagccag tcggagttta tggtttcatt   4080
tgcccaaaaa tacacctttg gggacctcaa attctttcca agaatcacta ccacacatat   4140
```

-continued

```
gaatttgaac attcgccacc cttccaccat ccatttctcg caggaacttc aaaataaaaa   4200
tggccagtct gcccccactc tggctcctcg tctatggctg tctcttcttt tccaggggct   4260
gcagttctga tgtgaatgat ggtgccattc cagcattggg cctctggcag gctgcatcac   4320
atgatggcac agcatgagtt ttgtttccgg gccttggaaa aaaacaaaga ggagctgaga   4380
aggaggactg acgaagtaag ggaagcccca atcctggcag gcgtggcaga gggagctcca   4440
caggacacag ccaggcagag aaactagcac tagaacaggg tgggggtgga ggccttgagg   4500
gaagctgtcc acaagcaatt cccatcacca agcacaaggc gggccccggc ttccaaaact   4560
agtctgggat ccttttttcct ttcttttctc acaccccatt aatgctatca aaaagtgagt   4620
aaaattccta cagttaggcc aggtacaaac aaaggaccaa taatacaaat gggattggca   4680
gaatatctta actttgcccc actcctgtct tcacacaatg ctatctgacc accacggtgg   4740
tgtttcttcc tagaagatgg tcctgaggac aacagatgtg gttcccactt gggatgtggt   4800
ttgtggggac cactgttgcc accttctctc ttgctttctg gtcacagact atcttcctaa   4860
tcccacctag ccatctccct ccaatgtgca catgaaagca aatgtgtgtg gacagaccaa   4920
gtaaatttgt ccctatgact atccaaccat gggccaacag tgccatctcc acataggaag   4980
acatgagcac tgacctgaga gaaagcggca gtcagcagca cccatccttg tcaattaaat   5040
attttctgtc aaagggaaat taaaagctta agaacctctt caggaaggct gaattgcttg   5100
catcttaaag acttatgtct actcagcaga aagaggaata agattcaaca gtaaatctct   5160
ggtgatcaga acttgaacca gccttcctgg actgggagta ggagttcaga aatcagccag   5220
agcagcagag ggcagagcag aggcaggagt ggaacaaggc ctcggcccgc atcgactcca   5280
acggcgccca agtgaactgc ctccaaccac ctgggcctga ggcgctcacc ttaggctctt   5340
gccgcacaag gaatcatcca ccatgattca acagtctaag aaagacccgt tcatagtgga   5400
gagtgccaga agcagcaagc tgcgactgct ctctagagag aacacccagg aggcagcagg   5460
tgctgggtac tcacagtttt atagaaggct ttagactgtg ttcccagcac ctcggatttg   5520
gacaccaagt catctagctt ctcacctcgc tctaacagag actccatggt gttgtgctgg   5580
acaaaaaaga aaagagaatc cagctctgtt cagtacgtgc cctgacatga gcccctcata   5640
tttcagtcat gggggaaagt gccttacctg ggttcctctc caacacacac aaacttcacc   5700
tctaggtgtc gagactcggt ccaagaatag ttactgtcca agtggatgga acagaacctg   5760
gtgacattcc cgtgaaatct agaagatcta actgggatgt agcagacttc ccaaaaagct   5820
gtccccagca caggcttaga taaccagcac tccaggaaaa ctcatatata tatatacaca   5880
cacatttata tatacatttg tgtgtgtgtg tgtgtgtgca cgcacatgtg cgtgtgcatg   5940
gagctttgga aaaaagagta gctgggcact atatgattgt actgggttgg agagtgaccc   6000
acaccgcacc ccccaacccc aaccgcatcc cagaaattaa catccccaga atctctgaat   6060
gtgaccatat ttagaaatag ggtcttggca gatgtaacta gttaggaaga ggtaatactg   6120
gattagggtg gcatctaatt ccatgactga tgtcctggta agaaacggaa acacacacac   6180
agaaggtcac gtgacggcag aggcagagcc tgaagtgatg cacctctaat ccaaggaatg   6240
ccaaggatgg ccagcagcca ccagaggctg gagagaggcc tgggacagac actcagagcc   6300
ccaaaagaca ccagccaggc ccacagagct atctgttaaa agcaaatatt tgagggtttc   6360
tgttgacagc agccacagga aacaaaaggc ggtgggaaat ggctattgag cacttgatgt   6420
gaggcaagtc caaactgagc agcgctctga gtacagacac accagatttc agatgcaaac   6480
tcacacatgc ttcattagta agttttatac tgaaaaaaaa acaagtttta taccgattac   6540
```

-continued

```
atgttggaaa aattgtattt ggatatactg cgttaagtaa aatatataat taaattaaat   6600
tctacctatt ttccttttat cattttaaaa tatggctcct agaaaattct aagttacaca   6660
catgccccaa atatatacca gacagcacta tgacagaaca tgtcctgcct tctaaatggg   6720
ctatgtccta aatgtcatca ctacaaactc tgacttagga aatgaaaaca ctgaccccat   6780
gggaaggggt ctagagatgg agacctcaca agagccagca gctctgctgc cagggccctc   6840
aggaagcagc agctcgcttc tctcctcaga tggccactgc tgcagcagct agatgcacac   6900
atgaagcgcc atagaacaag gagccagcaa gaatgtcctt catccctaca cacagctgag   6960
cgactcaaat ttttaacaca gaaagttaac tgattcagat atgcacacca atcatctaga   7020
ttttacaact gcagctagat gaggctgggt gaataggact catccactcc ccaccgtggg   7080
gagaggagaa acagcgggtg tcccaggtgt catggtactc agactaggac ttgagcaaca   7140
gaaagagatg gcttgaggag aaaacggaga aatgccacct aggtggtaag aaagctcaca   7200
aggtttcaaa agacacagat accatgagac tttcacatct atcgttcatt ccaaagccac   7260
gttatttgga gtgcagtcag cacacctgtg tttgaagccc ctgggatgct ttttataaaa   7320
tgcaggttcc caggctccat cgcaggccaa caactccaac cccaggagac gctgatgtac   7380
acactaaagc tatgcctgtg taaatggtaa agctttgtat gtgggtttca atccactcca   7440
ggtatctatc aactgctgag catggtataa actaggcact gtatcatgag caggatggaa   7500
agatgtccca gtgctcatac gctggtcagg gagacatgta aacaagcagt gacaaaactg   7560
tgacatctgg tcagaaaggc ccaaccttca ggcgcctgtg tgtgagctgg gcaagaaagg   7620
gtataagaga gaacagggcc cagtcaggag actgtgagtt agtttgcact ttatcctggg   7680
gcggatctga gagctgctga agggttctaa gttgtgcaga tcaatgacta ctctctggtg   7740
gacagactgg aggtgagcag gaggcaaggg gaccacttag aggcaaaggc tgtaagagaa   7800
aaacctgaga aaaacagata gctgcttaca ttccacttgt atgcaaaaat ttaaaaaaaa   7860
agagttgaag caacagttac aaatcaggag atttcagctc aaaatgcagg gttctggctc   7920
ttttcaaagg ggcctatgtg acaaccctgg gcccatattc cagaagctgc cctgtggtca   7980
gtgcacggtg cttcaatctg ttcaccttca atgcaaacgc tgcaagggga ggcacctgtg   8040
gggtgtggag gcacccgaaa ccctaacaaa ggcaccaggg tgggaatcca ggtcttcaga   8100
agccaaaccc taggaaccca gtaaatggtc agacaggcag tagccatgag gaagggagac   8160
ttgagggttc cactggttcc cagcttggtc ccctagaaac aatgggtgcc attaaccaag   8220
agaagggtat aggaaagaca gtctgatgcc cggggtgggg gaaggggtgg gcaatcccac   8280
ttgctggaga gtgccgtggt tactattata ttaaaacgag gatggatctg tgcatgcctg   8340
gccagtggaa atcgcacccc cgcctcagtt cttgggcttg ctctccatct tcctgcttac   8400
cagaatgatt ttggtctcat ctagttcggc ctgcacttta gtcatgggat cagcttctcg   8460
tgggttctag gaaagagtga aaaataataa agtcaggact ggagtggcta cctgcaaaca   8520
aaacctaaaa ctgaggaagc tggacaaact ttcacaggtt aaaaaccaca gcctgggccg   8580
ggcacagtgg ctcacgcctg taatcccagc attttgggag gatgaggcgg gtggatcacc   8640
agagatcaag agttcgagac cagcctgacc aacatggtga aaccgtctct actaaaaata   8700
caaaaattag ccaggcgtgg tggcacatgc ctgtaatccc agctactcgg gaggctgagg   8760
caggagaatc gcttgaaccc aggaggtgca ggttgagtga gccgagattg cgccactgca   8820
ctccagcctg ggaaacagag tgagactcca actcaaaaaa caaaaaacaa aaaaaaaaac   8880
```

-continued

```
ccacagcctg tttaacatgt aacagaaacc caaagcctgc ctagagcttg ggttccccgg   8940
tctgaacgta gattctctgt tttccaaaca gtaaggcttg agagaggaca ccagcatcag   9000
aagctgtcag aagtaattag accagaacta tcagggcagt tggctttttc agtttcacat   9060
ggattctggg ccacatggtg tctgctgaag cttcctttaa ccctacctgg tatctactga   9120
ggtgaccatc cagggctggg taatggattg tagcagggga tcctactggc cagtctatcc   9180
tgtcgacttg cttggagaat tcatctagta cctgcaagac aaaggagact caacaagcct   9240
cccactgtgc actcaccagt ggtctcaatg acagggcttc acccctgagc acctcaccct   9300
gaatgaggct ccttggcctt cacagcccag gaaggaggaa tgagggggac atataatggc   9360
aacagagaaa atctaggcta aagttctttc caaattttta tcattaaaac atatcctaaa   9420
tattctgaga atcaaaagta tgcccagccc gagatgaacc tcacttgggg agtaataaag   9480
gtatttgaat tttaaactac agatttccag aaaaaagggg cactggtcct ctaattttcc   9540
aaagcaattt tttaaaaaag agaattaggt cccctagatt taagaaacca ccagattcca   9600
tgtgtttgga ggtattttgg tgctctgggg tataggatga agcctctgac ttcaaagagt   9660
taatattagt aattagcacc gtacgcaaaa aaatttaaag aatgcttagg tgctaagctc   9720
tgtggtgcaa ctgactgaca tcaaggtaga gggatgcagc aactgcagga ggcaatgggg   9780
agagtgaagg cattcaagag ggagactcct tgagcagaag cacagggggc gagaacacaa   9840
ggcacagctg tctccgaggg tcccatccca gagaatagat gctatgactc agtggcctag   9900
acccagctca catgagggac agcaccgggg aggaaaccca tacagggatg ccaaattgtc   9960
tcttgggttg cagggaaggg ggctgaaaaa tgtgttgact ttggacacat catttcatcc  10020
cttatgtctc agggactgcc atcaacccct gtcccagtcc ataaatgtgc ccattcatca  10080
tccaagtcca ggagaggcaa ataaaaaact caccttctcc agcaaggtaa aggccacccg  10140
ggatgggtat tcattgtcag caatgaccac acctgcaaga ctatcattcc ggacgtagac  10200
gtggcacaga tagtctaagg agacaagaga tcagacacat ggatgctgac atgagggctt  10260
cagacttctt ttaatccccc caaatcaaag catccaatgt taggccaaat gaagccactc  10320
ggaagctcaa tagctctggg caagtcttgt ggagaggctt agcagcacag cccaatgggc  10380
cacacacagg agcttggccc aacgcctgct ttaggaccag taaataccca gaggcccagt  10440
atgcaaagcc agggcttaaa gaaacagcca gtggtgcaga aaacacaccc ttgacaacat  10500
ggccccagga gcatttccaa gtgtattcct taagctcggg tcaggccaag ctatatctta  10560
gggatctgga gcccttgggg ctctgtgctg ctcccaaact tagggaaccc tggacaagcc  10620
aagaggcctc tgctttctta aaaaatcttt tcagagcagc caaaagacag gaaattaccc  10680
cccagggcct cagtcttcca tattatagca acctgctggg tttgctccac tctggtgggt  10740
gactgggagt agggggggtta gtctagaaaa agattagcta ctgccagcta aggcctccag  10800
agcactgtgc taaaatcctc atatgattga aaggtacagt tgtacaggtc ttccgcaaaa  10860
tattcacaat ccacaggatt gttcatttcc atcactttga aaggattcag agttgataca  10920
gctaaccata tccccaagga aagagaaatg taaggattac agcttacaaa taagaacctt  10980
cttgtcctta aggatctgac ccagaagatt ccaatgctaa acaacagaaa aacaaataaa  11040
agaggaggga atgatggtga gcccctgaaa tcagaaaaga gcagagataa atgagaacaa  11100
gaatgaggag gaggaagagg acagggggtt gtcaccaatg ctctccagat tttgtatacc  11160
atccccaatt aagattcaaa catggggtca aagtgcatac cctccaaaga aactgagaac  11220
ctggtcagtg gaggaattgt ctttaagtaa taaacgtggg aagggcaggc acagtttgaa  11280
```

-continued

```
gaacagagca agaacactga aatatttgtg atgcgatttc acttctatga tgttaatagc  11340
acagagatcc cacataaagt gtatatagtc aatcctgcct gtatcataac tgacatttat  11400
atcatcaatt cagtaactct atgtcacgtg acttgaggtt agcataagtg tgagatgatc  11460
tttgtcccta cctgatgaaa ctcatgtaac tctttcctga tctgtctgta taacatacac  11520
atctaaataa atgcctaaac ctgaattatc agaaagaaaa aatagttttt tcagattcct  11580
gatcaaaaaa tctacgatgc acagaataca tatagtacct caacagtgct agctggaaat  11640
cctttttgga ggggtctgca actctgaaga ggatagggaa gaatacgata tgaaggctgc  11700
ttactgctcc aaaagagtca gaccctaatc ttaaatgagt ctaagtttga gggcaatttt  11760
atctgggaag ctcagacttc aacagtgggc acagaattct gcataaatag gaaaaggaag  11820
aggtgggaaa gagagaacaa gctagaggag gagtagggtc ccagtagaaa ggagaaagct  11880
gggtgctatg tgaggtgagg catggcagcc aggccagcac acgcacagaa gttggagggt  11940
cttcttacct tgttctttga cagaagctct agtgcctttc gatgagcgct ccacaatcag  12000
ttgactcgtg aaggtcatga attcctgaac gctaagaaac acaaaatgta tttattgcct  12060
acttcttatc accttgtccc caacacagtg gaaagtgacc tctgggctta tacattaagt  12120
agacattgct tcttggtttc attcctttcc ctcccatccc tagtaacaaa cactctataa  12180
atgagcacaa atactgataa ttatgaatta tcatcaccat gaaagctcca tctgtttgct  12240
acctggctca ccaaaacagg tgaattttct ggggggtttt tccacaggat acagtcaatt  12300
ttacattttg gtgaatgcat aatttggaat gcaatggaaa aacaagaggc aggtcctgct  12360
ctcaaggtcc caataacttc caagaagcag gacatttata agaactgcac tagaagaata  12420
gtgtgcaaaa actgtcaggc agaaatgcac aaccatttat ggctgtgtcc acatgacaga  12480
ccctcgcaat gccacataca cccatagtga gtgctggctc aggtctgctg gggctcgtcc  12540
acagaacgag cgcaagacac tctggatgga acaaaaggaa aactgctcat ccaagacaaa  12600
gaagtgggaa atggctcata caaagggtga aagggagaag gtccatcatg ggctcaacag  12660
agagatctat ccagaacaga acagtcacag gagatggtac agccagagga agaggtgctg  12720
acaaggagcc tccaactgag gatgtgatat aaagggcaac cagggccatc aaagcagggt  12780
gctcaaatgg gagtctgcag caggctccag cagagccata taggtaactg aaggcctgac  12840
tctgggcctg tgtgctgtgc ctccacatta aaaaaatcaa gatttgtgca acagttaaac  12900
gaggtaatac gtgtaaagca cttggaacaa tgcctgcaca cacagtatta cttgttaata  12960
tcttgaggga ctgaagtgat caaaataacc cctcagaaaa gaagacctca aacaaggaag  13020
gctttgcagt aaacctagag acagcatttg agacacggct ataaagagac aaaggaagaa  13080
ctgcattgtg acagcatgta tacaaagacc aaaaaagctg ggaaactact ttttcaactt  13140
tggaatcggg taattatagg gcacaaagga cgtaagtaaa gcggtcttat aagaaaacaa  13200
gctcaggccg gacgtggtgg ctcaagcctg taatcctagc actttgggag gccaaggcag  13260
gcggatcact tgagctcagg agttcgagac cagcctggct aacatggtaa aaccccatct  13320
ctactaaaaa tacaaaaatt agccgggtgt ggtggtgcgc gcctgtaatc ccagctactt  13380
gggaggctga ggcaggagaa tcacttgaac ccaggaggcg gaggttgcag tgagctgaca  13440
ctgtgccact gcactccagc ctgggtgaca gagcaagact ccatctaaaa taaaataaat  13500
aaataaataa atcagctggg acatgtgttg ttttaagaca tattagtaga gatgtccctt  13560
tagtgttgca gctgttagtc attggaaact agtgtgggca tcccaagcag gtgaggtata  13620
```

-continued

```
agtcctacaa gtgaaatctc tgagaatctt aagtactaat gggaaggaaa aaggaaaaag  13680
aatcagagcc aagttggcac caaaagttcc atctgagaaa agcaacaaca cagagcagtg  13740
aatgtaggcc atggtaaaga ctgcaaagac caagaacccc aagaaggagc taaaagataa  13800
tgcagcaatt ccgcttctgg gtaaatacca aaaaaatgcg agcagggtct tgaagagata  13860
tttgtacatc catgttcata gcagtatcat tcacaatggc tgaaatgtgg aagcaaccca  13920
ggtgtccact gacagatgaa cagataagca aaatgtggtg aataatacaa tggattattc  13980
agccttaaaa aggaaagaaa ttctgatata tgcaacaaga tgcatgagcc ttgaggacat  14040
tatgctacat gaaataagcc agacacacaa aaactatatg attccattta tctaaggtcg  14100
ccagaaaagt caaaatcaca gagacaaatt agaatggcag ttgccatggg ctgggggaga  14160
agggaatgtg tttaatagac acgaatttga taaaaaggag ttctggagac gattgacagt  14220
gatggctgca caacactatc aatctatttc atatcaatgc actcactaca cgcttaaaga  14280
tagtgaagat aaattttgtg taccatttta ccacaattaa aaatattttt ttaaaagaac  14340
tcaaagaagc agaaagtttc aacaaaataa catttttttt tttttacatc cagcaagtcc  14400
ttggcaaaga actctcatca agaaccagct gcactgaagc agggaaaaca gaatccaaac  14460
ggcagattcc atcagatttt gagacaagat gaccatagat accgaccatg tagggtcctc  14520
cttctttcgt gcctgagtca ccccaatccc tcccacgaat ggtctggaag tgtctgtgtt  14580
acttctaaca cgttccagca attaaagcgc cccagaaaca agtaaaagcc tgtaagccct  14640
acagatccca tgcttcattt gcatcttccg tgtggaatcc ttttgtacca ctagtgtcca  14700
actaaaaagc gttaaacctg gctttcagtt ctagctggtt gtgatataac ctcttggtac  14760
ctcagtgact tcacccatta aaaacaaaca aaaaaaagta tatcactatc tctcatacag  14820
aattgttggg aagccccgca agaaaatcaa aatatggctc tcaagatgcg gcacccaagc  14880
tcccagagtc agaatcactg ggtgggaagt gttggtctaa aatataaata ccgaggcctc  14940
aatctactaa ttcagaacat cttggcatga agcttggaaa tctgcactac ttcacagtct  15000
ccttaaaatt tttacacgac agaaatttga aaaacactga gtagagaact atattctaga  15060
atggtataag ctcttaaaga gctaatgttg gttcctcaaa ggtagagtcc acggccagat  15120
tccattatag gagaccaagc ccggacagca gaccccgggc cctccccacc ccgccccgcc  15180
tctgactcgg acaccagcct tctcagaccc cgggcactcg gccaccccgc cctgccccta  15240
cccttggcct cctccaccct cccctcatcc ctccgccgac cccaggccca ctccgactcg  15300
gacccccacc ccagtcctct ccgcccgacc gccacggccc accagcctgt gccgctcacc  15360
tggatctctg gaaaaagctg aaggaagaca catcgtatgc ggctttgagc agcaccacct  15420
tggcctcgcc tttgtagagg acgctgaggc tgtacagctt catggctccg cgccctcagg  15480
ccgcccgcct gcccagctgc gggacccgtt ctcagggagc agcgcggccg ccgcccctcg  15540
ggaccgccgc cgcctaccgg cctctcagca gccggctgct gacggggcca ccgccggctt  15600
cctcctcctg gctcgcaatc cacttccgga tccggtcagc ctggttgagg gttctcatac  15660
tccggatgca gaaatgtgag cccggaagta caatgcagcg aggggcggga tgccacgcct  15720
cgcgtaagct tggcccctcc ctgctcgcca ggtggagtcg ggcgcgcggc gggataccgt  15780
actgtcttgt gctgggtggt gctgggcctc ccacagcggc ctgaaccctt cttttttttt  15840
tttttctttt ctttcttttt ttaaagtaag catttttttt attattatac tttaagtttt  15900
agggtacatg tgcacaacgt gcaggtttgt tacatatgta tacatgtgcc atgttggtgt  15960
gctgcaccca ttaactcgtc atttagcatt aagtatatct cctaatgcta tccctccccc  16020
```

-continued

```
ctccccccac cccacaacag tccccggtgt gtgatgttcg ccttcctgtg tccatgtgtt  16080
cttattgttc aattcccacc tatgagtgag aacatgcggt gtttggtttt ttgtccttgc  16140
aatagtttgc tgagaatgat ggtttccagc ttcatccatg tccctacaaa ggacatgaac  16200
tcatcatttt ttatggctgc atagtattcc atggtgtata tgtgccacat tttaggagga  16260
gcttgtacca ttccttctga aactattcca atcaaaagaa aaagagagaa tcctccctaa  16320
ctcattttat gaggccagca tcatcctgat accaaagggt ggcagagaga gacacaacaa  16380
aaaaagaatt ttagaccaat atccttgatg aacattgaag caaaaatcct cagtaaaata  16440
ctggcaaacc gaatccagca acacatcaaa aagcttatcc accatgatca agtgggcttc  16500
atccctggga tgcaaggctg gttcaacata cgaaaatcag taaacgtaat ccagcatata  16560
aacagaacca aagacaaaaa ccacatgatt atctcaatag atgcagaaaa ggcctttgac  16620
aaaattcaac aaccctcatg ctaaaaactc tcaataaatt aggtattgat gggacgtatc  16680
tcaaaataat aagagctatc tatgacaaac ccacagccaa tatcatactg aatggacaaa  16740
aactggaagc attccctttg aaaactggca caagactggg atgccctctc tcaccactcc  16800
ttttcaacat agtgttggaa gttctggcca gggcaatcag gtaggagaag gaaataaagg  16860
gtattcaatt aagaaaagag gaagtcaaat tgtccctgtt tgcagatgac atgattgtat  16920
atctagaaaa ccccatcgtc tcagcccaaa atctccttaa gctgataagc aacttcagca  16980
aagtctcagg atacaaaatc aatgtgcaaa aatcacaagc agtcttatac accaataaca  17040
gacagagagc caaatcatga gtgaactccc attcacaatt gcttcaaaga gaataaaata  17100
cctaggaatc caacttacaa gggatgtgaa ggacctcttc aaggagaact acaaacgact  17160
gctcaatgaa ataaaagagg atacaaacaa atggaagaac attccatgct catgggtagg  17220
aagaatcagt atcgtgaaaa tggccatact gcccaaggta atttatagat tcaatgccat  17280
ccctatcaag ctaccaatga ctttcttcac agaattggaa aaaactaaag ttcatatgga  17340
accaaaaaag agcccgcatt gccaagtcaa tcctaagcca aaagaacaaa gctggaggca  17400
tcacactacc tgacttctaa ctatactaca aggctacagt aaccaaaaca gcatgctact  17460
ggtaccaaaa cagagatata gagcaatgga acagaacaga gccctcagaa ataatgccgc  17520
atatctacaa gcatctgatc tttgacaaac ctgacaaaaa caagcaatgg ggaaaggatt  17580
ccctatttaa taaatggtgc tgggaaaact ggctagccat atgtagaaag ctgaaactgg  17640
atcccttcct tacaccttat acaaaaatta attcaagatg gattaaagac ttacatgtta  17700
gacctaaaac cataaaaacc ctagaagaaa acctaggcaa taccattcag gacataggca  17760
tgggcaagga cttcatgtct aaaacaccaa aagcaatggc aacaaaagcc aaaattgaca  17820
aatgggatct aattaaacta aagagcttct gcacagcaaa agaaactacc atcagagtga  17880
acaggcaacc tacagaatgg gagaaaattt ttgcaaccta ctcatctgac aaagggctaa  17940
tatccagaat ctacaatgaa ctcaaacaaa tttacaagaa aaaaacaaac aaccccatca  18000
acaaatgggc gaaggatatg aacagacact tctcaaaaga agacatttat gtagccaaaa  18060
aacacatgaa aaaatgctca tcatcactgg ccatcagaga aatgcaaatc aaaaccacaa  18120
tgagatacca tctcacacca gttagaatgg tgatcattaa aaagtcagga aacaacaggt  18180
gctggagagg atgtggagaa ataggaacac ttttacactg ttcgtgggac tgtaaactag  18240
ttcaaccatt gtggaagtca gtgtggcgat tcctcaggga tctagaactg gaaataccat  18300
ttgacccagc catcccatta ctaggtatat acccaaagga ttataaatca tgctgctata  18360
```

-continued

```
aggacacatg cacacgtatg tttattgtgg cactgttcac aatagcaaag acttggaacc  18420
aacccaaatg aacccttctt tttgcttgcg ttgttgaaag aaggcaagtc tatggatagg  18480
aatgagtgag gcacagctcc ctgaggatgc catatcttgc ccgtttcttg tgtattaagt  18540
gacatcacgt gttaccaaac taaaccggct gcatttgcct gcgcacaaca taaaaccaaa  18600
cacccaagca ttggattttt gtagcaagaa agatgtattg ccaagcagcc ttgcaagggg  18660
acagaagacg ggctcaaatc tgtctcccaa tacttgcttc gcagcagtag atttaaggga  18720
gagattttgg aagtggagtt tcgggctgga cggtgattgg ctgaaacgaa gaagtgttta  18780
gaaaatctct tggtcatgag ctgttgcttc ttcatgctgc ttcaagggtc acatgcagat  18840
tcaggaggtg gtataaaaca agctgtggga atttgggctg tgacatcaaa gggccgctcc  18900
tcgggctagt aagtctattt tgcacaggct ccagtcagcc atattggttc caacctgttc  18960
cagcaagttg tataagcaga ggggattata gcaaactgtt tccttatcgg ctgccctgca  19020
agacaagctc aagatttctg ttagttacca gtttctttaa ccctgtcggg cacagtttca  19080
catgtaatca gaaaggaact tgcaagacac atacaactga aagaaacttg gtctttggaa  19140
gttgtcagta aggtcacaaa gttgtgatgc tagaagcagc cgtatctgag attatgggaa  19200
agagatgata tattggaaaa acaacagcat cactttaaac attactctaa atcaaggttt  19260
ctcaaccttg gcactattga cattttgggt tagatagttc tttcttgttg ggagactgcc  19320
ctgtacattg tgtaggcagc atctcaggcc tttgtagaaa tgtcagtacc aacccacccc  19380
ctccccactg cacaatcaaa aacgtcaaaa tgtcctttgg gagcagtagt tttgagaaac  19440
attgctttgc agatatatat gtttgtttgt ttgttttgct ttgtgacagg gtcttactct  19500
gttgcccagg cagaagtgca atggtgtgat cccactcact gcaacctctg cctcccaggt  19560
tcaagcgatt ctcatgcctc agcctcccga gtagctggga ttacaggaat gcatccatac  19620
acgcggctaa tttttgtatt tttaatagag atgggatttc accatgttgg ccaggctggt  19680
ctgaaactcc tggcctcatg tgatccaccc acctcgacct cccaaattgc tgggattaca  19740
agcttaagcc actgcgccca gctgagaaac attgctttaa ataatctgtg gtgaaaggaa  19800
gttcccacca cctgcccact cactcagtac ctctgtcacc aaccctcttc cctgggtgtt  19860
tccaagtaca gagggtggaa agggcttttc cacatttccc ctgttttggt agtaaacatt  19920
aggaacagcc attggccgtg gctaggctca gccacccaca gatatggaca cagtagtctg  19980
acaagctggg ttgctgggtg ctatcagtcc aggctcaact gcttgcactg acaccatttc  20040
cctataggag gcaggtgaga gccatttctg aggaaagtct ctggagcccc tcttccttcc  20100
actgaaagtt gtgcaaaaag atcaggaaga cagcgcttgg atggaataaa tttcagtgta  20160
tccacttgac acattatagt ggctgtccca aagtttacct tatgccaagt actttccatg  20220
tgccacatca tttaatcctc acaaaaacag gggaaaatat tattgccacc ctacagacat  20280
agagactgag attcaattta aggagatggt tggtaaggga cagagttggg gttcagatgt  20340
caacagtgaa atgcttaaca aactgtcatg cagcccactc ctggcaactc ttcctgctcc  20400
tctctggcct cactcagcct ctactgttcc aggaagcctc attcatagtc atgtggttgc  20460
agacttccca agctcactgt gttaccaaaa agcaagacct gccttctgct gcatcgcccc  20520
agctgtcacc caacttggat tcagtcccag cactgacaca tcacaaaatc acaaaagtga  20580
gcaaaccatt acctccctga gtctcctttt gtttttatct ataaaactag aaaaatattc  20640
tttccatagg aatgttgttg gaaataataa aacattatat tacaagctct agtcattgtt  20700
gatgtttaac aggtaacagt gataattatt tgtcttctca ttaatgaaga aaaggattat  20760
```

```
taatcataga gggtggaagg catctatggg aagtagagat ttgaagatag gctaaaaccc  20820
aagtaaggcc tctagattag ataatagtat tgtatctatt ttaatttcct gctttccatc  20880
actgtgccat ggttatataa gagaagtctt tgtttatagg aaatatacac aagaatttag  20940
aagtaaaggg acattgtgtc tgcaacttac tcttacaggg tgtgtgtgtg tgtgtgtgtg  21000
tgtgtgtgtg agagagagag agagacagag agagagagag acagagagaa agagaatgat  21060
aaagcaaata caggaatcag gatgaagcgt atctgtttgt ttgttttgct ttgtgatagg  21120
gtcttgctct gttgcccagg caggagtgca atggtgtgat cccgctcact gcaacctctg  21180
cctcccaggt tcaagcgatt ctcatgcttg tattgttctt gcacctgttc tgcaagtaca  21240
acattgtggg aatggaaaat gcaggaaatg ggcagtaagg ctatgaacga agcccgcaca  21300
ggagtgtggg tagcagagtt ctctagtcca ggctcccacc tgaggtgctg ggacctagaa  21360
gaaaagcctc tctgcagaca gaactggagt taacgctgtc cacgataaat ggcccaggcc  21420
ctgttaagtt tgccccattg agcaaaaacaa gtacccaccc gcctttgcag ccttgcctag  21480
ctcacataag gtgccagccc ttgctgtaca gcagaacctt tggggagctg gacaaaagcc  21540
tatcaaggag catacccccca ggaagcccag tccaggtggg gagcccagcc acacaatggc  21600
ccttgccccc acacctcctc attcagtcag ctaaggccat ggcagctgag ctgcctccac  21660
agctcatata ggaaaagggt gtggaaaggg gccaccaatg tggtcaggcc tccatggcct  21720
gagtaggtca ccaagcctca ggtgcacaga cttgatgtca tcaatcaggg tctgtcagca  21780
cacctagccc tcaggaacac tgctccccac tgcaacccca caccaaggca tcctgggctc  21840
cctctgggtt ctccaggccc cagggaagac agacagagtc tgccaccaaa ggtttgagct  21900
ctgccactgg ctacgaagca ataggggatg tcagagcaag ggaggaacag gacaggagta  21960
tacgtgggca ggaagggatt acagccaagg aagacaggag gcaggtgccc tgattttgag  22020
gctgtgcccc agcaggggct tcccagaagc tgtatttgtc ctaagacacc cctctgcagc  22080
tgaggggcta gagatggata tgtagctgtg ttaggccatt cttgcattgc tataaagaaa  22140
tacctgagac caggtaattt ataaagaaaa gaggtttcat tggttcacag ttctgctggc  22200
tttgcaagag gcatggtgct ggcatctgct cagcctttga ggaggcctca ggaaacttac  22260
agtcatggcg gaaggcaaag gggaagcagg cacatcacac agtggaagca ggagtgagag  22320
agagagaggc actgggaggt gccacacttt taaacaacca gatctcgtgt gaactcagag  22380
caagagctga ctcatcacca aggggatggc ccaagccatt catgagggat ccaccccccat  22440
gactcagaca cctcccacca ggccccacct ccaatattgg ggattacaat tcagatgaga  22500
tttggtgggg acacatatcc aaaccatatc agttatcagt agccatactg gatgaatgcc  22560
aggaacttag aattaggaca catggtcatt taggcaagtg gcttgtcctg tcaatggtac  22620
cctgatagtc gtggggttgc cccgtacaaa aagcgagagg aagtctacag agctgtcaaa  22680
gaggggcagg tggaaaggcc tgcagaggag tcccctgctc cacaaccagg cgtgcacctc  22740
ccacatcctc ggggctgtag gccccacatg agagcagaaa gaaggatgca gaggaaggcc  22800
aagaacacaa ggtgtgccct tggaaaggct gggcacacca aacacaacct aataaacaac  22860
agcaatgagc acacagggaa agtactcaca gggaaaccat catgaactag aggctgatcc  22920
cacaccctgc cacatggggc cccaggcccc agcctatcaa ccagtggtcc ttattgccac  22980
agcgattggt ctttggatag gcacctgatg caagcttcag ccaatcaaca ggccactcag  23040
ctggccatca gtaggccatc caatcagagc aaagcccagg actttcttcg actcttaaga  23100
```

-continued

```
aaagagaagc aaagtaactg gcacagattg gagaggatca aggaaccccg agctggatac  23160
atacaaactt tgggttaaca tggatgatta aatacatatg tttatgtgaa ccacctccca  23220
aatatgctcc actataatga cacaagacaa agggcagggg gagaccaatt gcaaggtggc  23280
gcaaatgaga gatgctacca agggtggcgg gggagagagg ggagcagttg tcaagttagg  23340
aggcaacagg ctgagggaca gggaccagca gacggggagg gaggggctga agcagaagtg  23400
tccagtgtct ggagggatgg ggccagaaag gcaaggggca tcctgaagaa gctatacctg  23460
gggagggcag ctctctcccc acctgctccc caattcatca gccaggaatg ccccatccac  23520
cccaccccag ggaggaggac agaggacttt cgtttgggag cattgaatgg ttcagagatt  23580
ctgcaactct gcggtcccca actaaactgc tcattgtttc aagcagtccc tgttgggtaa  23640
atgtccccca ttgtaaccgg actcggattc caccgcttga aagccaaata caagaggaga  23700
ggtttggtgg gaggaaaagt ggttttaact agagccagca aaccaagaag atggtgaatt  23760
gttgttttaa agcattcaat tatctcaaat tttaaaattt atcataggat tctgaaagga  23820
aaacttggta tgggacatac gtgggagcag tgcagggtac agggtctatg tgtcttgatc  23880
caatggctgt cttgagtatc acctatcctg aggtctggtt ggtgttatct ttccttcggc  23940
cagatggtgg tgggtgaatt gtttcgactc cccctaagtt ggaggattcc gcaggggttc  24000
cgtgtctggt ttttgtttca agattagccc ctggaattcc caaataagca tagagttaga  24060
taagcgggca tggtgcaaag gagtgtctag tgggaaaggg agagaagcag agtttcaaag  24120
tacatttcaa ggttacattt taagactaaa gaaaaagcct taaaatgcat ttttaaagct  24180
gatttaatgc ttggctacac taggctgtgg ccagtgtgca gtgtggctgc tcttggatca  24240
ggtgatgttt catcagctgt gtccagggag ggcagggcca tgtggcagaa cctgggacct  24300
ctgtgtgagg gactaccttg gcccctgtcc ttagcaggaa gctatggtaa ggaaccctta  24360
gggagacatt aaattgggga gaccgtccct gccaatcctt taacctcccc agcctcagcg  24420
acctcagttg gaaagtggtg gtaataatac taccactgac caggtgtggt ggccagacat  24480
tccacacttt ggcttcagcc gctccctccc cactctactg taatcccagc actttgggag  24540
gaagaggtag gcggaacctg aggtctggag ttgagaccag cctggtcaac atggtgaaac  24600
cccatatcta ctaaaaagaa agtacaaaaa attagccagg tgcagtggca cacgtgtgtg  24660
gtcccagcta ctcgtgggtc tgaggcatga aaattgtttg agcctgggag gcagaggttc  24720
cattgagtgg agatcgagcc actgcactcc agcctgggtg atagaacgag attctgtctc  24780
aaaaaaataa aaataaaata ataataataa taccactgcc tgccacacta agattgtctg  24840
attagatgac agaatgaatg caaaagtact ttgtgaatca taaatgtttt catcaatatt  24900
agttataatg acaattgctc cttctcctaa taaatgtatt gcctttcttt aggaataaat  24960
ataacaagaa atgtgtaaga tatatatgag aaaaataata aaattcacct gaaggacata  25020
aaagaagacc aaaataaatg aaacaacaca tacttctaga tgagaaaact caatattata  25080
aagaggttag ttctctaaaa tgaatcccta aacccacaaa gtcaatgtat ttccaatgaa  25140
attgtcaaca gcattatttt ccgaagtggg atgagtagtg ctaagattta taagaaagcc  25200
aacattccag agcagtgggg aagggattgc ttcaccacca aatagccata ttagagattc  25260
ccttgcacca tacccaaacc accatctccc aggacccggg agagcagaaa agaggaatga  25320
gaagaaaggc gaggatgtga ggtgtgccct cataatggcg gtgcacgcag cacaagcaat  25380
tgcagaaaga ctaaagtact gaacaaatag aaaacttgga aaaatattag aaggaaatgt  25440
gggagaacat ttttgcaatt tggggattgg aaacggtttt cttaacaaga tataaaaacc  25500
```

-continued

```
ccaaaacaag aaaacaaagg ttgaaattca taaaaactag atacttctgt atgatgaaag  25560
acacgattaa tcaagttgtt aagtttagca atagactagg ggagatatca tagtatattt  25620
aacagacaaa ggattaatag atactacaga tgaaatataa aatagtttct ccaagtccat  25680
aggcagaaga taatccaata gcaacatagt taagtaatgt aaacaaatca tccttagaag  25740
aagaaatgca atcaccaaga aacacatgaa aaggtgtcca gcattttgca attcaagcaa  25800
caatgaggtg acagatcggc aaaaaactca taaagattta tcatctgaag gattggccaa  25860
gataaagcca aacttctcgt gttggcagaa gaaactggtg aagccatgtg aagaggccac  25920
gtggtcctgc ctaccaagat gtaaaatgtg tacagcattt gaactagcaa ttcagcctcc  25980
aggagccatc cagaagaaac actgacacac acttagactc cggtgaaatt caaggacttc  26040
tgccacagcc tgcttcgtaa tagtgaaaat ctgaaactgc ctcaatgacc gtcaatagga  26100
agttgatttt aaagtgttac agcacatctg tctggagaga tcgcactggc cactcctcct  26160
cacccctct gctggacctc tgagcgtagg tggcctggag ctgggtcctg agccctcttt  26220
ggtctatacc gacactaccc aatatggtag ccaccagtca cgctggacac ttgaaaagtg  26280
gccgatcctg actgagaagg gccacgagtg ggaaaaacac accagacctc agtgacttag  26340
gcagaagtat gttttgttcc agactattga ctgagcccgc agctgagttg gctccagcac  26400
cctggccccc tgctccatcc actcactggg actccccact gcacagggca acctctccag  26460
gggcacttgg gctgcgaagg ggagagtggg tggcatccca ggctgaagct tcctgagcag  26520
ggccagagga ggagccagtc cctgtgggcc tctgttctga cagtgtcaac ctcagccagg  26580
cttgtgtggg ccaggtgtac tgttctggtt cagatttcaa ggagatagtc agggcaggcc  26640
gcgccaaagc cctccgatgg gctcccctac tgcctggcag acctgtccag ctttggactc  26700
tggccctgcg acctggaagt caggctgcca agaggtccag gcagtggcct ccactgtgga  26760
gggtctctgg agagtttaca gccctagata ggggggttag ggatgtgaga tggtcccagg  26820
ggcctgctcc tgagccacgc caagctgcct gctccctttc ctctgcttcc agactcacgg  26880
gatcctctgc tcatcagaac aggagtgtgg gagaccctga gacactgccc caggatctga  26940
acaggtggca aaggcttaac aggctagcgg tcactgtagt gacaaggcga ttgagtggtc  27000
accatggtga tggggatgga ggctctttgc caccagtccc agttttatgc atggcagctc  27060
taatgacagg atggtcagcc ctgctgaggc cactcctggt caccatgaca accacaggcc  27120
ctctcaggag cacagtaagc cctggcagga gaatccccca ctccacacct ggctggagca  27180
ggaaatgccg agcggcgcct gagccccagg gaagcaggct aggatgtgag agacacagtc  27240
acctgcagcc taattactca aaagctgtcc ccaggtcaca gaagggagag gacatttccc  27300
actgaatctg tctgaaggac actaagcccc acagctcaac acaaccagga gagaaagcgc  27360
tgaggacgcc acccaagcgc ccagcaatgg ccctgcctgg agaacatcca ggctcagtga  27420
ggaagggtcc agaagggaat gcttgccgac tcgttggaga acaatgaaaa ggaggaaact  27480
gtgactgaac ctcaaacccc aaaccagccc gaggagaacc acattctccc agggacccag  27540
ggcgggccgt gacccctgcg gcggagaagc cttggatatt tccacttcag aagcctactg  27600
gggaaggctg aggggtccca gctccccacg ctggctgctg tgcagatgct ggacgacaga  27660
gccaggatgg aggccgccaa gaaggagaag gtatctcgcc ctccattggg cattctggga  27720
gtgtttgctt gcctgtcccc aacattccat ggtttgtttg agcctcagaa tctgatttta  27780
tgcacaggct ctttgagaag ggtcttgcca ggggtgcctt ctggggcagg aaggccccta  27840
```

-continued

```
ctgcctggca gacccatcca gctttggact ctggtcctgc gacccggaag tcaggctgcc  27900
aagaggtcca ggcagtggcc tccactgggg aggggctctg gagagtttag agccctagat  27960
gtgggggtta gggacatgag gtcttgtgga caaagcccac tacctgattt tgagacaaca  28020
ctcactagac atggtgacaa gtcaaagatg ccttgcctcc taccaggaat cacttcgcag  28080
ggagcccgag ggctgctgtg gcctgctgag gagtgcaggg cagttacttt ttccaaaaac  28140
aaagagaaat ccaggcatgc tctgagccag ccctgagccc agcagtgagc aaggagagag  28200
ctggagacag gggactttgc tgtgaaacac tggggggaat gtgcctgcat caccccagct  28260
gggggcccag gcagagtggg ggagaagggg taagtgggca gagccagtca ctttgggcat  28320
gcttccctct cgcctctgtg tgaaatgacc aggtcagcat aaaccccggg ctggctgtgc  28380
ttctggcaga gctaatgatg ttaggaggaa aacaaccaac ccaagtgaga gggtgcgcag  28440
ccagacagct ggaccggccg aggccccaac caagtcccag atctgcctgt cactggtgct  28500
atggcagcaa tttggatgag aaatcctgcc caaagggccc cttcaggcca cccggggaga  28560
aggaagcggc tgtctttggc atgaccagaa agatggctcg gagctaggga gaggtggaca  28620
tgtgggctgt ggagatctgg cactttcccc aaacaaggag agaaagcata gtgtgcctat  28680
gtgtgaatgt gctatgtgtg catgtttgtg cctgtgcata cctgcatgtg tacatgcatg  28740
tgcacatatg tgtgcacagg gaatcacttt aataaaggcc acagcagagc tgtccctgag  28800
ccccttgcat tcacagtggc atgtgagtga accaccttct taggctgggc atccagtctc  28860
agactctggg gctgcccatg ccccatcctt tatctgctcc acgtgtgagg ggttgctggt  28920
cctgaccagg gccagctgtg aaccccagaa tcctgggaag tcactgacat tcttgtcagg  28980
gccaagagtg gagcaaggca atgcctcggg cacaaacttt aaggggtcac cagaaacatc  29040
aatcatcaag atatatgcta ttttaaataa tcaaaatgaa tgcaaaaaaa atttatgatg  29100
gacaacatac caaattctaa acaaaggcag gatgagtatc actggcttct gcacttttct  29160
ccacccagtc tacccctctt ctagtgcctg gatcgcaggg tgccaaggcc tggatgaggg  29220
aagcgtggag ctgcaatggc cactcctgtc tgcctgttct ggctgcacag aggactcagt  29280
ccttgtcttg gggaaccta tcttggtttt agggtcatcc taaggatctg atgttttcca  29340
agtgagctgg ctgtccaggc ccacccaggt tcagtccagt cctgtgtctc tgggaagtgc  29400
tgcccctacc ccaagccagt gtttgacctt ggagcaatga gcaatgccct ccttccactt  29460
tcaaagttgt ccccaagacg tcagctgtgg ttgtctctgt gcagacaccg aggaggaact  29520
gtcttctttc tccttttggt tgctttggag gaaagtaaag tgttgctggt ttccctcttt  29580
ctacttcttt gattgagagc agccgtcttg ccggtaccaa ccttccagat cttacctgtg  29640
gttgcaggag cctgtggcct cagtcctgtg cccagtgact tctccatgtg gatgtcagct  29700
ccttaggggc aagcctgatt ccactgacac tactcccacc cctcataagc cccttcttac  29760
cagctgcagt tgcctggtac cccaccatcg ctgactcatt cctttggcat caaggttcat  29820
cccttactgg gccaccactt ctgggtggcc tgaaataggg ccctgggcat ccctcttggg  29880
gaccttttgg tctatatttt cactctcacc tcactaagga cagatgagta aatctggtta  29940
actttgcctg atagatttgg tgaccttttt tcaggaagga gcctggaaag atgagattca  30000
ggtgtattgg tcagcttaga ctgccataag agaataccat ccactgatgg cttagaaaca  30060
acagaaatct atttctcact attctagagg ctggacgtcc aagatcagat gccagcatgg  30120
tcaggttgca gggagggctc tcttcctgac ttgcagaccg ccaccttctt gctgtgtcct  30180
cacatcgtgg agagagagtg aaaacaagct ctctggtgtc tcttcttata agaatgctaa  30240
```

-continued

```
tcctatgatg ggggctcccc ctccttacct catctaaacc taattatctc ccaaaggtct  30300
catctccaga taccatcaca ctggggttag ggctttgaca tatgaatctg gggggacaca  30360
attcaatctg taacaccagg agggcatgcc gggaggaact gaccttcctc cctccagctg  30420
ccctggacac ctttgcccca ttgaaggagc aggctcagaa gtggaatgag gatggaataa  30480
ggtgcactcc atcatgctta cccacatccc tggcaggaat tgtcctgggc cccagcagga  30540
gagatgcccc cccatactgc catggcacct gctctgagac aggtgtgcag agtgcaaagc  30600
tccaggtggc ccccaagcag gtgtgctggg aggaggggcc cgtgtgggag gagcaggcag  30660
cgccaaggcc tagcggagca gtgacaggtc cctgacttca gggaatgggc acgctgtggg  30720
caggcagctg gtgtgggggt gagggctggg gctgcatctg tgggaccagg gctgggccat  30780
ccatcatatg ccgtgtcaca accccagtgc ccctgctgta gccaggacag gaggctgggc  30840
caggctggga ggtgacaaga gtgggggctg tccccaggag aagcactctg ctgcctgtgc  30900
ccaggcctct ggggatgagg acccctcaga aggagtagct atgtctagga agccccaggg  30960
caggagcaag ccaaagggga catcattagt gagatccagg ggatcagtgg gccacagaag  31020
ccccagcgtg agcccctctg actgatgcag ctaggcccac acctgcacct gcccacagca  31080
agaccccccag gaggagaggg gacagatgga gagaggcaca aagtgcccct ggcctctgcc  31140
ttgaagccac cccaaggcaa gagagatttg agcccctgtt tagtgacctc caggggaaca  31200
ttctggccca tctgatgtgg gaagcccctt gtggagtctg tcattcctca gctgagccag  31260
gcctttggag gcagcccagg catgtcccct gtgtgctcct atccctgtgt tgggacacct  31320
ggcccagccc ctccttctgc ctttctcttc ccttcccttc tcaggagtgg acacttcctc  31380
ctttagcccc ctcacagctg tgtgaacttc tctgtatctc tctctttctg tctctttctc  31440
cccctctctc tctgtctcat tgtctctctg tgtgtctgtc tgtagtattc tctctctgtc  31500
tctgtcactc tgtctctctc tctctctgtg tctacctttc tgtatttcgc tttgtttctt  31560
tttctctgtg tgtgtgtgtg tgtatctgtt tttctcactc tctctctgtg tctatctttc  31620
tgtatttcgc tttgtttctt tttctgtgtg tgtgtgtgtg tatatctgtt tttctcactc  31680
tctcaatctc tctctctctt tctgtctctc ttttgctggc ctgagcaaag agggagcccc  31740
atcctgatgc tacataaccg tgaaccagca cagacagaat tgtaggaaag tcctgcaagt  31800
agaaggatag aaggatgagg gaagaaacgc catgtgagtc atgacagatc cctttccagg  31860
agccactgac tcaccctgcc tcctgccctc ccactgtgac actattactc acagacaggc  31920
ccggattaaa cctatgttcc aggtgccctg tggttcccac agtgtggctc cctgggtctg  31980
gcctcaggct ccacaggtgc ccagccctgc caaagtctcc agagcagctg tccagctggg  32040
gagctgcggg gccccttcac agagcgcatg ggaagaagtt ccatcctaca cattacatcg  32100
agagggacgt gcctgagaag gggagctgga gcccgtgcag ccccctgctt gcgtgcagaa  32160
catagtgtac cctgagcatg ccatgaaaaa cacaaacgca caaagttgta aagaaaaaag  32220
aaatgacagg tggctgtaaa atcagttata gcccacgaga ggcccactaa tgagtggtga  32280
tttcagctga ttacaaagaa atgatggtgt ttctgtaatg aactaaacat gcactcgtgc  32340
gtgcacacac gcgcacgtat agtcacataa ctgaccagcc ctatgcatca cttgttaatt  32400
acttagtaac tgtaacaata atagtttcca ataagtgagc cttagtctct gcgcaagggt  32460
cagtttattg agcacacggg ggccttgcag tgggggcagg tgatctgctc ctgggagccg  32520
ccagcctctc ctctcctgct cttcatcttc ctccgtggtg ggaaattgtc tcactgcttc  32580
```

-continued

```
tacacctgag gctgaacatc tccctttatt tcagtctgaa acacatgtaa aaatatactg  32640
gaatgaatta aggttgcaat tattgatatc aggcagtgag tacatcaggg tttattatac  32700
tatctccttt acttacttcg aagttctcta ttaccaaaaa attaaaaact ataaaagaaa  32760
gaaaaaggaa atgaggctag attcaacaca gattactctt accaaaccct tcgtagtccc  32820
aggagtcccc taacacaagc acttgtgacc tggagtgata ttcacagcat tccttacctg  32880
gcaatacctg agtattagcc cccccagtgg gatctttgtt gtagacaacc agcaactatc  32940
agcccagcca ataaacaagt aggaaagggg agtgctggag aggccaagaa gtgggatttt  33000
ccatgctcct gggctgtgat ccagagggca cggctgtgag gctgatctca atgaacactc  33060
tgtcttggaa gtacagggat cctctgctac ctgaaaacgt tctgagtatt cactttcatg  33120
gattgcaaag tcatttaccc aaaattcact ctccaaatga aaagtgagta tgatgaatca  33180
gtattcaagt tccacctggg tcctgggaga gggcatggac atcatatccc agctgttccg  33240
acaggaggac ccaatctgag tctcactgcc tgcctgcatc gtttgtctgc tgccagcctg  33300
cacagtagga agggaaaaca tgatttgtat ctgttttagg tcaggttccc aagaagtaga  33360
gcctgagatt ggaattcttg gaaaatggtg tttgcgggag cgctgtcagc agaagctata  33420
aggaagttgg ggggacagaa aacgagaggt aagaagccag tcaaaaaggc aggtccagct  33480
taagtccgcc tcagtctggt tccacaaggg ctctgatgca tgaagaatat cacagggttg  33540
tccctcctgg gagaggggcc agcctattgt acctgtatca aagccaccag ctgagggcca  33600
gtggggaggg aagatcttcc aggcatttcc aggaaactct caggagaagg gtgtagctgt  33660
gagcagtctg cagctgctgc tcactgcggc taaaggctgg gtgtgcaggc cagtcagcca  33720
gtgaggtgcc aacagcaggc actacagtcc acccccttgac tgctcagacc tactgctttc  33780
cactttaagc tctctccatc caggcacagc ttcagggaaa acttacaatt ggagaaacag  33840
agggatgaac tacaatgccc acttctgcat gtgattgtaa gactgtcact gatactcacc  33900
atcatgcccc atccccacca tccattctag tgtccccttc cccttggcta acactgctgg  33960
tctaggtgac ttccctagag caggagccaa acccttatcc ctgaggcatc tgaatcctgg  34020
attcctttat caggctattg ttgttgtaag ttgtccattc ccaattacaa ctggacatga  34080
gactaccaag aaacaccctg gcaaatcatc tgagtgcaag ccatattctt cctgctccat  34140
tatgtagcgg tagtcctacc tcctaatgac aagggtaaat tgccacattt tgctccttgt  34200
gccaggatgg taatacccttt ctctacctgc ttggctactg gcacaaggaa gcacagcatg  34260
accaggaggc aattgtagct gtacatttag tgaatgtgtt aatgtatcac ctggtggaag  34320
gaccccctct gagaaccagg acttctagac ccacaaaacc taaagttgtg aatggcggaa  34380
gcacaaattt cccaagtgga tcatggagag tgatgaagag ttcttggttc ccaaacccac  34440
atattttacc tttcaggaac atggcctcat cccatagcca ttagagtgca tattgcattc  34500
tggaggagac tgggccctcc tcatgggtgt catcttcaag atgacagctc cactgtgcct  34560
ccaagaggat gctccaccac cctatctgtg attccttggt tagcaggaca ggctgctgca  34620
ctgagggtag gaaaggcaag tccattgatg gctggaatac atgtcaatcc aagtcaagag  34680
aaaatgccgc cctttccagg ttggaagggg cccgatttag ccaacttgtc acccagtagt  34740
ggctggttgg tctcctccag gagcagtgtt ataccaggaa ttcagcacca gtcgctattg  34800
ctggcagttc ttacattcaa cagcagcaaa actaggtcag ccttgatgag agggaatgta  34860
tgcttctggg cacaggcatg gcttccttct ctgactccat gactatctat ttctgagtgc  34920
atggtggccg acattcagct gcctgcccat cctatccact tggttattat tgcctcttcc  34980
```

-continued

```
acaagaagtg gtttctggct gtcattaatg tctcatactt tgtgcccact cacacaggtt  35040
tagctctaca acttttcccc atgccaccac ttttccacaa tcttctaatg ttgctccttc  35100
caagctactg aagaacgagc taagctattc accaatgtcc atgagtctat atttacctta  35160
ggccacatct ctctccacac aaagtgaata agcaggtgca ccctccaaaa ctctactaag  35220
aggatttctt ctccccagtg tctttcaggg ccaccttgag tggggctgaa gtacagcaga  35280
agtccatttc cagcttgcat caacattcca aactaaccta tccatgatca atgcatagat  35340
gggtttttcc ctcctccagc agctagacaa aagacacccc ccaccaggag gccatatttg  35400
catgtgggtg aaagagaggc acaggggcca atattcgtgc aacagtggta gatggcaggt  35460
gggtctgggc cacctgtccc tgcagcttat ctgtgccatc tggacctgct caagcctgat  35520
tccagatata ccatttccat cttatgatgg atggcttatg acctagtggg tctgacagca  35580
ccaaactcat aatgggcagt tatggccaca tggtcactta atgtcctatg gtcagacact  35640
ctgctgagtg gcatgccagg aaatgcttta caagtggtgt ttggttctct gctgcagatg  35700
gcatgacctt ggtccggagc cctaggggtt tggacagtga ctcctgttgg ggcctaatct  35760
cacattccat gcagagtatc atcagatttg ccaatcacat agcctaaggg tcaggactga  35820
tccaaccagt tttgcagag atcaaactgg agaatgaaag gttgatatga tgtgaccatc  35880
atatcacgtt tttctctctt gaaaagtatg cagatgtctg aaagagacaa gtgccccagg  35940
agaaaatgca tgccttcctc aggatcggcc cccacctccc ctcctggcca caaggagggt  36000
caaatctcag catggcccaa cttggacctg tcaaggaaga agaaaaaaat tgtatgccaa  36060
aggaactcag tctttggcta acaagtacta gacatccttt aagtctttga gaatggtaat  36120
aatttctgcc atccctccag atttgtgttt ttctgttttg gctgggtggg aatgcagcat  36180
tttcactttg cctttgttat tacaaatgtt gcttattcta taaatcaagg aaccattgta  36240
agggctcttc tgatggttaa gtatatccat tccaatgatt tattcgggat ccaaggaaat  36300
gatttctggg tgaatacaca gaactagtgg atccaatttg agacatacct gggccagaac  36360
tatatttgtc gtcttacccc aataagcctg cactctacta ggacagccat gacagcactt  36420
tgggacccta gatataagtg tgaattgctg gctgggcatg gtggctcacg cctgtaatcc  36480
cagcattttg ggaggctgag gcaggtagat cacctgaggt caggagttga agaccagcct  36540
ggccaacacg gtgaaacccc atctctacta aaaaatacaa aaattagctg ggcgtggtgg  36600
tgggtgcctg taatcccagc tactcgggag gctgaggcag ggagaattgc ttgaacccag  36660
gaggcggagg ttgcagtgag ccaaaatcac accactgcac tccagcctgg gtgacagagc  36720
gagattccat ctcaaaaaaa gaaaaaaaaa agtgtgaatt gctatgaaat cactatcaaa  36780
agatctgagt gttaccctta ctcagtgtgg tcgaatataa atagccatag gttcctgtta  36840
tacacacttg ctgtggtgct acagagtctt tcctcatggg aacccagtcc ctctttcagt  36900
caatgggttc tggttcgaga actggctgag gtttggaaac tgtgcctttc catcataact  36960
ttccactggg gtgactgacc ttggccttct gttcatcctt tctagcccct aagaatccaa  37020
cactctatta gccttctcct tagaccccta taagctaatc ccttctagtt gttagtctga  37080
ccttggtgcc caatatgata attattccca ctttgcttct gatatgcttc taagtgctgc  37140
ccctggtctc tgcccttaag tgatctatca tccccactgc cattaggggg agaagctctg  37200
aaaaagagtt gtctcccatc aactctggtc tacaaaggac agccctactg agcctcagcc  37260
atgtgcccga caccagcaga ttctttacag cctgggaagc agagtgtctt ccctgccttt  37320
```

```
ccagggaaca tagccagctt acaggctttt tgatcttata gagtaggtca gttatatttt  37380
gccccatttc ttttatcctt ttgatcactt cctcttggcc caccatgtaa actcaagcat  37440
ccctgcttca tttaatcgag ctgttgcttt ttctaagcta ccaagagcaa ccccagcaat  37500
atatcagagc cctctcttgg gacccttgct agggtgttaa atcctgcatc ataggagaat  37560
gcccccacat cagcaaagtc cccttatcct cttgatatcc cacctgcccc agtccagcac  37620
cttcaggatc tggtctcaat cacaggatcc agcacctttg ggactgttgc aagcataaga  37680
tccagcactt ttgggatcta gtctcccact tcctgctagt acttgttagc caaagactga  37740
gttcctttgg catacaattt ttttcttctt ccttgacagg tccaagttgg gccatgctga  37800
gatttgaccc tccttgtggc caggaggggga ggtaggggcc gatcctgagg aaggcactca  37860
ttttctcctg gggcacttgt ctctttcaga catctgcata cttttcaaga gagaaaaggc  37920
ctccttctca cagcaagact acttctgtag atgcaggtgg ctcgtgggaa tctggcaatt  37980
caaaattctc aagtgtactc actagcacat tagaaaacca gtagtacaca tctctttcca  38040
aatcttcatt cagtgacact atgtcagtag ctggaaatgg gccatggtgg gtgtatttaa  38100
accatgaaaa tcagaaaatg ctacaaacca gggcatcccg catctctaga cagcagattg  38160
ttggccattt cccagcatac cattgtgtat actccttccc atcagggccg tggcttgcct  38220
tggtggagga ctcagccctt gctgaagttc tgctactgct cttacaattg agtcctatgc  38280
ctggtctcca gctctgcctg cctcactaca ggagacaagc atctctttga acactgccga  38340
gaagaccctc tggctctcag gcttggcttt aaatcgatag acctgagcct gccattttct  38400
cttttccatg catcactcca ctgatccaca ggtctcagtg gcatagtcct tcgggttagc  38460
atctccccca caccctcggt gccagagaca ctgagtaaga aagtacctcc ctgtctaccc  38520
ccatccccgc tccccacagg cagggccttg gcgatccact gctgcaatgt gccagagact  38580
gtcagtactc ctaccaccag tgaggtggca accagctggg aagtgatcca actccagagt  38640
cccgccctca taggctgatt tctaggacca cccctggtat actgtgttag gttcttgaag  38700
cagagcctga gataaggatt ctggcacctg tgattgagtg ggagggtgct ctcaggatga  38760
gatggggtag aaataggcaa aggtacagat tcagcagcag ttgagcctca gtctgaccca  38820
gcagggagct ctcaaatgtg aatgacatca cagagttgtc cctctgaggc aggggccagc  38880
ctttgtgctc ctacatgagt cagtcactgg ctggaggccc ctggggaaag gctagggctg  38940
ccagctttag caaataaaaa attagggcac tcagttaaat tgaatttcag ataaacaaca  39000
```

<210> SEQ ID NO 6
<211> LENGTH: 45980
<212> TYPE: DNA
<213> ORGANISM: Homo sapiens

<400> SEQUENCE: 6

```
actagcacat tagaaaacca gtagtacaca tctctttcca aatcttcatt cagtgacact     60
atgtcagtag ctggaaatgg gccatggtgg gtgtatttaa accatgaaaa tcagaaaatg    120
ctacaaacca gggcatcccg catctctaga cagcagattg ttggccattt cccagcatac    180
cattgtgtat actccttccc atcagggccg tggcttgcct tggtggagga ctcagccctt    240
gctgaagttc tgctactgct cttacaattg agtcctatgc ctggtctcca gctctgcctg    300
cctcactaca ggagacaagc atctctttga acactgccga gaagaccctc tggctctcag    360
gcttggcttt aaatcgatag acctgagcct gccattttct cttttccatg catcactcca    420
ctgatccaca ggtctcagtg gcatagtcct tcgggttagc atctccccca caccctcggt    480
```

-continued

```
gccagagaca ctgagtaaga aagtacctcc ctgtctaccc ccatccccgc tccccacagg    540
cagggccttg gcgatccact gctgcaatgt gccagagact gtcagtactc ctaccaccag    600
tgaggtggca accagctggg aagtgatcca actccagagt cccgccctca taggctgatt    660
tctaggacca cccctggtat actgtgttag gttcttgaag cagagcctga gataaggatt    720
ctggcacctg tgattgagtg ggagggtgct ctcaggatga gatggggtag aaataggcaa    780
aggtacagat tcagcagcag ttgagcctca gtctgaccca gcagggagct ctcaaatgtg    840
aatgacatca cagagttgtc cctctgaggc aggggccagc ctttgtgctc ctacatgagt    900
cagtcactgg ctggaggccc ctggggaaag gctagggctg ccagctttag caaataaaaa    960
attagggcac tcagttaaat tgaatttcag ataaacaaca aattattttt tagtatatgt   1020
cccaaattgt gcataacata atgtgttttc tccgccagcc ctgggaaggg cgtaacttcc   1080
caggtatttc taggtgaagt aactttgtag atcaggagta agtcccagga aagaagtcca   1140
gctcttctct tcagccctgg gcagctgggg gtaggcacag gggcccagca ggcacccata   1200
gcatctccta cagcatctga aatgaacagg gtcatcacgt actacataca aatgtaccca   1260
ctgctgagtt cttcagggat tatatcatta ggtacttggt attttaaata cattacatta   1320
tgcagaagtc ctttgtggat tgctatattt ggagagtttt gtgatattgg ggggattaga   1380
tggagttttc agatgggcat catacggttt ttcatttaaa accctagagt attgtaatcc   1440
tagggagtga tcctgcgatt agtaaattag ctctccaata gattttcaat gtggttgcaa   1500
aggacatgca tgtggttcac cctcccagga aatccagaag ggcagcattg gcctgagtgg   1560
cctgagtttg gctggttggg ctggtaatgc tggacaaaga caatgggtgg aatggtttgc   1620
ttccctcagt cctttcagac acagcccagc ccaccacgtc aagccagtgg gtgcatctgc   1680
aaccaatccc catgagaact gcagcctctc agaggtgggc aagttggccc gggtgggtca   1740
ggaggatcag atgttgagga aatctttgga ttggaggcag gcagagcagg gaagcatcgg   1800
gtgattctat gacagaccca gggctccaag ctgcagttca ggaggggcac tggcacggcc   1860
tctgctcaac tccccccttga gtgacatcag gtgaagtgcc gacaacacag aaggcagcaa   1920
atgctgccag tcaggtctgc ttcccaggac agccagttgc taacccttct ccagcacagc   1980
actggatttt ggtcacctgg ctgggagctc cacctcccca gctgctgcct cacctgcttt   2040
tccaaacccc accctgtaaa cggtaactac attttgtgcc cactacgcct cgtttccatc   2100
tctttggagc acctctcacg tggagctgaa cagaacgacc tgttaagccc accgtgtctg   2160
ttagggttgt ctaggctgta tcagataccc aactaaaact ggattcacca acaggtattg   2220
tcaaagcaca taagaaagag tccagaggca ggcagctctc agcctggtgt caggctctgg   2280
gtcagctttc cagattctct taaccttccc cacatctgcc agatgccgcc acaggcacag   2340
gaggtacaaa caaacccaaa aatgttctgg aaacaagaag ggaaggggat ccccaccata   2400
tctccccaga ggccttcctt ctcacatctc actgtactga agccagctct agcagaagac   2460
agcagggtga atttgtccag ggtattcagc ccccagtgct gggtccatta ctacttgacc   2520
cctgaataaa acagaggttc catgagcaag aaggaagggg aactggatgt tagagggcaa   2580
gaatgtatcc atcccacccc taggagcacg catggacaac tgccccattt ttgctcctat   2640
tgcagcccag gggctagccc agagaccttg ccagtgctga gtcacaagat gctgggaaag   2700
tgagaccaga gcctggtctt ggggaacagc tcaaggccgc attggtctgc aggtcataga   2760
gcagctgctg agcagtgaga gcccacgatg ggccaggccc tgggtcttgg agacctgaat   2820
```

-continued

```
gagatagact gggttcctgt tctcctgggc attgcctctt agagggcaaa gacaattaac   2880
aataaacaaa tagaacatga agtgttttcc gatagtgact gatatacttt ggatatttgt   2940
cctctccaaa tctcatgttg aaatgtaatt ccttatgttg gaggtggggc ctggaaggag   3000
gtgtctgggt catgggggca gatccctcat gaatggttta gtgccatccc cttggtgatg   3060
agtgagttca cgtgagagct ggttgtttga aagagcctgg ccccctctca ttctcctgct   3120
cccactcttg catgagacac ctgctccccc ttctccttct gccatgattt taagattcca   3180
gggacttcac aagaagcaaa tgctaacgcc atgcttcttg ttctgtctgc aaaactgtaa   3240
gccaattaaa cctcttttct ttgtaattta tccagtcttg ggtatttctt tataacagca   3300
caagaacagc ctaatacagt gatgctctcc aagtgacctt tgggctgaga cctgaagaag   3360
aaggggaagc agttaggtct gatagctcat gcctgtaatc ccagctcttt aggaggctga   3420
agtgggagga ctgcttgagc ctaggagttg aagaccagct tggaaaacat agcaagaccc   3480
tggctctaca aaaatatttt ttaattggcc aggtgtggtg gtgcacacct gtagtcccac   3540
ctacttggaa ggctgaggca ggagcatctc ttgagcccag gaggttgaga ctgcagtgag   3600
tcatgttcac accactgcac tccagcttgg gtgacagagc aagacctgtc tcgaaaaaga   3660
agaaagaaga aagtaggaag aagaagaaga agaagaagaa gaagaagaag aagaagaaga   3720
agaagaagaa gaagaagaag aagaggaaga ggaacaagaa caagaagaag aacaagaaga   3780
acaagaagaa gaacaaggag aacaagaaga agaataagaa gaagaaggag aagaagaaga   3840
aggagaggaa gaagaagaag aggaagagga ggaagaggag gaggaggaag atgaggagga   3900
ggaagcagaa gcagaagaaa aagaaagaaa agaaagaaag agaaagaaag aaaagggaag   3960
gagggaagga aggaaggaag gaaaaaggga aggaaaggga aggagaggga gagggagaag   4020
gaagaacaaa gaagaaagaa ggagaagcag aggcttgtgc tggatagcct tgcttttgcc   4080
aatgaccttg ctgattttca gggggtcctg gtgtcttagt ccatttgtgt tgctgtaaag   4140
gcatacctga ggctggataa tttacagaga aaagaggttt atttggctga gagttctgca   4200
ggctctacaa gaagcatggc accaatgcct acttctgatg agggcctcag tctgcttcca   4260
ctcatggcag aaggtgaagc agagcctgca tgtgcagata tcacatggtg agagaggaag   4320
cacgaggggg cagggaggtg ccagcctctt cctaatagta agctgtcttg agaactaata   4380
gagtaagaaa taactcacac cctgccccca aggaagggca ttaatctatt catgaagtat   4440
ctgcccccat gacccaaaca tctcccatta ggccccccac ctccaacatt gaggatcaaa   4500
tttcaacatg aggttccggt gggcaaacat ccagctataa tactgggcaa tgctgaccag   4560
actcttcccc tctcaggccc agagctcctt ggccctgtaa caacagaaaa ttgcgtttga   4620
gtgtcaagat ttttccttta gtccccatgc agctccttag aatgaggtgg catcttctcc   4680
cttttcatag gtgaagaaac agaagctctg gaggaacgaa tcattcatcc aaggtcaggt   4740
agctagtaag cgtcccacca gctccccaga tctcctgttt cctgtcccaa gtcccactga   4800
gtgagctgga acaatggctt cactggcacc tgccgggaat ggtggcaggt gcctataatc   4860
ccagctactc gggaggctga ggcatgagaa tcacttgaac ccgggaggca gaggttgcag   4920
cgagccaaga tcacaccact gcactccagc ctggataaca aacggagatt ccatttaaaa   4980
aaattaacat ataatataca tacagtaaca ttcacttttt aagtgtacag tttgatgagt   5040
tttatcaaat gtatatggtt atataaccac catcaccatt aaggcagaat cttcccatca   5100
ctcaaataat tccctcagcc ccacctcttg ctgtcaatca cttctcccac cctagccact   5160
ggaaatcatt catctgtttt ctgtcccctt ggttttgcct tttctagaat gttctataca   5220
```

-continued

```
tgagaccact gagaatatag tcttctgtgt ctggcttctt tcacttaaca taatgcctag   5280
ctcagcagtg tgtcaatcct ccctcccttg ccattgctga gcagtgagta ttccactgta   5340
tggctgtgct acggtgtgtt catccattta ttcattcacc agctaatggg catttggatt   5400
gtttccaggc tttggctatg atgagtgaag ctgctgtgaa tgttcaagta caagtctttg   5460
tgtagacagg ggttttcaat tggcgggata aatacctagg agtagtatcg tgtggttaag   5520
cgtacgttta aacttagaaa aactgtcaaa ctgttttcca atgtggcctg taccatgttg   5580
catttccatc agcagtgttt gagaattcca attgctccac atcctcctcc cgacacttgg   5640
tttcacccat cttttaaata ttagccactc tggtgactgt gtagtgatat gtcagtgtgg   5700
ttgtaatttg catttctatg attgactaat aataatgttg cagatatttc tgtatgctta   5760
gtgggcattt ttggtgagtt tttaaaaatt gggttgttgt caccgtctta ttgagttgga   5820
agaattcttt atatgttctg gatgtttatt catgtgtgtg tctgctaaga ggtgagactg   5880
gttctaccct ggtcctaaca agcaccctgg gcctgcatcc ctttttgtgt ctgtgagctg   5940
ggtctgcagc cctctcctcc cactacctac tgcccagcag taccccctcac ccatcactgt   6000
ggctcctgca atgacatctc agcctgtctc tccctccctc cagctagcca gaggcaggat   6060
ggctcagtga cacagggtgg gccctgaaga cagagtgcca gggtttggac cttgtattag   6120
caagagtcac aagggaaact tactttatct ctccatagct ctgttgtgag gatccaataa   6180
attaatccat agaagagctt aggacagcac ctggcacaaa gtatacatga gctattatga   6240
tgttattctt ccaacccatt gtttctgtgt tgtcataaac atgaatgcag gactcagtgt   6300
cccagctctg tgtccctcgc atacattccc taacagccca caggtcttgc ctgtcaccgc   6360
ctcattcaat aagtgatgac tctgcctctt ccttggctgg ggccttgcat tggacatttc   6420
tgtatccata tttgtttttt aaaaactagc tgttggccgg gcgcggtggc tcacatctct   6480
aatcccagca cttgggaggc agagacaggt ggatcatgag gtcaggagtt caaggccagc   6540
ctggccaaca tggtgaaacc ccatctgtac aaaaaaatacg aaaattagct gggcgtggtg   6600
gcatgcacct gtaatcccag ctacttggga ggctgaagca ggagaatcgc ttgaacctgg   6660
gaggcagagg ttgtagtgag ccaatatagc gccactgcac tccagcctgg gcaacacagc   6720
aaaactccat ctcaaaaaaa aaaaaaacaa aaaacaacct agctggactt gacactcttg   6780
ttagaggaag atttttccac atctgttaac ttttcttcta ttgttatcca tctgtgcagg   6840
tttttctgtc ctcctgagtc atttgataa tttatattat attttgaaaa tcatccattt   6900
cctatagttg tttattagtg tcttctctgt tatatttgat cagattacca aatcttgctc   6960
attgattgcc catttatttt attgtgttta tttttttgag acagggtctc actcgacagc   7020
ccaggctgaa gtgcagtggt gcaatcatgg ctcactgcag ccttgacctc ctgggctcaa   7080
gcaattctcc cacctcagcc tcctgagtag ctgggacctc aggcacacgc caccacagct   7140
ggctaatatt ttatttattt atttatttat ttattttttgt agagatgggg tctcactatg   7200
ttgcccaggc tggtttcaaa ctccttggtt caagtgatcc tcctgcctca gcttcccaaa   7260
gtactgggat tacaggagtg agccaccatg cccagcccct atttacttta tagtaagtgc   7320
cttcatgggc ataaatgttc ctctgagaca gctttggcta ttagccatac ttttaatatt   7380
ttgtacattc atggttattc atttataaat ggtctgtaat gcaatgcaga tttccccttt   7440
ggcccaaatg ccatttacag cagcactttt ctctttctga gcagacagaa tattttggtt   7500
tcccctctgt tgtttatttc tcgtctgcct cgcctcattt gctaggtgtt cccttggtgt   7560
```

-continued

```
gccttaagta tgagccactc aaatatttgt gtttctctaa acacccctga cactgtcctg   7620
ctggtttctc tatctggaat atccttccct tcttggccag ttccccctag tgcatcaaag   7680
aaatcctgct cttttgcctt cagaaaacaa aacaaaacga aacctatcag tctccttatg   7740
tccccaaaga catagctttg ctggtatctg gttgtattga gctgttcatt tgtctcttct   7800
gctagatggt aagctccttg gaaactaaaa actaatcact tttctaactt cagactgagc   7860
acaaattagg ttctcaagaa acattgaata atgagtgatc cggtatcccc ttccaacata   7920
tttttggtca ttgataccat cattctgagt agttactagg gaacacttca ctgcagtaac   7980
caatacagca aaacgtgaaa tacagttaca tagtagaatt gtatttcttg cccatataat   8040
agtcaagtgc agttcttcat cagctgggag gttctcctcc acacagtcat ttaggaatcc   8100
agggaacata gcagaggttg ctagctctag acccaaaccc atgtcctctt tgtccacagt   8160
gaggacaatg ccagcaacag ctggccagct gttctgtagt tctcagcctc cctcgcagtg   8220
agatgtctcc atgcaatttc agtggagcaa catataccat ttccatttcc aggtgtaggc   8280
tcctaagaag agggtggctt cttcatgttc tttctcacct ttccgtaggc tagctgcaga   8340
taatgatgag gctttaggga gtgggtggag ccataaagta gaagcctgga ttcctaaatg   8400
acggtgtgaa gtgttcccta atttcacgta attgtttctt aatttcctgt ttgggttatt   8460
tgttgctaag gtataaaaaa accctgattt ttgtgtgttg atatttgtgt gctgcaactt   8520
tgctgaatta gcttattagc tcaatttgat ctcagatatt agctcaaata ttttgggaga   8580
ttatttatgg ttatctacat aagatcatgt catctgaaat aaagatagtt ctatttcctt   8640
ctttctatct tagtccattt gggctgctgt aacaaaatgc cataaattgg aggctgagaa   8700
gtccaagatc aaggcccaag ctaattcact gtctgatgaa ggcctgcttt ctggttcata   8760
catggcacct tctagctgtg tcctcacatg gtggaaaagg caaggtagct ctctgggatt   8820
cctttttgtt tgtttgtttg ttttgttgtt tttgtttgat tttttgagac agagtctcac   8880
tctgtcacca ggctggagtg cagtggcaca atctcggctc attgcaacct ctgactccct   8940
ggttcaaacg attctcctgc ctcagcctcc tgagtagctg ggattacagg tacccatcac   9000
catgtccagc tactttttgt atttttagta gagacagggt ttcaccatgt tggccaggat   9060
ggtctcgatc tcttgacctc gtgatctgcc caccttggcc tcccaaagtg ctgggattac   9120
aggcatgagc caccgtgcct gtcctccggt attcttttta taagggctct ttttcttttt   9180
atgtgggctc taccctcatg acctagcacc ttctaaggcc ccacctctta atatcatcac   9240
acagcagatt taatatatga attttgaggg gacacattct ttccatagca ctttccagta   9300
tggatacctt ttatttattt ttcttcccta attgctttgg ttagaaatgt cttccctaat   9360
tgctccacta ctatgttgaa aagaagtggc aaaagtgggt attcttgtct tgctcctctc   9420
ttaggaagaa agtttaagtc ttttgccatt aaatatgacg ttagctatgg ggttttcata   9480
tatgacattt atcatgttga ggaaattttc ttcttgtttc aatgatgaca gggtgttgag   9540
ttttgtcaga tgctttttct gcatcaatca atatgaccat gtagtttctt tgttttattc   9600
cattattgta gtacattaca ttaatttttg catgttgaac tattcttgtg ttcctgggat   9660
aaatttcact tggttatggt gtataatcca taaccataac ctgaagatat gctgaagagg   9720
ctaagtgcca tggctcatgc ctgtaattcc aacactttgg gaggctggtg tgggaggatc   9780
acctgaaatc aggagtttta gaagagcctg ggcaagtaaa caagatccca tctctacaaa   9840
aaattgaaaa ttaccgctgg gcatggtggc tcacgcctgt aatcccagca ctttgggtgg   9900
ccgaggcagg cagatcacct gaggtcggga gttctagacc agcctgacca acatagaaaa   9960
```

-continued

```
accccgtctc tactgaaaat acagaattag ccaggcgtgg tggcacatgc ctgtaatccc  10020
agctactcag gaggctgagg caggaaaatc acttgaacct gggagacgga ggttgcagcg  10080
agccaagatc atgccattgc actccagcct gggcaacaag agcaaatctc cgtctcaaaa  10140
aaaaaaaaaa gaaaagaaag aaagaaagaa aagaaaagaa agaaaattag cttgatgtgg  10200
tggttgtgca cctttagtcc tagctactca ggaggctgag gcaggaggat tgtttgagcc  10260
caggaggttg aggctgcagt gagccatgat tgcaccactg cactccagcc tgagcaacaa  10320
agtaagacct catcactaaa aacaaatttt ttaatactga agaattttat ttgctggtat  10380
tttgttgagg attttgcatc tatattcaca agaaatatta ctctgtagtt tttcttcttg  10440
tagtatcttt gtctggtttc agtatcaagg caatgctggc ctcatgagat caatcaggaa  10500
gtgttacttc ctcttttatt ttttggaaga atttgagaga attggtgtta attcttcttt  10560
aaatggttgg tagaattacc agtgtagaca tctggtcctg ggattttctt tgttgggagg  10620
tttttttagta ctaattccat ttccttactt gttattagtc taatgagatt ttctgtttct  10680
tcttgagcta gttgtagtag ctcatgtgtg gaatttttct atttcatcta agttatccaa  10740
gtttacctaa gttaaagttc cattttatct aacttgggta agccaacaaa caatactaaa  10800
ttgttcatag tattctctca tagtcctttt tttctctaaa gtcagtaata acgttcactc  10860
tttcattttt tcattcctga ttttaataat ctgagttctt tctctccccc tccctgcaat  10920
tgagagtcat ttaaaagtgt cttgattaaa ttttatatat ctgtgagttt tccagttttc  10980
cctctgttat tctcttctag ttttatttca tgtgatccaa aaagatactt tatatgattt  11040
caattttttt acatttacta agacttgttt tgtgactaaa atatccttga gaatttccat  11100
gcacatttga gaaaaatgca cattctgctg ttgttggaca gagtgttctg tatatgtctg  11160
ttaggtctaa ttggtttaga gtattgttct agtcctctct ttccttattg atcttctgtc  11220
tagttgttta atccattatt caaagtagtg gccgggcacg gtggctcaca cctgtaatcc  11280
cagcactttg ggaggccgag gagggtggat cacaatgtca ggaggttgag accagcctgg  11340
ccaacatggt gaaactccgt ctctactgaa aatacaaaaa atttgctgga catggtggca  11400
cacgcctgta atcccagcta ctcaggaggc caaggcagga gaatcacttg aacccaggag  11460
gcagaagttg cagtgagctg agatcgcacc attgcactgc agcctgggca acagagcaag  11520
actctgtctc gagaaacaac aaaaacaaaa acaaaaaaca aagtagtgta ctaaagtctc  11580
caactactat tgtagaactc tatttctccc ttcaatgttg caaaattttg tttcatgtat  11640
tttggtgttc tgttctttat aatttttata tcttcttaat ggatgaaaac ttttatcaac  11700
atataatgtt ctttgtctct tgagactttt ttttttaact taaaatctat ttgggctgat  11760
aatacagcca ccacaactct catattggtt gttattttca tagaatatct tcttccatcc  11820
ttctacttta aaattcttct atctttatat ctaaagtgag cctcttgtag atagcatata  11880
ggtggataat gttctcttta ttcactctgc caatatctgc cttttaactg gagtttaatc  11940
tatttatata taaaataatt actgattagg aaggacttac ttctaccact cagctatttt  12000
ttttctgtgt gtcttataca tttttaagtt tctcaattcc tccattactg gattttttttt  12060
tttacttctt gattttgtgt ctgtgttgtt acattttgat tattttctcc ttttgatagc  12120
ggcaggaggc agccaaatgc ctggcagata gaagcttgtc ccccatgaaa ccccaccttc  12180
aagccaaaaa atagcctgaa ggctgaaaga ccggactgct ggtcccagat gaaacccatg  12240
atccagagtg agaacttcca ttcctgtttg cctgccctct aaataatccc ttttaaccaa  12300
```

-continued

```
tcgaatgttg ccttttccaa tactacctat ggcctgcccc tcccccattc tgagcccata  12360
aaagccctgg aatcagccac attgggggca ctttgccaac ttcaggtagg gggaccacct  12420
ctgtatccct tctctgctga aagctgtttt catcactcaa tgaaactctc accttgctcc  12480
ctctttgatt gtcagcgtat cctcattttt cttgggtgtg gtacaagaac tcgggaacca  12540
gtgcacaagc cagacttggt ctgggcagca cgggttagtg ggccatctcc cacagcaggt  12600
agcatggcca agtgaggcct gggcagggca tcaccaaggt ccctggcttg caaagtgacc  12660
aaggaaaaaa tcctgtgtca ctttcctttt ctcatatttt ttagttattt tcctaatgat  12720
tgccttgagg atggcaatta acatcttaca cttataagaa gctagtttga ataatagttc  12780
caatagtaca tgaacactct actcctatat atctccatcc ttcttccttt atattgttat  12840
tcccacaaat tatgttttta tacattatat cctcactaac ataaacttat tattattttc  12900
tgcatttgcc ttttaaatca tacaggaaaa caagaatcac aaagaaaaac tacattaata  12960
tttgctgtta tatttaccta tatagtgaca tttaacagtg tatttttatg tcttcagatg  13020
tctttgaatt actacttagt gtcttttcat tttagcctca atgtttccct ttagcatttc  13080
ctatagggca ggcctgccgg taattaattc cctttggttt tctttatctg aaatgtctaa  13140
tttctttttt attcttgaag aatagttttg ctggctataa gattcttagt taatagtttt  13200
tttcccagca cttcaattat tattaaagtg ttattattat tattattatt attttgagat  13260
ggagtctccc tctgtcactc aggctggagt gcagtggcgc aatctctgct cactgcaacc  13320
tccgcctccc aggttcaagc aattctcctg cctcagcctc ccgagttagc tgggattaca  13380
ggtgcccgcc accatgccca gctaattttt gtatttttag tagagacggg gtttcaccat  13440
gttggtcagg ctgatcttga actcctgacc tcaagtgata cacccacctt ggcctcccaa  13500
agtgctggga ttagaggcat gagccaccat gcctggtcta aagtgtaatt attattacag  13560
ctgccatttg gcctccttgg tttctaatga gaaatcatct gttaaactta ttgcaaatcc  13620
ttggtatgta tgctatgtgt catttctctc ttgctgcttc caagattctc tctctgtctt  13680
tgtcttttga caatttgact ataatgtgtt tcagtgtgaa tttcttagag tttatcccac  13740
ttggatttca ttgagcttct tggatgtgta cgtttgtctt tcaccaaatc tgggaaatta  13800
tttcaccatt tctcaaatat ctttttcttc ccctttccat ctctcttctt ctggagctcc  13860
cgtatactta gttggcatga ctgatggtat cctactggtc cctcaggttc tgttcatttt  13920
tcttctttct ttttttctgc tctgcagact ggataacttc aatcgccttt tcttcaagtt  13980
caatgattat ttcttctgcc tgctcaaatt ggccatttaa cccctccagt gactttttca  14040
tttcagtatt gtacttttca gatccagaat ttctatttgg ttcctcttta ataaattctt  14100
tttattgtca ttccccatct gttcatacat tgctctccca atttcctgta gttctttgtc  14160
catggttttc tttagttaat taagcatatt taagacagtt gacttaatgt ctttgactag  14220
taattccaat gtctaaaatt ccttatggat agcttctttt aaattatttt tgtcctgtta  14280
gagagtcata tcttcctctt tatttgcttt gtaatacttt gttgaaaact taacattttg  14340
agtagtaaaa tgtggtaatt ctgaagccag attctccccc tcctttgaga ttggttttgt  14400
tgtttgttga gggctgcagt tgtccatttg tatagtgact tttccaaacg atttttgcaa  14460
agtatgtatt ctctcttgtg tctggtcact gacgtttctg ttctggtgcc tctgcagtca  14520
gcctatgacc tggaagagca ttccttaaat gcatagattt ttttaaaacc caagaaacaa  14580
aaaacctagc atgtatgtac ctttttaaaa atcttctgat agatgccacc tggaaggctg  14640
ctgctgcctg aaggggcaga aacaaaggca agctctactc tgagccctca gggaaccacc  14700
```

-continued

```
agataaacaa aagaaatttg attctccaaa tttctggaag acaaggtcct ttctgcccac  14760
tcctgctcca gccagctgct ctaggaacac aattactgtc cacatggcca caggaatgtt  14820
gaagaatgca ggatggtagc tggtttgccc acaccactca cttatgagcc atcagcatgc  14880
ctctcccttc atcgagcact cccatggttg ctgtaagtgt ccaatcaggt tccagaattc  14940
tgaaagagtt gactcttaca ggattttttt cttttctaac ttgctggttg tttagataga  15000
ggaaccaatt cctgaagttt cctacgttgc cagcttcatg aggatcattc cctagtaact  15060
cttttcagac aaaaagcttc attgatttac tgtaggacta gcatcaaaga gtctatgcca  15120
cctagtctgt ctccttaaaa cacagaaata atcagtatgc attggggtag gagtttggca  15180
ttagatctgc cgtaaatcaa gagctgggga cagcccatgt cttaaactct gacccaaggg  15240
ctaaaatatc ctttggtagc aacaacagct acaaactatt gaacaacttg tatgtgccaa  15300
gagccttacc tgcattatcc cattgaatcc tctcaacagc cctgtgaggt agtagaattg  15360
ttgcctgccc cttactgagg cctagaaaca ttaaggaatt tgcccgaggc cctagagcca  15420
gtgagtggca aagccagtct ccagactcag gctggagatc ctacagttct gtgttacccc  15480
agtgttatcc tgcctctcag cacagagtct tggatgattc tcctaacccc tccctaggca  15540
atgcacaggg ctgctccctg caccccttact catgctctgc tcttcaaccc caacagtgct  15600
ggccttaggc tttatccctg acacccagcc ccaggctcca ttccatctgt tgacagaggc  15660
aaacactggg gcaaaactga cctctgtgga taccactgtg tccacctcca ccagcttcag  15720
ctgaagcctc tgaacatctc cagcatggaa gaagccccaa aggatatttc ctgtccccca  15780
gcatatgctt gaccctgaag ccctccccat ctagtcaaga agaccaaact gttaacaatc  15840
ctggagtcag agtgacccat gggtgaatct tagccaagtc actcatagct gttgcatcct  15900
agtaaatccc ttaactccca taggcttcag tttccctgca tataaaatga cagccttcag  15960
ctcatcggcc agtttcaatc catctaaagg gtctagcaca tcccctggca tgtggaagcc  16020
acagggcaca cactagttgt ggtcatttga tcctggcatg ctctgctgtc tctcggctct  16080
ccccttgcct ctttccctga tgtcctggcc atcagccact gcctaacacc ctcccactca  16140
ccaggccctt agcctgcccc ttagcacaag agcacagccg gtctcaagtc taccctgctg  16200
taagcaaaca cttgcaacat catgctgacc tccaggccct gttgcatcag cgtgcccaca  16260
cttggtgccc agctggtact gagggtatca gggaacaggc cagtggtgga agggcggaca  16320
ctttgggttc cctggtttcc tggctcccaa tatctttccc aatggcatat ggggtctagc  16380
agcttggctc atttaactgt gaacctctac cctttagaat ctgggcctcc aggcttgctt  16440
ctgtgcaaaa tggcagataa ggctcaacct ttcttttttt aacttcattg ttaaatatta  16500
ctccattaat acccatttac tgcagaaaag gtaggaaata cagataagca aaaaggaaaa  16560
taaattaaaa tcctcatacc accatcatca agataattac tgtcaccatt ttggtatatt  16620
tcctcccaat acatatatta tctatatcgt atatacgaca aaaatggatc atactatgtt  16680
tcctgttctt cccctgtgtt agtcatctat tgctgtataa caaactgcct caaaacttag  16740
tggcttcacc tttccgtgta ttatgatgac aagaatgtgg tatgacactg tcttatatct  16800
ggatcatatg ctaaaagata gaaaatggtt tctaaactta tttgttctgt aataacaaaa  16860
ttttatttca taaagtgttt ttaaaaaaaa ccatagtagc ttgaaacaac aaacctttgt  16920
tatctcacac agtttctgta ggtcaagaat tcagaagcag cttagctggg tggtctggct  16980
tggtgtctct cctgaggtca gggttttggc tggggctgca tcacctgaag gcttgactgg  17040
```

-continued

```
ggccagagga gctgcttcca aagtggtcca ctcacatggc tggcaagttg gagttgcgta  17100
ttggcaagag acttcgcttc ttctcaatgg atcttcccag agttcttgta ggcaacctca  17160
tagcatagca gttggcttcc cccagaggga acagtccagg agagaacaag gcagaaacca  17220
cagggtcttt tctggcttag gctccaaagt catactccac catttctgca ttatcatatt  17280
agttacacag gctagaccta ttctgcatgg aagagactat accatggggt gaataccaga  17340
agcagggcta attgaaggcc agcttcaagg gcggctacac attccctttc aacagtatgt  17400
catgaacatc tttccatgcc aatagagcag atgaatctta ccatttttaa tgactacatg  17460
taagtgtagc ataatttatt taaccaacct cctgtagttg ggtatgtggg ttgtgtctcg  17520
tttttgata gtagaattaa tcatcttgaa tatccatcac caaacttgtc atattatttt  17580
cttttgatga atgaaaaaga aaatcaagtc atgtctgtca atcagaaccc tgagcaacta  17640
agaaatgggg gtaccactgg gacatagagc aaggtccctt ctgattctgc tcttgtcttt  17700
ctctccccat gaaatgggga gttcactatc tactgagaca tcctagccca cagctgcaca  17760
gttctgtctt tttagaaagc tctaagcaga aacaatgttc atccatcctc ctcgggacag  17820
cccttgagct actgaagact ctaagcatgt cctggtcatc ctccatgagc catcatctct  17880
gaggccctcc ccttcttggc ccctcttctc tggacaggtt ctggacagtc ttgcccttcc  17940
aaaattcctg gaaagcagga actgttcctg ctacaatgac tctcaactcc agtgcagtac  18000
agactgttgg tgtcacccct tatcctgaag aagaggcact gagacaggac aagggtgggt  18060
gcccaggagg gctggcatga gtcatgagaa tctggtcccg gagaattaga cggtgtgggg  18120
aagtaggggt gttgggccgc tttctggcct catggatgcc aatgaatatc agcaggtggc  18180
tcccagaaag gaactctagg ggatgcctgt tgctctaaat agaggctaga gagggcactg  18240
gcagttcagt caaccaagaa agggggccca cttgcctcag cttcaggctt tgtacacatc  18300
ctcagccttt cttgagaact gaatttagat tctcctcccc tgtgctgtgt gcttggccca  18360
gaagaagggc aagtctcgct gggtggctgc ttcttggcct ggctgaacca gaaggcccca  18420
gtgccactcc aaacctgggt gtgagccctg cccccatgag caaacagtag ctcagagctg  18480
ggggctgtgg gggtcagtgg cctgtcacat gagatctgat gaggccatct ctgctctata  18540
ttgggaaagg gatcaattgt atcaagggct ttcttgggag tgatcactct ggccattggc  18600
gagagacctg gcattctgac aaggcaccct ccataccctg acccacttgc cagctccagc  18660
taattttagc aggctttggc aggtgccagc aagtacatag catgtggatg tcactcccag  18720
gtgagcccaa ggagaggcct gggccagagc ctggaagtca tggtctatgc ccatggaggc  18780
acccaaagca agcctgaggc ctggactttg cagtcacaaa attaagaatg atacccctgt  18840
tttttgtttg tttttgatca gttggccacc ttcctccacc acccttccc caagttccat  18900
acagacccct ggattgtatg aaatgcaaat cgaacctctc tgcagatgaa aatccactgg  18960
ggatcccctt gcctccaaga gcaagtccag acctgcacca gcgcgggcca ggcccccctta  19020
ggaccccctc cctgtccaag ggcatttcag taagtgttct gtggccaagg cagcctggtg  19080
actttctgcc cgcacaaggc tgaggaatgg aagatgggta ggctggctct gcacaccccc  19140
tcctgctggg cagcaatccc taccccatgt tcacagagtg tggccggctg ccccatggct  19200
ctgtccccgt ggccctgtca actgttaccc acatggccta ccctcccttt ctgccctgcc  19260
tctgacccca tggcaggggg cagagtattt gagcagccgc caggctgagc cctttcagtg  19320
cagaagccct gggctgccag cctcaggcag ctctccatcc aagcagccgt tgctgccaca  19380
ggcgggcctt acgctccaag gctacagcat gtgctaggcc tcagcaggca ggagcatctc  19440
```

-continued

```
tgcctcccaa agcatctacc tcttagcccc tcggagagat ggcgatggat gtcacaagga  19500
gccaggccca gacagccttg actctggtaa gggtcacacc aaagttaggg actttgcact  19560
gggagagcag cacccagggc agggcccttg gttttgcaga ttaccaaaac taaggctggg  19620
ggcagggaag gcgagcaggc ttggggcacc ttggaaggag gcacatgggc cttgggggtc  19680
ctggctaggg cagctgtgcc tgccactggc cctctgccca ccacccctcc tcactgtggc  19740
tatccagtgt ccagcctctc gaggggttct agggtactta ttcctggagc taacggtgac  19800
ccaggacacc agtgtccggg gcctggcctg gggcttttat ggggggagct ggctggctgc  19860
ccagggctgt ctggctctct gggggctctg catggcattt ccaggggttg gtggatcagg  19920
gattctgtcc ctcaggagaa tgtgggcact agcccaaggc cactcacttc tgtgtacata  19980
gccacctgag ggcccaggaa tggagggggc caggctacag ctggacatct ggcactcgga  20040
tgggctctgg agcccccagg cctgcagcat ctgcccaggg actgccctgg cccttggcca  20100
tttcctcagg gacccacagc tccaccagcc ggcccctccc agtgctggaa tagacagttc  20160
ctcagtccac atctgccaaa ggcggcacta gaaggcatcc tgcctttttt actgcgttct  20220
ggaggtgggg tcacaaagca ctgctcactg cataaaaggg acagcatcct gcccctggca  20280
gccctgcctg accagctccg cctctcccac tgctatccaa cctgtacacc ctggtgacca  20340
tgtccaggcc agtggcctta aggactgtct ctgtactgat ggctccacat ctacctctcc  20400
agccagactc tcctctgaac tcgggcctca catggccaac tgctacttgg aacaaatcgc  20460
cccttggctg gcagatgtgt taacatgccc agaccaagat cccaactccc acaacccaac  20520
tcccaggtca gatggaacct cttcttccca ggcccttctg ttcctctcct cagcccctcc  20580
cacctccctt cagaataagt ctagactctt atcgctttca ccaagcctgc gcccagcatc  20640
cctgcacagg gattgttagg acagcctgac gccctgcttc caccctgccc caagatgccc  20700
ctgctctgca gcccggcgcc tccaggcttc tcacctcctg ctgctcacag ctcagcctca  20760
ctccctccct ccccgcctct gctccagcct cagtgcaggt cccctgctcc catcttctgg  20820
cagcagctgc ccgacctggt ccctcttcat ctgtccccat tccttcaccc cccagcctgt  20880
ccccaacttg actgaggttc tttcctgcag atccccgccc ttgagagggg ttggtcccac  20940
tgtcaactct gcttctgtgc cctgtgccgc acctggcatt cagtgagcat ctgctgaaga  21000
gatgagggtc agatgccctg cagggagtgt gggggcgtcc tcaggcaaga aaagttgtac  21060
gtttggctgt gggccctgat tatgtgtcct gtgacctctt gggtgaggtc agcaagagaa  21120
acctctgcaa gctggctggg gctgcctccc agaggctgcc agggggaggg acaggctctg  21180
tctgtgctct tcttccgagg ctacacctgg ggcgccaggc tctcagggct ccccaggtac  21240
caccacattt cctacactgc ttgggaaagc cctgtaagtt tgcacagaca cccagcatga  21300
ggctcgccag agagatactt gtagctgggg tctgggcacc aggaacagct tggtgctggg  21360
cctgaagtcg ggcaggatgc agcctggcca ggtgagagga aagcttggag ccagtgcctg  21420
ggttcaaact cctctgtggc ctatggttct gtgggcttgg ggaagggttt gtacctctgt  21480
gtccagtttc ctcacttata aaaaaaggag ataataaaag tacccatgtc ccagggtggc  21540
tgtagcaata atagggaggg gtgcccagag caggtctggc acacaggaag tgtgcatcag  21600
cctcagtccc tgccattggg cttgtcctgg gagtctgtga agccaacctc tgctccacaa  21660
tgtgaccccc aggcttgtga gaccaagctg ggtcagagct tcctcctctg gggttgcacc  21720
aggaggggaa cttctgcagg cccagatgca ccctgaggaa agggcttgtt cccaccaaga  21780
```

-continued

```
acaaggctca cctttggagg atgctcccca catgagaggt gaacccccag gtctactggt  21840
gactgcagcc tcggaagctg acagcatcta tcctccaacc catgcccact gggaagtgtg  21900
tgaggggtcc tcataggccc tgcggtgtgg acaatgcaga gaccctgtag catctggcta  21960
gggcggggcc cagataagag ccctgtgcca ggagagcctg gccggttctg ccactgtggg  22020
gagacaggct cccccacccc atgtcccctg cttccctgca gcccacagag aatacagacc  22080
tacttttaca gaaatccaga tttttgtgta aaagtgtctc tattttaagt agattttaag  22140
tggtggcagc aaatttaagc ttttgagaat attatacaga acaaatcaga ttcacaggcc  22200
agatgcaact ttatttacag aaatgggatc aggtcctacc tcaggtccca tctcacgttt  22260
tcacttatgc ctatacgtct ccttcacggg aaaggccaca agaggccctg cggtaagtgt  22320
cccggtgttg atttaaagtc cccaacagtg aatatgaggg tcctcactgt tgcagcaaga  22380
ggataccccc ctgtgtatct tggaaatgcc tgcagccctc ttgctgcaga acagattctt  22440
aggagagaaa ctgtcagatc aaagttaaac ttagagaaac tccaaattgc cctctgaaca  22500
gacggtatca gtttgacatc atccaatacc gggattcctc ggggagaact ttctggccta  22560
gaaggcagta gagccaggac ttcacccagt cagtggcagg gccacacgtg ggccttgata  22620
cagaggggga agacttgagc ctcctcgaca ccctacaggg cccagcctcc caacatgtga  22680
taagagaaac aacagccaac ttgtacctag ctctccttat tctccaaggg ctgggccagt  22740
tctccccaca gccctgcaag ggaggatcac tcaagggccc caactgtctg acaatacagc  22800
cacactctga tcagccacct gggcataggc tccatgccat tgtcctccgc caagacctca  22860
gactgaaatg ttggctcctc ccatgaagaa cctggggcca aaggaccaga gtccaggtcc  22920
gtggctgcca ggatgggcca cttggagaga ggcacaaggg tggtgccagg caggtgtgag  22980
ggctggacct ttgcaagagc agcatcactt ttgttgagag cccacaggta tcttataatt  23040
gggtcctagg acttcctgcc agtagccatt gtgtgcatgg atttgggtgc tggcctcacc  23100
atggtgtgct ggctgcccat gcctgcaata atgacttctg taagcctttc ttcatctgca  23160
agatgggtgc tgctggcacc tcctccccgg tgctgtggtg acagggcata gtgtgtgagg  23220
ctgctatgtg aagcacctaa tgcagggcct ggcatatgga ggaattcagc aaatgacaga  23280
tgccttcaca gttagttcct ggcatcctct acattggtgg gtgtaggaaa gaaagacaga  23340
ggaggcaaaa gttgtagctg tggggcattg aggacagcct ggattgttcc acagagccct  23400
gaggacatct ccaggggtgt gctctgcagg ggcagctgga ttggagggtt aggggtcggg  23460
gagggcgtgc actcccaccc atgctcacag cctcggaaca gtgcctgctc agccaacatg  23520
ggtgtttgat tctgtgtctt ttgtcacaga ctttatcagc cccatccctt tctgaccttg  23580
cctcagttta aattttacat gtggggcctc attaagagac atggttctta actaaagatc  23640
tgtatccatt aggaatgctt tgggctgcag gaagacaaac acctgactca ctgtggcata  23700
agtggtttgc gtctgctccc ataagctgca cgtggagggt ggatctggca ttactctctc  23760
ttccctacat ttgcagtatg ctaacagctt taacctccag ccttgtttct tcatggttgc  23820
agggtggcta tcacagcgct ggccatcaca tccttacaca gctgtgttta caaatttagg  23880
gggacattga agctcctccc ctgctaaaat caggcttccc ttcacctgtc attggccaga  23940
actgggtgaa atgcccaact ctagaccgat catcagtaag aggagtatag aattgctgtg  24000
cccaccttag attaatcatg gcgcaatgtg ctccccatac caacaaaatc tgagttctag  24060
aaactgagga agaagaggaa aatggccgtc ttgcctcctg gctgggattc agagcatctc  24120
caaccctctg agcttatgtg taagactgtg ggcaaaagtg tgtgagtttt tgtggaatgg  24180
```

-continued

```
atccacggct tttatcagag catctttcct ttttcttttt gattcaagat gaaaatattc  24240
ttatgattat ttttctcacc actgcccaga gataaccagc acattaacat ggcctttttct  24300
ccatgaatag cactagggtg cccagtggac agacacatag ctgtccacac accagcttgc  24360
tggggatgca taggcagagt cacatctgca ctcacggcct gtcctcacac tgccatgtgg  24420
agagccagca gccacaccat gggccgtcca tgctcacggg agtggcagta tcagatctga  24480
gcttcgtgtg cccaggcgtc tctcacatca gtgcataggg accctctttg ttctgtggcc  24540
cagtgtgccc atgccacaga tggcttcagt cagcagacac ctccttctag acactcacac  24600
tcactcctgg ctggccctta gcacacctgt gcagacaggc ccatttattt tcttgtgtaa  24660
atcccaagta ggaggactgg gtctctctga cagcaatgcc agctgcctgg caccctccag  24720
acaggtggct caagccccac ctcgccagct ctcccagtta gcccctcctt tccctggctc  24780
tgacctgagg gacgaagcag ggtgctacag gacgctgtgc cacagggata tcgtcaggga  24840
cagaagctac tctgccctct gctgctcacc cctccaacac gctgtgggct gcatttgttg  24900
agtggctggt accagactct gctcttctga ctttccagct ggttttacct gtagtaaagt  24960
ttgagaagat gggtcatcct gaccccgggg tcagaagaca gaaggaggcc catggcgtgt  25020
gggggagatg ccccgtgagg ccctcggtgt gcagatgcct ggtgacagcc ccaccctgag  25080
gtccccagcc tacccccctcc ccagcccgac tgctcccatc cccctccctg tgcaggtaga  25140
gcagatcctg gcagagttcc agctgcagga ggaggacctg aagaaggtga tgagacggat  25200
gcagaaggag atggaccgcg gcctgaggct ggagacccat gaagaggcca gtgtgaagat  25260
gctgcccacc tacgtgcgct ccaccccaga aggctcaggt accacatggt aaccggctcc  25320
tcatccagaa gcagctgtgg gctcagccct agctgggaga agcaccccag gcactcccag  25380
actcacagcc agcccgagac agaatctcct ggggagcaat gaagtcctcg acttgggcca  25440
gttctcaccc ttggctcctc tggtccggcc ctggggcact cgggctcacc ctggagctgg  25500
caaacctcag gaaaactggc gttttaaatc tcactcctgg ccaggtgcag tggctcaccc  25560
ctgtaacttc aacactttgg gaggccaaag caggcggatc tcttgaggcc aggagtttga  25620
gaccagcctg cccaacatgg tgaaaccccg tctctactaa aaatacaaaa attatccagg  25680
catggtggca cattcctgta gttccagcta ctcgggaggc tgaggcataa gaattgcttg  25740
aacccgggag gccgaggttg cagtgagcca aaatcgcgcc actgcactcc agcctggggt  25800
gacagggtga gacaccatct caaaaaaaaa aaaaaaaaaa gacctcactg ctccccatgg  25860
gcacttaggg aactctccca gcccagttct gcagctgggc cattgcacta gatcctcagt  25920
tggtccctgg gctctcggtg actgtccagg gcaggagttt cccattgact tttccctggt  25980
tgacctttga ccccttccac agttgacact ggtgtcccca ggtgtctggt ggccccttgt  26040
ccagctccct tagtcccttg tgccttccct cctcctcttt gtaatatccg ggctcagtca  26100
cctggggccc acccagccca aggccagcct gtgggtgtcc ctgaggctga cacacttctc  26160
tctgtgcctt tagaagtcgg ggacttcctc tccctggacc tgggtggcac taacttcagg  26220
gtgatgctgg tgaaggtggg agaaggtgag gaggggcagt ggagcgtgaa gaccaaacac  26280
cagatgtact ccatccccga ggacgccatg accggcactg ctgagatggt gagcagcgca  26340
ggggccgggg cagggggcca aggccatgca ggatctcagg gcccagctag tcctgacggg  26400
aggtgccacc tgtctaccag gggtggggag agcgggggct ggaggaccac ccagcctcag  26460
aggcagctgg aggcctgggt gaacaggact ggccaacatg tccccaagtc ccacagtcac  26520
```

-continued

```
catctggcca gcattgagag gggaacgggc tgaggaagag ttagtggcaa gaggaacccc  26580
agccagtcac accttgtcca gtttaccaga ggaaaaacca atgtgtaaga acagaaatgt  26640
gacccggcag ccagtgcact gcccccctct ccaaaggcca cccctcaccc tccaccagca  26700
tgcacagaaa gtggggtgac agcaatcaca atgtctaccc aggcagcaag gacccctgac  26760
catggggagg actggggtgc agggaacata gaagcagaat gaggcctagg gggagttggg  26820
caaggccaga gccctagctg cagccaagca catggccaag gccagctcct ggaagggcag  26880
ggctccgagg caggaggcag gaggctgccc gtggctaccc gtcctcacac ccctgcagct  26940
tgctagtctg tctgtgggct gggtgtgaat caaggcagtg ggatggtgtg gggacctccc  27000
tggccccagc agccagtgag gagcctggtc agtcagcaga gcattcagca gtatccagtt  27060
ccatggagag gcccgtgtga ggggagtcgg ggctggtctt cagtaaggat gggtggccag  27120
ggcccctaga agtagaaaag gagactccgg gtgctggaga cagaaatcaa ggatgtgcct  27180
ccatgtggag cctcaggaat agctggccag gcctgaggct gaacctcaca aggttcagct  27240
gggagggcta ggctgacaga gcacagccgg gccagggacc agcctgccct gtgttgcctt  27300
gtcccgaggg ccactgtcag caggtctctg gcatgggggga ggcttagggc ctgagcccaa  27360
caagcagcag cggaagagga gagggaaact gtggacaggc ctggcattca gtggccaggt  27420
gttgcagtgt ccctgaggaa tagcttggct tgaggccgtg gggagggctg ccggccagcg  27480
caccccccca tgccagatgg tcaccatggc gtgcatcttc cagctcttcg actacatctc  27540
tgagtgcatc tccgacttcc tggacaagca tcagatgaaa cacaagaagc tgcccctggg  27600
cttcaccttc tcctttcctg tgaggcacga agacatcgat aaggtgggcc gggtggaggg  27660
gcagaaggca gatgagggga ggcacaggca ccccagagga actctgcctt caaatgtagc  27720
ccccatacca tgtgctcaga agggagatct ggattcaaat tgtggccatg tcacctgcca  27780
cctctaatgc tgtggaaaag aagcatcaca ttagctaatt ctggctgtgc gccttgtgag  27840
gcaccagcta tgatcacccc actccagtgg aaagagcagc tggcagtagg gtggggctca  27900
aactcaggca gccgggctct gggtcacctg caggccacgg tcatgtcaca ctgcctctag  27960
ctgagtcaga aatgtgaagg aactgagatt ctacccttcc tgcaagctag caaagtggcc  28020
tgccagttac atctgtgcat gcacacacac acacagttat atatgcacac acataaaaca  28080
cgagaccttt gggtcaggga gaaagccaga tcctcactca cggcagaagc agcagccaaa  28140
gcaacatctc atgtggtttt ccaagcccca gtccctacag agacagagag ggccaggtgg  28200
cacctgtgca tgcagcgggg taccttgcag gagggaaatc ctgattttac acaaagctgc  28260
tccccccacg ccctgccttg actctgggat gacgtctcag agctgtgcag tacaacattc  28320
ttaaattggc tgggactcag ccctgcagaa atatgatatc ttcaaggaga atcgttccca  28380
aaacctctca aagctatggg gctgctctga gcctgtttcc tcagctgtaa agtagggtgc  28440
atacttttat ggccctgtgc aggaggtagt gacaggccct agcaccctgc ctccagtata  28500
tgttagcagc cacgaggcct atctctcccc acagggcatc cttctcaact ggaccaaggg  28560
cttcaaggcc tcaggagcag aagggaacaa tgtcgtgggg cttctgcgag acgctatcaa  28620
acggagaggg gtgagggggc acctgtacct gccggggggg ctgccctggg ccacccaccc  28680
cagcactgcc tgcctttctc cttggcttcc agcactgcag cttctgtgct tcttggcagg  28740
actttgaaat ggatgtggtg gcaatggtga atgacacggt ggccacgatg atctcctgct  28800
actacgaaga ccatcagtgc gaggtcggca tgatcgtggg taagggctcc ttgcacccct  28860
gccccttcca gactgctgag gctccctgtg tacaacaggc ttcaagggcc ctgtggggtg  28920
```

-continued

```
aggaccaaac tacttaacaa ccggtgatgt cagagcagag cctggtgcta cagcctgggt  28980
ggtcttgggg tatcaagatg gaagcaccgt gtacagtagg aagcatttca acgccatgat  29040
gccacattcc tgcatcagat ggtatgccag ctgcatatcc acctcaccca tcaggattat  29100
aattaaaaca cttatctggt aaattgacca actggacaga ttggtccaag tggaagagga  29160
taagcaaaag tggtaccatc tccacccgaa tggtctttcc acgggcctgc ccctgcccct  29220
gcccccaccc aaagtgaagg caggtaccag gaaagggagc agcagtccgc ccctcccagc  29280
agaggggtct tccacaccaa ctcggacctt tctcagaagt tccggaggtc attataacca  29340
gccttcactg aggagcaatc caatcagatc agttatctgc tgtgcgcaca gccgtgtggt  29400
tctatacttc tcttacttcc attttcacct ttcagaagga acgttgtctt taaatccagc  29460
atctaaacgt gagccccagc catccctggc tgtgatcccc ccagcccttt ccaccctatc  29520
ctctggaact gcctggggct ccccaagaca cttccacatg aattcccacc aagccaagct  29580
gcagctgctg ggcccaggca taacccctcc tggggcagag gtggcaagga gtgacccacc  29640
actcacatct gccccacatc cactcttgac tctgctcagt gtttaaaaac atgtttataa  29700
caattaccaa gatctgaaaa ttaggagaat tcacatcaaa gtctggattt ctgtttgttc  29760
ataaaaaact agaaggcagc caggcaaggt ggctcacgcc agtaatccca acactttggg  29820
aggctaaggc aggcgggtca cttgaggtca ggatttgaag actagctggc caacaaggtg  29880
taacctcgtc tctactaaaa atacaaaaat tagctgggtg tgatggcgca tgcctgtaat  29940
cccaggtact caggagactg aggcaggaga attgcttaaa ccctggaggc agaggttgca  30000
gtgagccaag atcacgccac tgcactccag cctgggtgat ggagtgagtg agactctgtc  30060
tccaaataaa taaataaata aataaaaact ggaagtctaa gcatcactga gccctgattc  30120
ctatgtggca gctcgactga ccagcatttg agttgctgtc cctgacagct ttgggggtgt  30180
gcagcccaca cagtcatgct agcttgaggc tctgctgtca gcagtttgaa actcttaata  30240
acttgtgaac aaaagactcc atgttgtcac tctgcacagg ggccagcaaa ttacaaaatt  30300
ccatatccgg aattgtctac aggagcctct gggctgctcc caagggccca caccatgcct  30360
tactcacttt gggttgccat ccaaacatgt ctcatgacaa agaagctcaa acatgtgcat  30420
ggacagtgcc agaaaacaag ggtcgtacat agacaaaata aaatgataac gtcccacaac  30480
catttctttg atacacactg tttctctcag tcctcccaac cacctaggta acaggcaggg  30540
aaggtgttac tgttgcctgt taggaaagag gacagccctg aaagctgtcc ctggccactg  30600
aagcaaccca ggtcttccag ccccagggag agccgccttt ccattgttcc agacaaagca  30660
gagacaggca tgggggagcg ggagagggac tcctgtgggc aggaaccagg ccctactccg  30720
gggcagtgca gctctcgctg acagtccccc cgacctccac cccaggcacg ggctgcaatg  30780
cctgctacat ggaggagatg cagaatgtgg agctggtgga gggggacgag ggccgcatgt  30840
gcgtcaatac cgagtggggc gccttcgggg actccggcga gctggacgag ttcctgctgg  30900
agtatgaccg cctggtggac gagagctctg caaaccccgg tcagcagctg taaggatgcc  30960
cccctccccc acaacccagg ccctgggccg ctctggtgca gcggcagatg ggagccgggc  31020
cattgcagat aatgggcttg tttttaaaca actctgggga aaagcaaact gacaatccgt  31080
tcgtaagctc catcccttct gctcagtcat gacctgcccc tgtgagagat gaagggttag  31140
tcccagttgt gatgtgataa gcccagacct ctttccttcc gacaggtgat cgtgcatgca  31200
gaggaggctc tgagacgccc ccagcaaggt tcctgggttt aacccaacat tccccaaagt  31260
```

```
atgtatttgg ccacattcac agaaagaata ttagtctttt gtggaatgct gcgggttgac  31320
agtcacagct tggaaaccaa cccacagaga gctcatcatt aatcatggct atcacttgtt  31380
taccacctac tgtgccaggc ctatgctaat tactttatta gcgtcctctc tgccgctcgc  31440
aggcctctat tattataggt cagtagtatt cgatttattt aaattaaata cggaaggtca  31500
tagattaagc aagaaagtgc cagcaacatg gtgcgtgcct ctgactgggc actaaccctc  31560
caagtcttag ttttcccaac cataactggc caatgaacag cagctctgga tgcagctaaa  31620
ggaagactga agctgtaggt cccgtgctcg gcgcagggcc ccctgcaagg aaggtttcgg  31680
agggactgga tggggtcttt gaactatctg tctttccctt tactgcagtg ggcccagggg  31740
caggccaaag ttgctcccgt gattgacttg aacgtgcacg ttcctaatcc ctgacatttc  31800
taaagctctg gctcattaac gagggaaaga cgtgaaccag ctgggggagt ggggatcgca  31860
gtgccccacg tggccgcctc gtgacctcag tggggagcag tggggccggc tcccggcttc  31920
cacctgcatg aggggccctc cctcgtgcct gctgatgtaa tggacctgcc ctatgtccag  31980
gtatgagaag ctcataggtg gcaagtacat gggcgagctg gtgcggcttg tgctgctcag  32040
gctcgtggac gaaaacctgc tcttccacgg ggaggcctcc gagcagctgc gcacacgcgg  32100
agccttcgag acgcgcttcg tgtcgcaggt ggagaggtgt gcggaggagg agggtgggtg  32160
caaagggcag gggctgggga cgcccgggca ctgcagactt ggtctcaggg cgacgctgag  32220
tcccaggccc ggggcgcagg gatgggaaac tagggcctgg ggcgggattc cgggcgtggg  32280
cggggcccgg ggcggggcac agggggcggg ggagtgggcg gggcccgagg ccgggcgctg  32340
gaggcgaggg cggggcaggg acgggtccaa gggcaggagg ctgggacagg acggggatgc  32400
aaagggaggg gcggggcccg agacggggag gaggggggagg gcccaagggg aggaggcggg  32460
gtccggacgg ggatgccaag agcagggatg ggagcgagcc tgcgtccggg cactggtccc  32520
catccgtgag tcccctcggt gctccctgcc cgccgtggcc atcctctcac atcactcaca  32580
accccaaggc gcggcatggt tgacaccccc acgttaggac ggagaccctg ggcttagtta  32640
gagggggcag tactaaccag tccctggcgg aaacgctttg gctgggtgag gtgagcggga  32700
tcgcccccat ttctccagag aggggtcccg gctcagcgag ggaaagaggc cgccgctggg  32760
gggacggctg gccggggccc ctccctggag aacgagaggc cgccgctgga gggggatgga  32820
ctgtcggagc gacactcagc gaccgcccta cctcctcccg ccccgcagcg acacgggcga  32880
ccgcaagcag atctacaaca tcctgagcac gctggggctg cgaccctcga ccaccgactg  32940
cgacatcgtg cgccgcgcct gcgagagcgt gtctacgcgc gctgcgcaca tgtgctcggc  33000
ggggctggcg ggcgtcatca accgcatgcg cgagagccgc agcgaggacg taatgcgcat  33060
cactgtgggc gtggatggct ccgtgtacaa gctgcacccc aggtgagccc gccccgctct  33120
ctccctggta aagtggggcc caaaaagcgc gcgctccaag gttccttgcg gttcccaagc  33180
tccaagattt cgtagtcctc ttctcgtccc ccttggccta gatttggggg aagggtcgac  33240
tgcgtgcagg gcgcccggta atgaatgtgg aggatgaggt gggaggaggg acggcagccc  33300
tgcttctctt ctgcccagct tcaaggagcg gttccatgcc agcgtgcgca ggctgacgcc  33360
cagctgcgag atcaccttca tcgagtcgga ggagggcagt ggccggggcg cggccctggt  33420
ctcggcggtg gcctgtaaga aggcctgtat gctgggccag tgagagcagt ggccgcaagc  33480
gcagggagga tgccacagcc ccacagcacc caggctccat ggggaagtgc tccccacacg  33540
tgctcgcagc ctggcggggc aggaggcctg gccttgtcag gacccaggcc gcctgccata  33600
ccgctgggga acagagcggg cctcttccct cagtttttcg gtgggacagc cccagggccc  33660
```

-continued

```
taacgggggt gcggcaggag caggaacaga gactctggaa gccccccacc tttctcgctg 33720
gaatcaattt cccagaaggg agttgctcac tcaggacttt gatgcatttc cacactgtca 33780
gagctgttgg cctcgcctgg gcccaggctc tgggaagggg tgccctctgg atcctgctgt 33840
ggcctcactt ccctgggaac tcatcctgtg tggggaggca gctccaacag cttgaccaga 33900
cctagacctg ggccaaaagg gcagccaggg gctgctcatc acccagtcct ggccattttc 33960
ttgcctgagg ctcaagaggc ccagggagca atgggagggg gctccatgga ggaggtgtcc 34020
caagctttga ataccccag agaccttttc tctcccatac catcactgag tggcttgtga 34080
ttctgggatg gaccctcgca gcaggtgcaa gagacagagc ccccaagcct ctgccccaag 34140
gggcccacaa aggggagaag ggccagccct acatcttcag ctcccatagc gctggctcag 34200
gaagaaaccc caagcagcat tcagcacacc ccaagggaca accccatcat atgacatgcc 34260
accctctcca tgcccaacct aagattgtgt gggtttttta attaaaaatg ttaaaagttt 34320
taaacatggc ctgtccactg ttctttgact tctgtgcatt aggactgtgg ggacaatcta 34380
taaagagtct gcgtcacatg catgaagaca cttcagtatc tcggcaatgc cctccagaca 34440
gctcctccag ccatctgtgc caaggggagt gtgaggagtg acagaccagg ctgtaggaac 34500
aggaatgggg tgtcatgggg gatggcagag cagtggacag tacactgcct ggcccgggcc 34560
cctgcttgcc tgcccatgga atgtgtgcag agggagtgcc aggccaggtg ctgctctgga 34620
gaagtggggg aatgaggctg gtcctgctgc aggtcagtct cagcaccgtc ctgtccagtc 34680
agagtcactt aggtttgcca gtgagtaggg gcccagatac atgttggatt tctaaggtcc 34740
ctccagatgc tcctgtcagt ggaacgccta tttagagtta gccaagcgta ggcataatgc 34800
catctttctg cagcataaaa tacagtgaca tagaaacata tttgtgtgat tttcatgcat 34860
tcctttttg atgagagata ttacccagct aattaggaac aactgttttg tttccttcag 34920
atcataaccc aaagttgtga ttttgaaaag tcatgtcccc cttcagattt cttgttttct 34980
gctacttctc atgtggaatt gctttggctc ttcttagttc tcttgagtct aaattattcc 35040
ttataagttg gtgcaagcat ctgattattt tgttatcatt actgttatgc tcaagcattc 35100
acagagtgga acacatttta atatcaattg ctttctattt ctcctttata ttacagttca 35160
ggacattgta ttaattatta aaattctatt cgtaggtagg ttatatgact gaattgaaat 35220
agataaaatg aatttctttt ctagataaca aaggaggtgt cataaaacac ttgttatggg 35280
ccagtgtgat ggctcatgcc tataatctca gtgctttgag aggctgaggt ggaggattgc 35340
ttgaggccag gaatttgaga ccagcctggg gcaacatagc aagaccccat ctcttaaaaa 35400
aaaaagggtg gggcgggggg gcactgctgg gcgcggtggc tcatgcctgt aatcccagca 35460
ctttgggaag ccaaagcagg tggatcaaaa ggtcaggagt tcgagatcag cctggccaac 35520
atggtgaaac cccaactcta ctaaaaatac aaaaattagc cgggcatgat ggcgggtgct 35580
tataatccca gctactcagg aggctgaggc agaagaattg cttgaaccca ggaggcggag 35640
gttgcagtga gcagagattg caccactgca ctccagcctg ggcaacagag cgaaactctg 35700
tctcaaaaat gaattaatta attaaaaaaa gaaaaaaaaa acactgggca gggtggtgtg 35760
cacctgtagt cccaactact ccagaggctg aggcaggaag gagcacttga gcccaggagg 35820
ttgtctgcag tgagctctac tcatgccact gcactccagc ctgggtgaca gagctcagtg 35880
gcttacacct gtaatcctag cactttggga ggctgaagca ggcagatcac ctaagatcag 35940
gagttcgaga ccggctggcc aacatgataa aaccccgtct ttactaaaaa taaaataaaa 36000
```

-continued

```
taaaaaatat atataaaaat tagctgggtg tggtggcaca tgcctataat cccagctgct  36060
tgggaggctg aggaacaaga atggcttgaa cccgggaggc agaggtggca gtgagctgag  36120
atcgcgccac tgcactccag cctgtgcgag agtgagactc tgtctcaaaa aaaaaaaagg  36180
gaatttaaga aatttaaaag aaaactcttg ttatataaaa agggtattgg gtctgacaga  36240
taagagctcc tgcactctac cagccagcta ctgacagaca taggtctggc tccagtggag  36300
gggcagcagc cagtgagccc agcctggggt ggcccactcc tgctgcctcc aggatgtccc  36360
ctgtttcccc agcccctctg ctgtgccctc ggccccagaa gctggcgaga ctgcttctct  36420
ggaacagcat cacgcaggcc tgcccatcgg cccactgtgc accaggcctt ctggggatac  36480
agatgtcaac caggtggggt gctcaggagg ggcacagaag ccaggaatga caaacacatc  36540
agccaccagg caaatgggaa atgtgcccca gaagctccct gctgaggatg ttagggagag  36600
cattctgaag tagtgtggtt gagatgaggc ttgaggaagg caaggctcca aacagcaggg  36660
cagactggga gcaaggtaga ctgcatggga gggcagctga tggagctcct taaccctctg  36720
gaattgcccc aaagccaagc aaagtgttct tcttggggtc acagctagct cagggatgcc  36780
ttctgcccct tggtcagagg ggcaaaaggt cagagcctag ggtcaccaaa acctctggga  36840
agccccgggg gtctcaggcc acagaccatc ctcagaacta cacactgccc tcccatgcct  36900
ggcgggggcc ctggactggc cctcaccagc tgtcttcttg cactggccag ggttctggct  36960
ggactggcaa ggaggggtgg tcagatacag gagtaactgg atcccttcat caggacctag  37020
ggtggtgaga gctttgagcc tgctctgctc caggcagaca ttgtgtctgg ccctgccagg  37080
atggatagac agcaggatgt tacacgttga ggacatgaag gtcatcagga atgtggctgg  37140
aatctgttag gcctccccca gcccaggcgg gggctgccaa gtttgggcct atcctctgtt  37200
cctctcctta tttggacctt caggtgataa ggctgagaca taaaggaggc tgggccctgc  37260
caccacgaca gcagccacac ctctgcagag agaatggtga gtgcctgctg gggaagaaag  37320
gctagcggtc tcccaggtgc tggcctttgg gctgggggag cagagttttc tgtgcttgtg  37380
ttgggttgag ggtggtcccc agggagagga agaggatcct ggccctggct ctcctgggaa  37440
tgctctggga ctgtgcatga tgggtggggt ggggagactc tgaggagttg gggagaggac  37500
ccctccctac tcacagtgtt gcaggccagc aggaaggcgg ggacccgggg caaggtggca  37560
gccaccaagc aggcccaacg tggttcttcc aacgtctttt ccatgtttga acaagcccag  37620
atacaggagt tcaaagaagt gagtgcccac tcccagtagc ctcagatccc atcctggccc  37680
ccccacccca ccccacatac ataccccccct tctaccctga ccttgcctct cacaccaccc  37740
aggtctctcc cccacctccc accttcccta gagctggggg ctgctcccac ctgaaggccc  37800
ccatcccaca ggccttcagc tgtatcgacc agaatcgtga tggcatcatc tgcaaggcag  37860
acctgaggga gacctactcc cagctgggtg cgtgcaccca cctcccaccc tgcgcactgg  37920
ggtccctact ctgagctgct gggcgggtgg gagtggctgg ggggacagga ctctgctccc  37980
ctgcttcccc tcctccccgt ctcctcacac tgcccttccc cccttgtcac gccttgcttc  38040
cacttcacct tcccgaccca cagctgcctc tgcccctcca gcccctgtgg ccaggatgga  38100
gggagggcgg cctgggcctt ctgggggaca cccagggtcc ctgtgtgcac ctcatgcccc  38160
acccccacca gggaaggtga gtgtcccaga ggaggagctg gacgccatgc tgcaagaggg  38220
caagggcccc atcaacttca ccgtcttcct cacgctcttt ggggagaagc tcaatggtga  38280
gcctgggaca gagctgggca cccttggcca ggcagggagc ctgcaccctg cctgaacccc  38340
acctgaaccc tgcctgaacc ccacctgaac cttacatgaa ccccacctga accctaactg  38400
```

-continued

```
aaccccacct ggacccacct ggactcttcc tggccatgac ccattccaag cacatcctct  38460
gccccagaat cccatgtgca ctggtcaccc cagtgctgac ttggagccag gaaatgtgcc  38520
ttcagccccc acccccaaat tccagtctcc cagccaagct gcccgcctca ggaggatgac  38580
cattcccagc cccactgatc cccgagaaac attttatgtt agggaatacc cccacctctt  38640
ctgggatgtg ggaggctcct catgcagccc agttcctcct gcgggggacc tgggatgctg  38700
gagacatgga tgctcacctg gctgcctcgg ccttccaggg acagaccccg aggaagccat  38760
cctgagtgcc ttccgcatgt ttgaccccag cggcaaaggg gtggtgaaca aggatgagta  38820
agtatgggcc cagccagatg aggagcaccg tggtggaagc agagagcggg gtgaggcccc  38880
tagtgagggg ggctgcctgt gcttcggggc cttacactgc tctttggggt gcagccaacc  38940
cttccctgcg ccatgggagc ctccgtaccc accttccctg tgcagtcact cccccgcagt  39000
ctcctgctca gaccctcctc accccccagg ttcaagcagc ttctcctgac ccaggcagac  39060
aagttctctc cagctgaggt gaggctgccc agccccttca atactcatcc ccagcacctt  39120
ctctgggcct tcacccatga cccagagccc agtaccagtg aggcagttgc tggaagggtg  39180
agccgagggc ccttctggag gaggtgccat ctctgttgag acctagaggg taaagatgtg  39240
gagtcagaaa agagggcagg gtgcgccagg cagggagact gtgcacagac ctggggggaa  39300
gtggataggg agaggtttcg tacactcggg gtgggcctgt gcctgtggct ggaggggcgt  39360
cctttgcctc ttggcccaca tttgcactga ctcctcactc tgcccagagt cagccaagag  39420
aaaaacatta acccagagtc tggggtctag ggttgaaaag ctaaggcaaa aagcacagat  39480
gcagggggca gacagaaagg ccacaggact caggtgaggt ctctgccggg ctgggccagg  39540
agccagggga ctgccactca ccagtgtccc ctgcaggtgg agcagatgtt cgccctgaca  39600
cccatggacc tggcggggaa catcgactac aagtcactgt gctacatcat cacccatgga  39660
gacgagaaag aggaatgagg ggcagggcca ggcccacggg ggggcacctc aataaactct  39720
gttgcaaaat tggaattgct gtggtgtctt gtctgtgaca gatgggttgg ggaccagcca  39780
agggggatcc cagggtctca gtgcgcacat caccatgatc atggccacca tctacctcct  39840
gggagctggc ccctcgccag ctcaccttga ttcactccca tgatgccaag tgaagtgtga  39900
actatgatca tgcctagttt acagatgagg acactgaggc ccagaaagtg tgagcatctt  39960
accaaggcca gccctctaga agaggagatg gtgggattta caccacctcc accaagccca  40020
ggaatgagcc acaaagtggg cactgcccag ctacttgggg ctgtgcagag aagaggctgc  40080
ttgctgggca ctcagcaaac tctgcccaac agcccagcgg gtgggcagca gccctgggac  40140
ccccacaccc aaccacacag cctcccctgg cccactgctc gcaccccatc tcaatacact  40200
ggcttgggtg cctccctgca tgggcccttt gtgaaaggca gagaggtacc catttgaaac  40260
acaaccagct tctcattgca aatacaggca aggcactaag acatgaggaa catggacacc  40320
aaagcagggg ccaggtaaca tgcaaatttc tagaggaaat gcccagaacc tggcatcatg  40380
cctcctgagc ccctcatgcg ccgtgagggg taagagggtc agacagctgg agtgtaggga  40440
gacgacttct caggagagaa tagttagtgc tcccgtcacc cttcatctga gaacccaaga  40500
gctagaggag aaagtgatcc tcatgagtac cagaggagca gcaggggaca tccaaagcac  40560
cagagagaga aacagagaca gagagacagg cagtgacagc tcaaacctca gccagatcca  40620
gagcatacaa agtctcctgc ctacaggaca gcccagtaag agctctcagc ttgcctcctt  40680
ccctccccac aagccctgct gcaatccctg tacctggggg tcagtgggaa ggaggtgagc  40740
```

-continued

```
gagaaaggag gggcacccct tcctgaaggc cccaagagga aaggcgtttt cacccagaca  40800
ggtgttcagt tttgatttta tctggcgcct ggcaatttaa ttactaaatt gaaacttgag  40860
actttctgga attatggcat tttctgttgc ttagagagat tacaaaagtc acgaactgcc  40920
tgagtttcca tcctgaaagc aggccaccag cccactccac tgaccatgct ggaacagtgg  40980
atgaacaaaa tcaagtacca ttaggattct accacatgag tctgcttgtt caacaagctg  41040
atttcataaa gtaagggatc atgttataat ccaagctcta caggggtaaa ttgtgaaaga  41100
ctaaaatgaa ccaaaaagat cataggtgtc cagttatctg atttgatggg gtgtctgaac  41160
cttttgttat ctttgagctg tttcaaaact ctctaaatta ttattattat ttttgagaca  41220
gagtctctct ctgtcaccca ggctggagtg cagtggcatg atctcagctc actgcaacct  41280
ccacctccca ggttcaagtg attctcatgc ctcaccctcc caagtagcta gtattacaga  41340
tgggcacacc ttgcctggct aatttttgta tttttaatag agacgtggtt tcaccatgtt  41400
agccaggctg gtctcgaact cctgacctcc gttgatccac ctgcctctgc ctcccaaagt  41460
gctgggatta caggggtgag ccaccgtgcc ctgccacaac tctaaattat aactaatagc  41520
aaggcaatgg ttcttctcta ttaacgtgca aataaatgtt gtccagtgga agcacaactg  41580
atttttccct tctctgtgga agaagccaat tttgcatcta ttaagcaaat tcatctgggc  41640
attcctaacc gtctacacat gcaccggctc tttgaattct tctctgaacc aggcccagga  41700
ataagccaca agatgagcac tgcccagctc cttgggctgt cacatcttat tgattcccac  41760
atgaattcac aagtaaataa aatatttggc ggttgttcac ttagtatgca agtcaatatt  41820
ttgctttaaa aatattatcc tttcacactc ctgatatagt tgtctgataa ggttagtcct  41880
tcccacacca aaactgcctg tattagtgtt gtttggaata aactgagggt agaatgtata  41940
tggtgtgtgt atgtggtgtg tgtgtttgtg tgtgtgtgtg tgtgagagag agagagagac  42000
aaaagagaga gacagaagga tagagagaaa cagatgggca cagacccagg acatgagttc  42060
agcctacact gaccaatatg acagccactg gccacttgaa atgtggtgtg agttgggata  42120
tgccaaaagt gtaaaatgca cacaatattt tgaagatttc atacaaaaaa gaatgcaaac  42180
atctcattaa taacttttat atagatcaca tgttgaaatg ataatgtttt ggatattaga  42240
ttattactaa aattaatttc acctatttct tttcactttt taaatgtggc tactagaata  42300
tttagaattc cataagtggc ttgcatttct ggctttcact cctgttggaa agcactgagt  42360
tagactgtgt agtacgtcta tttaagactg cagtttccag gccgaacacc gtggctcacg  42420
cctataatcc cagcactttg ggaggccgag gcgggcagat cacctgaggt caggagtttg  42480
agataagcct ggctaacgtg gtgaaaccct gtctctacta aaaatacaga aattagccag  42540
gtgtggtagt gcatgcctgt agtcccagct actagggagg ctgaggcagg agaatctctt  42600
gaacccagaa ggggaggttg cagtgagcca agatcaagcc actgcactcc agcctagatg  42660
acagagcaag actccatctc aaaaaaaaaa aagtagaata aaaataaata aataaataaa  42720
gactgcagtt tctgggagac tctgaggcag gcattagcct tctctgcaga gagtacttgc  42780
agcagggagc agcagttttg atgtcctcaa aaggagccaa tttcatttgg gtagggttgc  42840
ctctgagtat tctagcagta cagacagaaa ggagagaagg ctgtttccag aaagcagaga  42900
tcatacgaat tacttgtgag accaaacttg ttcctcaggt gaagctcagg catcccttat  42960
gtggagtgtc taacagtcta cacctgagga tgttggacat aagggggtgt gaggtgggca  43020
tggctgggga gagctctggg agggggaaaa ccagctccat gttgtccacc cactgaaagg  43080
aaagctccct ctgggggagg tagatgcccc ctggccaggc ctgcagggcc ctgctcactg  43140
```

-continued

```
tgagccctgt gtggtcctgg cctgggtccc accagccatt gccaggcaac agctcccagt  43200
tggaaaacag agcaaggctc cctcttagaa aaaaaaaaaa gaaagaaaga aaagaaaaga  43260
aatacaacag gtaactaagc atgacggctc acgcctgaaa tcccagctac ttgggaggcc  43320
aaggcagagg attgcttgag actgggaggt tgaggcagca gtgagccagg attctgcaat  43380
tgcactccag cctgggtgac aaagtgagac cctagtaaaa aaaaaaaaaa tagagacaga  43440
gaaagaaaga catgcaacag ggccaggcgc agtgactcat acctgtgatc ccaacacttt  43500
gggaggcaga gaagggagga ttgcttaaga ccaggagtgc aagaccaacc tgggcaacat  43560
ggcaaaaacc catctcttca aaaaataaaa aaattagcct gttgtggtgg tgcgcaccta  43620
tagtcccaga tattcaggga gcttgaacca ggtccaggct gcagtaagcc atgatcgtgc  43680
cactgcactc cagcctgggt gacagagcga gaccttgtga gaaagaaaag aaagaaggga  43740
aggaaggaag gagggaagga gggaaggagg gaggaaggga ggaaggaaga atataggacc  43800
caaaggccta aatgccccta ctgtgcccca gttctgcgtg actcaggacc agcctcctcc  43860
acactcccac caccacaacc ctgcacccta cttgttcctg gggccccaa ggggagcctc  43920
accagaagcc tcctcataaa cccactgccc cttacctttc ctgtctttct agaagcctca  43980
gaagccttgc cactctaagg acacctccat ctgagccaag gcgctcgctc cagatgtccc  44040
agagctcctg gtcctgggtg tccctgccac acaaccccc atggagccct gctctggctc  44100
aagcccctg actgtgcatg agcaggcctg ttgccctcac tgggactgtc cagagccttc  44160
ccatctctct ggagggactt ccatcagttt ctgccccttc tcctctgcca agaactcacg  44220
ttcagtctga tagcagaaga atcatctggc accctcctga atggaaccca gagtacctcc  44280
tttgtggacc ggtctctgga ttttccccac tctctccctt cagccatgct gatggcagag  44340
aaggtaagaa cttccagccc acttctctgg cgaggggaac ttgtcatctg ggtctgcaga  44400
gaaggttcca ccttatgctc atagtacatt atctttacta tgtactagga tatcacattt  44460
aaaaggacaa aaaaggccag gcagtggctc atgcttgtaa tcctagcact ttgggaggct  44520
gaggcaggtg gattacctga ggccaggagt tcaagaccag cctgaccaac atggcgaaac  44580
cccatctcta ttaaaaatac aaaaattagc tgggtgtcgt ggcatgtgcc tacaatccca  44640
actacttggg aggctgaagc aagagaatca cttgaaccca ggaggcagag gatgcagtga  44700
gctgagatcg tgccactgca caccagcctg ggcgacaaac cgagactcca tctcaaaaaa  44760
taataataat aaaatacaac aaaataaaag aacaaaaaaa aagaaatgta aaatacttga  44820
aggggcttgt ataacattaa taggattgac agtatctgct ttccaggctg aagtgattca  44880
ttcattattc tagacgtctt tagtcctttg caatttgtgg taattaggct tttcttttta  44940
acattaaaaa tatacaaaaa taaaaggcaa aaaaagcatc atcccattag tctgaccttc  45000
ccctcctcca tccctgcccc aacaccctga agaccctgga tgcaaacaaa ggcccgaggg  45060
agcctcttcc ctcgcagtgc aggcctcacc tggggctcag agtcagaatc tgcattttat  45120
tccctaggac aacctctagt cagggcagag gccggctgtg ctgcccaagt gccctaaccc  45180
tagctttgag gcaccagaag ggcaaatgca aattaaaaat gagaataagt ttattctcct  45240
tggtgaaaaa aaaaaaaaaa gactttcccc tctccttttt ctttagaaaa tctatcattg  45300
caagttcctt cctggacttt ttttatgtag atctgttcaa aagctaaata agcctctttc  45360
aagtttcaca tcccaggaat gtctccttaa ggacctagga gccaccattt gaagtgtaat  45420
caccaaggga gatacatcct tatctcccag tttccgtggg caaaggggag cctaacttta  45480
```

-continued

```
gcccggtgcc tagctcaagt tgcaaacaca cttccagtct taaaggaatg aatttatttt  45540
ttttccttta ggcaaaccca ggtagccacc acagttacct ggggattcac agagaactgt  45600
gtgtgaccac tggtgctgtc aagtcctctt acctgagcac ctgtgacgtt tcccttgaga  45660
acgtgtacgg gatgggttgc acctggttat atacaagcgt gagacttctt tctgcctttg  45720
taatttatta gcagattatc tgtgatgagc atcgcaatct gtttaatgcc tattcaataa  45780
ttaaattttt ctttctcttc ttttgtggaa aggttttctg cattggcagg agatttttgt  45840
tttcgattat gtccccaaca tgcctgatgt tccacccctc aagagcctca gccttgccca  45900
gggagggcat gggggtgagt ggcctctccc acagagagtg ctggccaagt tggcccaggt  45960
gcgcagcaag ggctgctgcc                                              45980
```

<210> SEQ ID NO 7
<211> LENGTH: 18999
<212> TYPE: DNA
<213> ORGANISM: Homo sapiens

<400> SEQUENCE: 7

```
ccctcctcca tccctgcccc aacaccctga agaccctgga tgcaaacaaa ggcccgaggg     60
agcctcttcc ctcgcagtgc aggcctcacc tggggctcag agtcagaatc tgcattttat    120
tccctaggac aacctctagt cagggcagag gccggctgtg ctgcccaagt gccctaaccc    180
tagctttgag gcaccagaag ggcaaatgca aattaaaaat gagaataagt ttattctcct    240
tggtgaaaaa aaaaaaaaaa gactttcccc tctccttttt ctttagaaaa tctatcattg    300
caagttcctt cctggacttt ttttatgtag atctgttcaa aagctaaata agcctctttc    360
aagtttcaca tcccaggaat gtctccttaa ggacctagga gccaccattt gaagtgtaat    420
caccaaggga gatacatcct tatctcccag tttccgtggg caaaggggag cctaacttta    480
gcccggtgcc tagctcaagt tgcaaacaca cttccagtct taaaggaatg aatttatttt    540
ttttccttta ggcaaaccca ggtagccacc acagttacct ggggattcac agagaactgt    600
gtgtgaccac tggtgctgtc aagtcctctt acctgagcac ctgtgacgtt tcccttgaga    660
acgtgtacgg gatgggttgc acctggttat atacaagcgt gagacttctt tctgcctttg    720
taatttatta gcagattatc tgtgatgagc atcgcaatct gtttaatgcc tattcaataa    780
ttaaattttt ctttctcttc ttttgtggaa aggttttctg cattggcagg agatttttgt    840
tttcgattat gtccccaaca tgcctgatgt tccacccctc aagagcctca gccttgccca    900
gggagggcat gggggtgagt ggcctctccc acagagagtg ctggccaagt tggcccaggt    960
gcgcagcaag ggctgctgcc caaaggctcc ctcctggttg gcatgggtcg ggaccctgtt   1020
gtgttgtgtt ttcgctcttt ttcgtagagt tcaagggggt cctgctatgt tgtccagact   1080
ggtcttgaac tgacctcaag ggatcctctc gtctcagcct cccaaagtgc tgggattact   1140
gtgcccagct ttgtgttgta ttttctgatc ttatcctgca acctcttgag cccccaacct   1200
gggccccagt tcctgctgtg ccccagcctg ccagccctct ctctctgcat attctttctt   1260
tagctgagtt aacaccactg ataaggttaa agacaggctc ttaaatttct gccctggcat   1320
gagaaatatg tgacccacat gcttctccag cttagctgtc cagtgtaact gtcagggact   1380
gatgggcgcg tgctggccca cagcccacct cagtcctgac cctccctgac aggctgagag   1440
aggccccagc ctgaacctgg actcccccat gttctgatat tcctgcacaa gagtgcagag   1500
gcctggttaa gctggagaaa cataaggaat aggtaggtct gcacacactc acctcttcct   1560
ttgcagtgaa ccttctagaa tcttctagat ggaaaagctg gggggtgtgga ggtgtaggga   1620
```

-continued

```
taggacagct gggggaggcc ttggccaagg tcaaggagta ggcccagtct ccctctctgt   1680
gtgcctgtct gggactcggt ttcctgtctg tgaagcaggg ctggacggga tattgacagc   1740
acctgatggt cattgagctc ctctgcccca ggcactcagc tgctgggcac agtgcacacg   1800
tggcagtccg gtgccctctc acgctccgtg atgactgagt ctgtagttac acccctggcc   1860
tcagaataaa gactacactt tctgcctccc tcactggcag gtatgactag gtgtggtggc   1920
agttttctcc ttaagagaca gatgtttgtg cctccctcca acccgctggc taacacctag   1980
ctggcacaca gcctcctggg gctatgaaga tgagggccac agccacaggg tgggggagcc   2040
gtgagctggg tctggctgcg tctctgacat atgggggcat cacacatcac ctctacctcc   2100
catcgaatgc tacacgaaga gaacaaactc cacctgatgg aagctgctgt tgtttgaagt   2160
ctttcatgct cacaacagaa cctaacccca accaatacag tatgagtatt ggccccacgt   2220
ggttaagcaa gctgtccaag gttacacaca gctgggaggt ggtggagctg ggtttgagcc   2280
tgttattgac ctttgtgcag acagacctca gagcagagca caaggcagca aggctgtggg   2340
tctggggctc cctctccagg agaatcaact ggctgcacac agcctggaga gcccatgggc   2400
aacctgagtc cttgcacctg gaagtttctg tgtcccacac atatccagga gcttaaaatg   2460
aagatgtctg aattacccaa cctcttgata gcaccaaccc aaccttccca gcctcctctt   2520
ctgaggtcag cccagagcaa gccccttgca aagctgattt aactcagaac cactgggcat   2580
acccacaggg cagtgaccct gcagccctcg atcaaatgtg cagatggact tgggggtggg   2640
ctggtacccc agatggcctc attctcccag ggttgcagag cccctgaaag ccacagccct   2700
gtgtgcacac cactggggag tcatcacagg atacttcaag aattcagtgc caggcaaggt   2760
ggctcatggc tgtaatccca gcacttcggg aggctgaagc gggcagatca cctgaggtca   2820
ggagctagag accaccctgg tcaacatagg gaaaccccat ctctactaaa aatacaaaaa   2880
ttatctgggc gtggtggcgg gtgcctgtaa tcccagctac tcaggaggct gagaccggaa   2940
aatcgcttga gcctgggagg cagaggttgc agtgagctga gattgcactg ctgcactcca   3000
gcttggggga cagagtaaga ctccatctca gaaaaaagag ttctgtgtat catttaatgt   3060
ggagatcctc ccatcacgag gatgaggctg tttctctact ccccagatct gggctggcct   3120
gtggtttgtt gacctcagcc ttgtagttct cactttcctg gaacctgaat gccaccacgc   3180
gacatccata agacaaagcc caggataaaa gatcacttgg agagacaggc ctggcctggc   3240
accaccccgg ctgaggctgg accccctggga aggagactct gatggacctc cagacccagt   3300
caaatgacca cttccaaggt caggcaagaa gggacaaaga gccactggct cagcccacag   3360
catctgagaa ataagaaacc gctgcatttt ttgagccagt aagatttgac aggtttgttt   3420
tgcagcaata gatgagtggt acctcatctt agcccatgtt ctgatgaaga caaacagtag   3480
cattgacaaa gttttaagaa aagttaacca aaaactggga ttcctttctt cattttgacc   3540
ctttgttaca agaaacagag gcccacccca ccagactcac tgttcactgg tccctgagtg   3600
cctgtgagtc tcagtgggag ttaccttgag accagccctt ctgagtggag ggtgctgggt   3660
gctgaggtca agtcgagctc agtccaggct aaaaggagag cagctctggc caggctgtca   3720
gggctgtggc ctccccaaga acctcctacc ctggcccctc caggctttgc tgctatggtt   3780
gtgtgagggg agttgctgtc ccagcattct ggcccccttg cccccagccc ctccctgacc   3840
tccacgggct tcaggcctca gtccagagtc acctcctcta ggaagccatc ccccagtgca   3900
agtctgggca acattcctcc ttgcctggcc cacctgctca ctctcatgct atggctttct   3960
```

-continued

```
gtaagcaaac acaaagatag gaacaactct gtccctggca cagagcagat gctctggcaa   4020
tatctcatga gtgaatgaag gcacatgaca aacctccaga cctgtggaga ctgaaggctg   4080
agagccttta tagatgctgt ggggccgagg agtttgccaa ctacagcagg tcatgcccag   4140
aggtttctct ctgggtagca aggtgtgtct cccaccaaag gccattggca tggggcccgc   4200
cctgctgacc cgaggcagtg cacagcagag gccagatgca gtgagaagga gcctctcctt   4260
ggcctgctgt ctgctgccat gcctgtgggg gcgtggacac aagtgtgtgg catagaaggt   4320
ggtgtggcag gtgagaggtt gggggtgtgt atgtagcagg tgtctgtgtg tgtatgtgca   4380
tgtgggggtg tgtgtgcatg catgtgtgtg tgtgcatatg cacgtgtgtg catatgcatg   4440
tgtgtgcatg gagagagaag acctcctctt tctggcccct ctcctagctg ccccccctccc   4500
tcctgctgcc aacacactgt caacccttca ctgtcttttt ccttgggact cgttgatctg   4560
tctctaccat cccaggtgtc tggagcagcc tctaaccttc catctgccaa ggtacttcag   4620
ccccacccct cccagctgtg gaatgtcccc taggatgtgc cactgacaca aagagccaca   4680
cagctccaaa atagaatatt atctaaccca ctgctccctt tgctgtcagc aacacctcca   4740
ccatgcttct cccaggaccc cccttgaact ctctgcttcc tccctgaggc caaaggaaag   4800
acaggaaagg ggccaccttc ctgtccttgg gtcccacaga gatgtatcct tgtaatgaaa   4860
cctactttat gcttgagttg tatccagtta gtttctgtgg cttgcaatca agacccacac   4920
ccacctcaac ccaggctcta gagagtagac ccttgttttt gcctggcttg ggtcgacctg   4980
gcacctgcca gggtcccagc ctctgagtca gcccaccttg ccctcatcgg tgccacctcc   5040
aggcggctgt acatagactc tggcttctgc cctggcctgg cctctgggaa ctgcagctgt   5100
ctgcttccat cctatgtgga tggtgcctga aagtgaatag ggatcagtta ccagcccagt   5160
atctgtcccc ttctcaatag cactgattcc tatggggaac tgcttttctt ggactatgta   5220
tgggtttggt gggagggtag ttcctgtaac caaccctaca gggtgtagga acctagactc   5280
tcagcaacat aacaggcagc aggctcccaa gctaagtctg gccagctggg ccacctctcc   5340
cagattctgt ttcatgagag catcatccaa gagcagtggg aacactgggg acggtccagc   5400
ctaggactgg tatgcagatc agagaatccc agatagaagg tgattgctgt tcttccagtt   5460
tcttggccct ccagagcaac catacttccc atctgcccca aaacctgatc ctccaaactc   5520
ccaccatttc tgtgcatccc caatatctaa tagatcaact gcctttcatt tacatttgtc   5580
acaaccaaat gatacacctg cccttcaccc actactgaac tgcagctggg ttagtccaaa   5640
ttcagggccc acgtgtcatt tcaagcctgt cttgaataat gtacaccttc ctgcaatgtg   5700
aggatggcca ccaccttggt cttataccca cgggtgtcct gagctacatt tctcataatc   5760
aaaaataaac tcaacacatc actccagcct gagcaacaga gcaagacact agctctaaaa   5820
ataaaaaata aaaacaaaca aatgaaaaac ccagcaaact tggggaaaga ggaagcacct   5880
gatttccaga gtttccacat catgagatgc aaatgtccag ttttcaacaa caacaacaac   5940
aacaaaaaaa aaatcacaag gcatacaaag aaataggaga ctaagaccca ctcaaaggaa   6000
aagaataaat aagcagaagc cataccagag gaaaaccaga tggctgactt actagacaaa   6060
tactttaaaa caactgtctt aaagatgctt gaagagctaa aggaaaatgt gaacaaagtc   6120
aagaaagtga tggaacaaat ggaaattcca ataaagtgat agaaaacttt ttggagtttt   6180
ttttcttggt agcaaaaaat tatgaagctg aagaatacaa taaattccct agagggcttc   6240
aaaggcagat gtaagcaaac ttggccaggt gcagtggctc atgctcataa tccagcactt   6300
tggaaggctg aggcaggagg attgcttgag cccaggagtt tgaaaccagc ctgggcaaca   6360
```

-continued

```
tagaaaaacc ctatctttaa aaaaacttat ataaaattta aaaattataa aatttattta   6420
aaaaatcagc aatttgaaga ctggacaggg aaattatcaa atttgaggaa cagaaaggaa   6480
aaagatggaa gaaaaataaa cagagcctaa gagacctgcg ggacaccatc aagcagacta   6540
atacccattg tggaaattcc agaaagaaaa gagagtgaag gaccagagag attattagga   6600
gaaataatgg ctgaaaatgt ctcaaatttg atgaatgaca tgaatatgaa cattcaaaaa   6660
tctcgacaaa ctccaagtag gaaaaactca aagatactca tactgagatt catcataatc   6720
aaactgctga aagccaaaga caaggagaca atatcaaaag ctgcaagaga gaagtgactc   6780
atcacataca agggatcttc aaaaagatta tcagatatct tggctgggca cggtggctca   6840
cacctgtaat cttagcactt tgggaggccg aggcaggtgg atcacttgag gtcaggagtt   6900
tgagaccagc ctggccaaca tggcaaaaac ccatctccat taaaaataca aagattggtg   6960
aggcatggtg gtgcatgcct gtaatcccag ctactcggga ggctgaagca ggagaatcac   7020
ttgaacctgg gaggcggagg gtgcaccaag ccaagatcgt gccaccactg cactccagcc   7080
tgggtgacag agtgtgacct tgtttcaaaa aaaaaagaaa aagaaaaaga aaaaaaagat   7140
catcagctat ctcatcagaa acctcagagg ccaaaaggca gtagattgat atattcaaag   7200
tgctaaaaga aaaaaataaa tctgtcagct gagaatcctg tatctgtatc tcacttaacc   7260
attattttaa aataagggaa aatgaagaca ttcccagata aacacaagct gagggagttc   7320
attatcacta gatctgccct gcaaagaaag ccaaagaaag cctttcagga tgaaatgaaa   7380
ggatactaga cagtgactca aagctgaata aagaggccag gcatagtggc tcacacctgt   7440
aatctcagca ctttgggagg ctgagatggg cggatcacct gaggagttgg agaccagcct   7500
ggctaatatg gtggaacccc atctctacga aaaatacaaa aattagccag gtgtggtggc   7560
acatgcctgt aatcccagct acttgggagg ctgaggcaag agaatcacct gaacccagga   7620
ggcggaggtt gcagtgagcc gagattgtgc caccgcactc cagcctgggt gacagagtga   7680
taccctgtct caaaaaaaaa agccgaataa acgaataaag atctcatcta tggccgtacc   7740
accctgaatg tgtccaatct cagaagctaa gcagagttgg gcctggttag tacttggagg   7800
ggagaaataa cggtctatgc taaaggaaaa ttcaggtgca attaaagtaa aattaattat   7860
ataaaagaga atacattaaa agctagtatt attgtaactt tggtttgtaa ttccaccaag   7920
tggaatttgt tcctgaaatg ctagaatggt tcaacataaa aatcaataaa tgtaatagac   7980
cacattaaca gaaaaaaaac ccacacggtc atctcaattg atgtcaaaaa agtatttgac   8040
aaaattcaac actcttttga aagaagaaaa agctcaacaa actaagaata ggaggaaact   8100
acctcaaata ataaaatcca taggccaaat ccccaaactc acagctagca acatatttaa   8160
tgctaaagac tgaaagcttc ccctttaaga tccggaataa gacaaagatg cccactttca   8220
ccacttctac tcaacatagt atgggaagtt ctagccagag taatcaggta agaaaaaaga   8280
aataaaaagc atctgaattg gaaaggaaaa agtaaaatta tttgtttgcc caatacatgt   8340
acaatgtttc aggtgaaggc tcagaacagt acaaccttac cagcaagagt cctgctgtct   8400
ctgtgtgaat cccagctatt actcactagc tacatgatct ctcttgccct ccctgcctca   8460
atttcctcat gtgtaaagtg ggagaaaaat aatagttcat gcttcaaagg tttttttgttt   8520
gtttgcttgc tttgagacag cgtctggctc tgtcgctcag gctgaagtgc agtggtgcaa   8580
tcttaggtca ctgcaacctc agcctcctgg gcttaagcga tcctcccacc tcggcctccc   8640
aaagtgttgg gatacaggcg tgaaccactg tgtctgaccc aaaggattat ttgaggagca   8700
```

-continued

```
gatgaattaa tgtgtcataa cctcaaagca gttgcaaagg cgtttaataa ttaaaatatc   8760
acattttaaa ttaaaatata aggctgggcg tggtggctca tgcctgtaat cccagcactt   8820
tgggaggctg aggtgggagg atcacttgag cccaggagtt ccacactagc ctgggcacca   8880
ttgggagacc ctgtctctac acacacacgc acacacacac acacacacac aaacttaaag   8940
tagccaggcg tggtgctgcg cgcctgttgt cccagctact cgggaggctg aggcgggaga   9000
atcactggag cctgggagtt cgaggctgca gtgagccgag atcgcaccac tgcactccag   9060
cctgggccac agagcaagac gctgcctcaa acaaacaaac aaaaacaaaa attaaaatat   9120
taagtaataa ttaacgagtg ttaatatcca ctcgttgtgg agacaagacc tggacttagg   9180
aaacaggccc agggaagtag cagaacagta gcgctagagg acgcctggga gaatcagcgc   9240
gcggcgggaa gagcccggga agcttagtgg ggaagcgtct cttgatgggg tgaggaattc   9300
tataaattag tggagatgga aaaaaaaaaa aaaaagtatt cccaaagtgg gagacagcac   9360
tcagaaagac gtggtggtaa gaacgagtat gagtaacggg gacaacgagg acactggaga   9420
ttggggagtg ttgggctgga agctggtgtg cagctgtggg caagctaggg aggaccccga   9480
aaccgccaat gcgtttcccg gacgcagacg ctggcaggac gggaggaacc ccgagacccc   9540
gcgccatccc ttcaggaaga gttacttctc cccggccaag ttagtgggcc ttgggccttc   9600
tttctgttgg gatcctcctc gcgtgtcgcc atcgctacaa gtgggcagct ctgcggggaa   9660
agctgggacg ctgggggctt caccaaggag gctggcggcc gaccactggg aggtctggcg   9720
gggtgacgac cactgggagg tttgggcagg gcctgacggg gtgacgcggt cagcccactg   9780
gaggccgaca ccccccgtca gcccaacccc tgcacgcgcg gccgccaacc aaagacccgc   9840
ggcgccggcc tgcgagcccc cgccccgcgt tgcccaggaa accgagggtg tggctccgcg   9900
ttctctgggc gtcccaggga ctgggcgcac agtggtcggc gggatgaggc gcctggtgac   9960
ggacggggcg aggagggcag cgattggtga gattaggcga tgggcgggga agccgcgcgg  10020
ggattagcga gttgcggcga tgggcggggc aggcgcgcgg ggattggcgg gatgcggcgc  10080
gccgcgcgtt gagtggggtc cagggaaacg gggtcagctg ggggtggcag ttccaggccg  10140
cgaggccggg ctcctgggtc ggtgggctgg tgtcttggcg gacgtcccgc agctgccgcg  10200
tggatccgag ccggggcacc cgccgtgact gggacagccc ccagggcgct ctcggcccca  10260
tcccgagtag cgcggcctgg ctgctgccgc catcaagcac gttcgagcca aaagctccta  10320
acgagtcact cgttagacac gtgtgcggag cctgtgtccc aggccagtgc tgtcccgtgg  10380
agatagattg caagccgcta gggaattttt taactttcta gtaggtgtac gaaaaaagta  10440
aaacgaaaca aatcaattgg agtaaatcca taaatatatt caaactatta tttcaattgt  10500
atgtgaaaaa attattggga tattctttgt actattctta gaaatccatt gtgtgtccaa  10560
cccaaacatc acagttggac tcaccacatc tcctgtactt cgtagcccta ggtggctagt  10620
ggcataagac acaaaaatct cagctctcct ggagcttatg gtctagttgg agcaggcaga  10680
caatacattt aaaatataca gtttgttaga aggtaaatgt tgtaaacaac aataacagtt  10740
gaagtactgg ggagagttgc agttgtaaat cagatgggca gggcacaagg taacatttga  10800
gtaaagatgt aagaacttga aggagatggg caagtgagct ctataagtat acgggagagg  10860
ggcaagcaag agttcagagg ccccttgctg tggggaggga tccaaggtgg aggagtggga  10920
accaggaggg gagaggacca gtggagcaga tctcataggc agttgtaagg acttggggcc  10980
ttattcaatg aaatgaggac actttggaga gttttgaaca gagcagtgac tgatttatgt  11040
tttggttttg gtttagttct attattattt aataataggc ttattatttc acagaagttt  11100
```

-continued

```
tatttaataa ggcagacctc ttgtctggaa atgagacagg tgccggagag ctggatggag  11160
gcagatcggg aattccattt ggggcaaact gaacttgatt gagaccctgg tagttgtcca  11220
gatggaacag gacacctgag tctagggttc gggaagaact ccagatggga caaacactcc  11280
tagctttcct tttctctttt tggatgaccg ctacagggtg agacatcggt atccaggcac  11340
gataaatttc caagtggaca caatgtctgg tgtcaactac agctgttctc cttcttttcc  11400
cagtatcctt tgggtgcagt gagacaccag gagagctgct gctttggggg atggacaggg  11460
gcagcaggaa tgcctttgtg ttttcgcagt gaacctcctt ggcctgggcg aagctgtgtg  11520
gaccaagcaa gtcaggagtg tggccatgtt ttctgagcag gctgcccaga gggcccacac  11580
tctactgtcc ccaccatcag ccaacaatgc cacctttgcc cgggtgccag tggcaaccta  11640
caccaactcc tcacaaccct tccggctagg agagcgcagc tttagccggc agtatgccca  11700
catttatgcc acccgcctca tccaaatgag acccttcctg gagaaccggg cccagcagca  11760
ctggggtaag tgagagtttg ggaaggtgct tcccccacag catccctgaa cttagaagtg  11820
ttctgcaaga gaatgggaac agtttatcta attgatccca cttcctgtta ccttgggaaa  11880
attaacctct tttccctca gtttcttctt aagatagtaa caaggattaa attaagtaat  11940
ttgtgggttt ggagttagtt ttagttcaga ggctggttgg agatgaggac ttagttctgg  12000
cggtgatggc gattacttca ctggcagagg aaaatggttt tcctatcttc agtgcagatt  12060
attcaggtat ttgcctgtgc tgtagccaga gagcccctca gtgtggcaag cctggcgcca  12120
ggcaccagga gccaagactg gtgaggatgc actctctggt ctcgagggga ccccctctgt  12180
tcactcatgt ctgtttgcct ctcctcctgg cccccatatt tgctggccat gaattttcct  12240
gtcccttggg ccctctgtct ttcctaataa agtggcctgc ccaacacaac ccttgttctt  12300
tgcccccatt tcttccctgg tgatctctcc tgcagttgga ttactcttgg tggtgaagca  12360
gggaccccca tctccccctt tgagtttatt tgagttttag gtgctgctgc attcccccat  12420
tcctaccact tacataagag tggctttcca ggtaattttc aaatccatct cctattatat  12480
ttttaaactg aggatttagt aggtgagacc aggtcttact catttttact gtccttggca  12540
ccaggcaaaa tggatctcag ccctagttgc acattggaat cccctgggga gctttgagaa  12600
gcccatctca tcccatgcca agccaagatc aattctcgtt ataggcaggc aggagaaccc  12660
tgggcctaga aatctagcta gaacctcaaa ttcattaggg atatgtatta gtccattttc  12720
acattgctat aaaaaactac ctgagatagg gtaatttata aagaaaagag gtttaattga  12780
ctcacagttc ctcatggctg gggaggcctc aggaaactta acaatcatgg cagaaggtga  12840
agggaaagca aggctctttt acatgatagc aggagagaga gagcaagggg aactgccaac  12900
catttttaaa ccatcagatc gcatgatggc ttgatctcac tcaccatcac aagaacagca  12960
tgggggaaat ccaccccccac aatccagtca cctcccacca ggtccctccg tcaacaccgt  13020
gtggattata attccagatg agatgtgggt ggggacacag agccaaatca tatcaggatg  13080
ttttctgttt tgtttacctg agacaaagtg ctgttcacct ctcctctccc acataatcag  13140
gggctccctc ctgcggctcc ggtagctttt cctcactttc ctttcagccc tcgggacacc  13200
ttccttggct cctttcagag ctcagttact acttgggccc aatgtcaatg ccaccttcta  13260
gattctttcc ggcagcacct cctctggtcg cacatttctc ttccagttat tggagctgtc  13320
aaaaaagctc cccagtgatg gacgatagcg atttcactgt gctcacagac tggtcaggaa  13380
accaaacagc tgccacagtg aatgtgttga tagcagcggg gcagcagtag cactcgctca  13440
```

-continued

```
caggcctggt ggttggtgct ggcccccacc ctgaatacct acatgtggct tctccatgtg  13500
gcctgtgcat cctcactgaa gctcagcctg tctctccaaa ttggtctttc cactcacctg  13560
ttccccaaac ctgcccagac cttcctgctg taggcttttc ccttcacttg gcacactctt  13620
tcccttgtct tcccatggcc ccatctaagc cccactgtca gctgaagtgt tatattcttt  13680
gaggggccac ctgaagccac cttgcaatga gggcctccgt tttctacctc agctcaccat  13740
ttgttcacag cacttgtcac tgtggcgagt tacttgtcta tggcctgttg tcgttctcct  13800
gcctagaccc agtgggctga gtgggggcaa gtgttggctt ttatgtccag ttttgatctt  13860
ggtgccagca cattgcctgg gtggaagcat gtcctactat cggttacagg gatgtcattc  13920
tgcccagtgc tcaggggcat acacttggat cccagttgtg tgcccttgga cacattgctt  13980
aacctctctg tgcatcagtt gggtgataat atctactcct ggcacatttt cagcgttggc  14040
tgagttacat gtacagtgct taggccacct gggggagagt aagagtggga tacgtgagga  14100
tgtggagtct gttgcatttc tgtctgctgc tggcatcctt cttgtcttgt tttgagttgc  14160
tcgcctctgt ctgctcccta gggcgtagat ttgaggaata ttcctggttc ttcccaggca  14220
gcaggggctc aggctgtgct ggagtcagct aggctaaggg gctggtctgg catccgcgtt  14280
gtcctgtcac ctccttggtg ttttctccag gcctggatct gtgctgtgtg ggcacctgta  14340
ttcctccctc ctgccctcac tgattctcca tacctttctt ctcgagagtg ccaagcccct  14400
cccatgtgtt cttgttcata cctaggatcc cgggaagggg ctggggaaga cggtgcccag  14460
gtgccctggg taaacaaagc cacctgactc cacgggaatg gaatgggtgg aggggatctg  14520
aggtctgcat tttgagtatc tctggtctca gaggatgaag catttggtgg gggttggggg  14580
tggggggtag ggtggaagaa tctaaagtct taaaagaaaa tggcagttat ttgtgggaca  14640
gggctgtgtt gagacttggc atgcttcttt ttaagagtca gtgttgtaat ttaggtataa  14700
gtgaagcagt actttgtatt agtttcctgt aggcgctgta acaaagcacc acaaactggt  14760
tgacttaaaa caacagacat ggccgggcac ggtggctcac gactgtaatc ccagcacttt  14820
gggaggccga ggcgggcaga tcacaaggtc aagagattga gaccatcctg gctaacacgg  14880
tgaaaccctg tctctactaa aaatacaaaa aaaaaaaaat tagctgggcg tggtggcaca  14940
cgcctgtagt cccagctact cgggaggctg aggcaggaga atggcgtgaa cccgggaggc  15000
ggagcttgca gtgagctgag atcgcgccac tgcactccag cctggatgac agcgagactc  15060
cgcctcaaaa caaaaacaaa aacagaaaca acaataacag aaaaacacag acatttactc  15120
tctggcagtt ctggaggcca gaagttgaaa tccagatgtc agcaggattg gctccttctg  15180
aaggcccgag gggagggtcc ttcctggcct cctccctggt gttcctgggc ttgtggccgc  15240
atcactccgc tctgcccgtc ttcacactcc ctcttgtctg tgtgtctgtc tctctgttct  15300
catgaggaca cttggcatcc agggcccaac cacacccaga gtccctggtc tcctgtggct  15360
gactcacttt ttactgtcac cgtgaagtcc agggggtcct tgtacttgat gttctctcct  15420
ggcaaggcca gggccctgtg attggcctct catggagtgc tgggcagggc ctccatggcc  15480
tctgtcgggc ggggggccta cttcatctct gagtctgtac ccctcgtgtc ccaggcagtg  15540
gagtgggagt gaagaagctg tgtgaactgc agcctgagga gaagtgctgt gtggtgggca  15600
ctctgttcaa ggccatgccg ctgcagccct ccatcctgcg ggaggtcagc gaggaggtga  15660
ggcagggtgc tacacagtgg ggccgccagg cagacctggc ctcccactag aacacctccc  15720
tggaggtggg gttgtgggga agcaggttca gagacaatgg actccagagg ggtgggggct  15780
gcggtgccag ctcactaaca ccagagcttt ggtgggctct ggccccaaga ttatacctcc  15840
```

```
tgtctctgca ttccagcaca acctgctccc ccagcctcct cggagtaaat acatacaccc  15900
agatgacgag ctggtcttgg aagatgaact gcagcgtatc aaactaaaag gcaccattga  15960
cgtgtcaaag ctggttacgg gtagggagcc caatgagagg atgtgggtga tgcaggtgaa  16020
gagcccagcg gtggtgtgtt agggatggtg tgagtgggga gcctgggggg agtggggggg  16080
tgtggcctgg gcacacgtgt gttcttgagg aggtaggtga ggctccaggc ggtcggaggc  16140
catcagattg ggtgagacct ggctgggaga tgggtctccc cacctccatc caagggcagt  16200
gactccagga agcaggcatg catcctggag tcctaggtga gaattcacca atgtggttgt  16260
ggagaactgg cttgttttgc ccgttggggt gactggaagg agtggtagca cctggggctc  16320
cctgctcagg cctgatgcca ctgctcccca gggactgtcc tggctgtgtt tggctccgtg  16380
agagacgacg ggaagtttct ggtggaggac tattgctttg ctgaccttgc tccccagaag  16440
cccgcacccc cacttgacac agataggtga gcagcagttc tcgggagctg gaaccagctc  16500
atggtcagtg gaatctttga gttgcaccta ggaggggctg cctcccttct cggcaccctg  16560
gaggacccca ccttctcccg caggtttgtg ctactggtgt ccggcctggg cctgggtggc  16620
ggtggaggcg agagcctgct gggcacccag ctgctggtgg atgtggtgac ggggcagctt  16680
ggggacgaag gggagcagtg cagcgccgcc cacgtctccc gggttatcct cgctggcaac  16740
ctcctcagcc acagcaccca gagcagggat tctatcaata aggtatggag cccacctggc  16800
tgcattcagc cccagcccag gagcctgcaa gcctgtaaga ccctccttcc ccagggcgag  16860
tagggtaccc tgtgaggtct cgcaggtcgg tgggaagcgc cctgcagtga ctctggggcc  16920
tcctgcaatg gggctcctca tgcccaggcc ctcgctgagg atggtgggag gcttgaaggg  16980
agtgagggtc tatgggacaa caactgcatc ttccagctgg tggggctcta ctctcctctg  17040
agcctgggac tcgcctgggc ctgatggcct tctgggcttc tattccaggc caaatacctc  17100
accaagaaaa cccaggcagc cagcgtggag gctgttaaga tgctggatga gatcctcctg  17160
cagctgagcg tgagcgagct gggggctgga ggggtgatgg ggattgcagt cttcaaagct  17220
gccactgggc aacagaaggc aggcaggagg gcagggggag tggccggagt tggtgtaggg  17280
ggctccttcg gggccctgtg agctctccct gccctgtgcc ttccaggcct cagtgcccgt  17340
ggacgtgatg ccaggcgagt ttgatcccac caattacacg ctcccccagc agcccctcca  17400
cccctgcatg ttcccgctgg ccactgccta ctccacgctc cagctggtca ccaacccccta  17460
ccaggccacc attgatggag tcaggtagct ggcacagcca cacttcagtc tgacccagcc  17520
ttttgcctca ggaggcacaa agaagggagg ggagggaggg cccaggaagg tggcagggct  17580
gcagaggccc acctagcatc tgttccttct ctctggggca tccccacaag agcgccagat  17640
gagctctggg ctgaccacta tgggtggcac ccaaagccaa gagtcagctg agctttgcct  17700
tgcagatttt tggggacatc aggacagaac gtgagtgaca ttttccgata cagcagcatg  17760
gaggatcact tggagatcct ggagtggacc ctgcgggtcc gtcacatcag ccccacagcc  17820
ccggacactc taggtaacag gctcagccat acagggtggg agcagagggc caggaggcct  17880
ggcaggaccc tgaagtgcac agggtccccc tgtgggtttg cacttgccag cattgctgag  17940
aactgtctga ggagaagttc agaggcttgg cacctgctct ggaagctact ctggaatctt  18000
aattctaagg ccaatggctg cccaccccaa cgggcagcaa cagcagggcc aaggtcttgt  18060
gacaatgtct ggaggtgccc ctattgtcac actgggggtc tcctactggc ctgcaatggg  18120
aggaggggct gcagccccac atcctgtgca gagtgctagt gctgaggcgg aaccctcctc  18180
```

-continued

```
agagctgccc cttctcctct aggttgttac cccttctaca aaactgaccc gttcatcttc  18240
ccagagtgcc cgcatgtcta cttttgtggc aacaccccca gctttggctc caaaatcatc  18300
cgaggtaatt tttgtcttct gggggcccag gctgatttgc tgatttgctc tcacctgggg  18360
acaaggttca cagagaagaa aacctgcatt gtggagtccc cctggccctt gtgggatgga  18420
cagctgaggt cttctgcaca gctgccattt cactgtggga gccaagctgc ctcgccagct  18480
gggcagggac tggaacggct cccagcctgt gtgcctctca aggctaatct ctggtctcct  18540
attgtcactg ccccactgtg tgccaatggg gactcctgtt tatttctggc agcttctctt  18600
tgaggcagga cttacttgga acctacagtg ggtcctatgt gacttctttg caggtcctga  18660
ggaccagaca gtgctgttgg tgactgtccc tgacttcagt gccacgcaga ccgcctgcct  18720
tgtgaacctg cgcagcctgg cctgccagcc catcagcttc tcgggcttcg gggcagagga  18780
cgatgacctg ggaggcctgg ggctgggccc ctgactcaaa aaagtggttt tgaccagaga  18840
ggcccagatg gaggctgttc attccctgca gtgtcggcat tgtaaataaa gcctggcact  18900
tgctgatgcg agccttgagc cctgggcact ctggctatgg gactcctgca ggggtgccca  18960
cagtgaccat agcccatgca cccaccagcc ggtctccct                         18999
```

<210> SEQ ID NO 8
<211> LENGTH: 16161
<212> TYPE: DNA
<213> ORGANISM: Homo sapiens

<400> SEQUENCE: 8

```
cagcagggcc aaggtcttgt gacaatgtct ggaggtgccc ctattgtcac actgggggtc     60
tcctactggc ctgcaatggg aggaggggct gcagccccac atcctgtgca gagtgctagt    120
gctgaggcgg aaccctcctc agagctgccc cttctcctcc aggttgttac cccttctaca    180
aaactgaccc gttcatcttc ccagagtgcc cgcatgtcta cttttgtggc aacaccccca    240
gctttggctc caaaatcatc cgaggtaatt tttgtcttct gggggcccag gctgatttgc    300
tgatttgctc tcacctgggg acaaggttca cagagaagaa aacctgcatt gtggagtccc    360
cctggccctt gtgggatgga cagctgaggt cttctgcaca gctgccattt cactgtggga    420
gccaagctgc ctcgccagct gggcagggac tggaacggct cccagcctgt gtgcctctca    480
aggctaatct ctggtctcct attgtcactg ccccactgtg tgccaatggg gactcctgtt    540
tatttctggc agcttctctt tgaggcagga cttacttgga acctacagtg ggtcctatgt    600
gacttctttg caggtcctga ggaccagaca gtgctgttgg tgactgtccc tgacttcagt    660
gccacgcaga ccgcctgcct tgtgaacctg cgcagcctgg cctgccagcc catcagcttc    720
tcgggcttcg gggcagagga cgatgacctg ggaggcctgg ggctgggccc ctgactcaaa    780
aaagtggttt tgaccagaga ggcccagatg gaggctgttc attccctgca gtgtcggcat    840
tgtaaataaa gcctgagcac ttgctgatgc gagccttgag ccctgggcac tctggctatg    900
ggactcctgc aggggtgccc acagtgacca tagcccatgc acccaccagc cggtctccct    960
cctccccatc cctgacacct cagaatgtga gcagtccgtg ccatgagctt gttttattgg   1020
agtgaccttg gctccctccc tctgccccta ctccaacact gcagcaaccc catctcttac   1080
gagactggca ggtggagcag gagcctctac acagcctctg gctcttaggt cccagtcatg   1140
tttgcacccc ctcaaagggg caggaccagc ccttcctttc agtgtccata ccaggggcct   1200
tccatgtgct gatgggtgat gtgactgtgg tcagcaggct tgggaagtgc tgctgctgta   1260
gcttgagttg ggctggggtc ttggtaggac gctgatctca gaagtcccca aagttcactg   1320
```

-continued

```
tgtaggtctc tactgttgtg aaggggaatg cctggccagt ggctatctcc tcctctttct   1380
cctcctcctc ctcttcctca aactcgggtt ccagctgggt ctcgaactca ggctccaact   1440
gggtctcaaa ctcgggctcc accttggtcc caaactcggg ctccacctcg gtcccaaact   1500
ctgtcaccac ctctgtgtag gtctcagtct ccgactcctc ccagccagcg gtggttggcg   1560
gtatgaggcc ccagggctct atggtagtgc tcagggtggt ggcaggggca gggggcagcg   1620
tgggaggcac agtgtggggg cctagggtgg tggtggcgtt gaggcgccgc agccgcatct   1680
gtgcccgaag ccgcaggcgg tgttgtaggc gtcgctgctg caggcgtcgc tgttgggggg   1740
tcatagggcg cgatgggtct atgtgtggga taggccggtt cccgttcatg gccatgatct   1800
cccggatgcg cttccagttg gagcgagcca ggatgaagtt gcactgagtg gccccgatgt   1860
catagtcaac attgcaggtc ttggcgctcg gggtgtagcc ctccgcgtgg gctgtcacgc   1920
ggtactcacc cgggttcaag attcgccagt aatcaccacc actggctgcg gagggagaac   1980
gatccggctg ccccagagcg cccctcccag gcccccaccc tcccactcag tcctgccccc   2040
agccccgccc tccccctctg agttcccgcc cccagcaccg ccctccctct ctgaatttcg   2100
cccccaggct ccccagactc tacctgctcg ctgagttcct caagccccca ccctctctgg   2160
cgggtcctcc ctcagaaaga tggggtaaag gtgtgcacac taggtacctg tcttcacgcc   2220
gtgattaatg ccactcacag agatggtggc gttggcaatg gggatgcctt gctcgtccgt   2280
caccaccccc ttaatgccgc ggtgcaccta gggaagcagg tgagggctgc tggtcctcag   2340
gaaggtccaa tgtggtccgc tgctccctcc cgcccatcca ggagcctgtg cagcctcctc   2400
tccccaggca ttgccctagc caccccacct gctccatgaa ggtgagcagc gcctccttgt   2460
tgttctccca ctcgcggggc agctcactct catgagggaa cttgtcacag cccaggtaga   2520
aggagagctc caggcagttg gtatgcaggt aactgaagtc attgatagct ggccggggac   2580
agatacagac ccaaagtcag cccctctccg gaccaggccc cgcccacagc cctcccaggg   2640
ctgactcact cccggtccgg gggttccact tggccccgtt gacgatgccc atgccgccgg   2700
tgtagtcctg ggcttggcag cctccgcggt agggctcggt caaggtgagg tgtgcggagg   2760
cgaaggagat ggcaagccac cggaagatgg cgtggtctgg agtctcctgg gcctcggaga   2820
cctcgtcctc atcctccccc cgggctgctg ccatggctgc ggccagcagc tgctcctggg   2880
taggcgtgcg ggccatatcg taggggtagg atactagccg ctcgccgccg ttcagatttg   2940
ctcccagcac gaaggggttc ttctccatcc aggcaatgat ggcccggacc tccgtggata   3000
cctggagtgg ccagcacgtg tgaggccagg gctgcagctc cggccactat ccccaaccta   3060
gcccgatcac cctccatgaa gcttcacacc agtactcgca cgatcccctg tcccccaacc   3120
cccagagcct cagcgtctgg agttcaggca ccgtcagccc cacccccaag cccagaacac   3180
caggacccca gggtccagct gctccctcct gccctttcag ccaggctgta gcctcaccgt   3240
ggcatctggc gaaaggtagc gttcagggat gggcaagtta ttgttgggga cccggtaggg   3300
gacccatttc ctctcctcag ctccccagag cacagagttg agatccggga aatcttcaaa   3360
gatgtcaaag ccctcctcag tccacagtcc cagcgcccag ttcccaaact ctgagccctg   3420
tggggagcca gcagggtagg catcggctac ccacaccccc acaaccccca gctgcctgga   3480
ccctggccag cctcaccctt caacccacca tctgcgctgc cacctcgtag ccatcagggt   3540
tcagtgaggg caccaggtgg atgcgtgtgt cctgcaccag gctgcgcaca cgtgggttcc   3600
catcgcggta ctctcggcac aggtactgca tgagcagcag caacagctct cggcccagca   3660
```

-continued

```
cctcgttgcc atggatccca gcagtgtagc ggaactcggg ctcccctgca agggcgggag   3720
cctcagtgag cactcagtct cccgaggccc agggcagctg aggaaggacc cagacccacc   3780
tcatacccga gggtctgggg gacagctggg gctcctaggg ccctgtaaga caagccagaa   3840
tccccagaga ggctccggaa caggcgggag gcagtgagct ctgcacatca gcagcagagg   3900
ccagctgctg gcccccacag accctccccc agttcatgct ccccagggtt gtctgagatc   3960
tccatggcat agatcttgag gcctcgtgag ctcttgccca ggctgtaagt gcgggtgatg   4020
gtggggcact cctcgttcac caccttcatg agctggcgca gagggggagg acgtggaatc   4080
aatcatgcaa tccgtccccc gctgaccatg ccccttccac ttccagggcc tgctctatgg   4140
cgagggacgg gcatgacccc ttcacgcagc ccccaggtac tggcctcctt cctaaggtga   4200
gggacagcca gcatccctgg aaccagtagg gactgggccc agtgacagaa gcaccaggca   4260
cacactcccg tcagccacag acaggtccca cccccagccc caggatatat gctcccaacc   4320
tggcgcatgt ccttgtagct gtggtgccgg aaatccaggt catcggtggc caccacctca   4380
ttctgtgcgt agtagctgta gacagctgca agggaggcgg ggttgtcttt agctgggtgc   4440
cggctggccc accctagcac cccacctcca ctcagagccc ctgccagccc tccacactca   4500
cgggccacag agcaccccag cacctccagg cgcatgcaca ggctgccatt ccaggtgagt   4560
gggtagatgc ggatgaaacg agccaccacc ggctctggga gctcactcag cacgggtgtg   4620
tccttgtcca cgttcccatg aaaggtctgg ggagaggcag gcctcagagc agtactgcca   4680
gcccctctga gagcccaccc ctcgcccaga caatgggagc agagccaaga gcctgggcat   4740
ggtgcccacc atttcctcat agccgttggt gtacatcacc catgtctggc tgtcattgct   4800
gaagcccacg aagaaggtgg tcacaaaatc gtcactgtgg agtggacagt ggtcagagca   4860
agggtcttcc ccctcccagg ccctcaggtg gcctgagcct ccctcttccg agccccaaga   4920
atttaagagc tagcagggtg gtgctgcacg gcccaggtgt tgagcctggg tcctatgccc   4980
gtcacatagc catgggcagg tgatctgtcc ctaaactcat gtgctatcag gacacagggg   5040
ctgactgacc aggctgagga gtggggatgg gcagggtgag tccctcactg atctttttgg   5100
ccttctttgg ctgggccaaa gaagggccca ctggaatctc cttaatggga cacagagcca   5160
tgcctatgta gccactcccc tctgccaact atccatgagc ctggccacgc actggatgct   5220
ggagtctctg ccctgggtga tgacgcctgt gaaccgggta gtcctcctgg tgtccacctc   5280
tatccactgg gtcctggcat cgtcctcggc acaccacgca ccatcatagt agtcgtcctc   5340
agtggcaccg gtctgtccag ggggcagggg aggctgagca tgggcggagg agtcccttat   5400
cccagttggg agatgggccc atcccaatgc ccacctgcat gttgagccgg ccgcgctgtg   5460
cccccaggcc gtggcgcagc atggaggagg ctcggatctg gttgtcctca atacggtgtg   5520
actccatccc aatgggggga cactctgagg acgcgtaccc cagaatggtg gctcactagc   5580
tccatccttc cctccaccaa acccagaacc aaggagccca gagcccactc ccggcacatc   5640
gggggcacag tcagagggca gctctggtca gctggtggct ccctggtgcc ctgcaccagc   5700
ccacctggaa tcgactcaaa gccaggccag gagctgtttc caatcccagc ctgtgcttcc   5760
cctccctggg cctcagctgc cccatctgga gaacgggctg accatgccca gctctcaggg   5820
gacacacgtg aaatcacagg tagagctccc ccagggcgca gccacagatg tcatccagat   5880
ggggaccgtc tgcacaatgg ccctgcaggg atacctgtga aggtacctga ggtcctcact   5940
ccccaccaag gccccaggtc ctccccctac cacgcccagc cactaggggc cctggggagc   6000
tgccaccctc ctgaagcagg ccagcctggg gtccagggct ggggcagcca agcgaggcta   6060
```

-continued

```
tcctgggctc ccggggcccc tcccttctgg gtcccaagaa tctgagtagg aaagggttcc   6120
ggggacctgg gtcctgtttg tgacattggg ccagtcactt gtcccagcac ccccatcctg   6180
tggcccccac cctcaccccc ttgtgccccc cacttactga ctttctccgt aggcgtccac   6240
tcctcctcca actcctcgcc ctttcggggc tctagggaca atgaagggag gacatggcac   6300
caagggcccg ggaggcaatc aggagtccag atgctgcccc acagggaccc aggccccaag   6360
ccccagccac acacctttgt ggtccttgcc cttctccact gcccacttgt cggtctcctc   6420
cttggggctg ctgtcctcct ttttgggttt ctctggaagg tgcaaggtag gaggggccag   6480
tcagcctggc tctgggcttt gaggaccatg tggggtggat caggcaggcc ccaggtggcc   6540
ttcagggcag gcctggtgtg ggaagtcctt ggtcccactc actcagctcc tccttctctt   6600
cgtccgtctg gcgctcagca tcgggcttct ggggcggagg aggcccaaag taatagtcca   6660
ctatggggag ggagagccag ctgaggctgc cctgaccctg ctgcggggcc tcagctcctg   6720
ggtccacagg agctcagcag gacaggaccg cgccagaggg gaggaggacg ggagatgggg   6780
gacagctgag ttgggagagg gtcttgcagg agtcaggagc agcccgagct caggggcagc   6840
tgagcaagac cctgctgaag tcaccagccc ggccttccag gagcatctgg cctggggaaa   6900
ggactcgagg cccagggcat gggaaaggcc tggagggaca actggcacct gtgcctgggg   6960
ttgcgggctg gggggtgaga tggggagaca ttggaggcac tgatggggac ctgggggcag   7020
ggaaatggcg atgcacgggc tgccacccag gaggaaaggg aacctgaggg ctccagggac   7080
gcaggggcat gagcaacagg gaggcaaaag ccctcgggct ccctgaagag agtggggcag   7140
tggccacgag ccagcgggaa gccagttaga gcacaggact gggagggctg gaacccacat   7200
gggtgacagg gcagagtgtg tgcctaggga caccccctgtg ggggtcacag ccaagcagga   7260
accagggaag cggccaagga aagaccagcc tgagggcaga ggagacaggg cagtggctgg   7320
ggtgggcacg cagggacagc agggacagcg aggtaaccac gggcacaggt ggggttgcaa   7380
ggtgggtgag ttgccccagc tggctcctga ccacacccca gccccgaccc ccacctgcct   7440
atgtccctca gactctgggg tgctgggtac tcactgtcat cgtagttggg gatcacgtaa   7500
ccatcaccat agtcaggggg cagcgggggc agcagaggct tcacaggagg ctctggggag   7560
gcggggaggt taggaggggg ccagagcgcc gtggccatgg cacctcctct cctgcccccc   7620
atcctaccaa tcctctcctc cggggctggg gccggggcct tctcctcagg gggctctggc   7680
cagacccgct cgggcctcct ccttctgctt gggggtggcc tgggttgctt ctggcgccga   7740
atgtactcaa ctgaggggga ggctggctca gagtggggcc caaggctggg atgggcccat   7800
tggcacatcc cccaggccag gggtccgacc caggtggggc tggcaggacc ctactcaaag   7860
tcctcatagt cctccctctc gatctggtca ttgtagtcca gtgtgggttg ctcggtctcc   7920
tcctccggct ctgaggggaa agcgctggta gctgcctgac aaccccaccc aggcctactc   7980
tggggaagcc ctcagtccaa ccagccaggg cagctggccc caaggccagg cggatgacgg   8040
ccactcacca ggctggtgct cctgtgcctc cacatgggtc tcctctcctg gattctgcca   8100
gttatttgag aggggcgccc ctgcaacaca ggagttccag aagcaggtgg gcgggaggcc   8160
tgctctgacc accttgggag cctcaggcca ccagccaccc atagagccca cacagagcct   8220
gtggacaccc tcctgaggcc gagctcactc caaggaggcc tgagctcctc tggccttcag   8280
catcctgctg gcatctcatg gggccagaga gctgggccca ccttctgggg aacctactgt   8340
gctgctggag gccctaccac aaagctgtcc ccagcgggag aaggcaggag ggaactccat   8400
```

-continued

```
gggctcagag cccagggaca tctgggcagg ggcctgaggg acagaggtcc cacccaaaag   8460
gctgccaagc cctctcccta cccaaaagag gctacagcac tgagggagcc caccaatcaa   8520
attgtgaaat ttatagcaaa agtgaggttc ccatccagtg gggagctgaa ggtctatagg   8580
aagcagggcc ccagaaacct gcctcccact ccctgcctcc acccgagcag gcagtcagag   8640
ccccatcacc ccagaggagc ccggcacaaa cctccctcct ggggtagctc ctcggggcca   8700
gggctggggg gtgggggcag tggccactcc agggtttctg agggagccag aatgggggc    8760
ctcttccctg acgggggctt cttggtggcc ttgggtggct tctctttggg cttcttggtg   8820
gccttgggtg gctcctcctt gggcttcttg gtggccttag gtggcttctc cttgggcttc   8880
ttggtggcct tgggtggctt ctccttcccc ttcttgggcg gcctgggggga ccccctccaag  8940
gactccttgg gcaccttggg gcctttgtct ttcttgcctt tcttcccttt gtctttggtc   9000
ttttccggag gcactgtcca agatgcagac tcgtgtcaaa tgaacagagc cagctctgtg   9060
cccccatgag gcccctctct agatgcccag aacctgggca cagggactct tgtcagttcc   9120
cagtgcggat cagcaaactg agaggttaag tcatttgccc aagtggcaaa ctgggatccg   9180
gacccagatt ttctgtctgc aagtctgggg ctgtgaccac caatctcaac ctctctaaag   9240
actgagcgta gggttcccag ttcccagggg gaggccctca tccccccacc tgccaaaacc   9300
tcaatagggg ttccttacta tccactcctc cactattctg ttctgggcac agaaggggca   9360
gagaggtgac tgagccatcc aggcctggag gagcatctgg tcatccctgc caactgccat   9420
acaaaggaag ggacatgggc ccaagacctt cccctggtct cctacggggc aagaaaagct   9480
tcaaagaaaa gggacacttg gttgagtatt gaagcccaaa gaagaggaag tggtctcctt   9540
tcgagaagta aggggtttgg aattgattgg aaggataggg agtcctgggg ggttcaggga   9600
tcacacagag gacagaaaag acaggtaggg agcttgtggc tgcacactca tttcagagtc   9660
tgggagaggg agcagggact ggttgtgagg attccccatg ggaatcctcc caggacccta   9720
agcaggagct gcaagtgctg ttgagaacct gatgagaggt ggggagcatg agggaagttt   9780
ggcagaaaca caggaaagct accaaatgca gacagccagg ggacgcaggg ctgctagagc   9840
ggtgccccag agccaggaga gcaagcctgg aaggagagcc agaggcagga ggggcacagg   9900
cagcccaggg tgtgggaagc agccaggaaa gatctagagc tggggtggca ggggaggggc   9960
tgctgacatc aggaatgttg gatggtgcct tggaatctcc tgggagacag ggatcacaag  10020
accctctgcc accttccaga gggccacgat gaaaacagct aagatttact gacaactgat  10080
tatgcaagag gccgtgggtt aaatgcttca gtgatgcatc acctcatcta atttcctgta  10140
ctaatgtagg accacccatt gctcaccacc acctgaagcc ctgtgctcac caccacctga  10200
aactctctca cctacgtgag acctcctgga gtaggagggc aaaggcagga gggagggacg  10260
acgtgaagct gtgccaccaa cagggagagt ggtcccatta gtatggcagg gggtgacaca  10320
gcacagtccc ctgtggctca agcctagtac ctgtcgcgta ctggaggaat ggggataagc  10380
gacccgtaca accacagcac caaccctaga gccaccggcc cccaaaagcg gccctgccgc  10440
ccgggtgctg gatgtgcctc cacgccagcg ctgacctcgg cctagcacag ggtccctcca  10500
ggcatctggg ctcgcgtgcg cattagtaag ccagccattc ctcccctagc agactgggga  10560
gtggccagac cctaccgaat ccccctgttc ccacctgaga tgccagcccc ccacaccccc  10620
gccctgccct gggctcttac cttctgcggc cgtccctggc cgcttccctg gcttgccccc  10680
cgcctgggct tttcggaccc gcggggtggg ctcgggaggc ggcggggcct ccacgtcgtc  10740
ctcccggggc tcaggttcta gctctgacag gaagccctcg aggaactcct cgatctcgtc  10800
```

-continued

```
gtcggtcagc accgtctgcg ggcgccctcc agggcacagg gccagcaacg ccaggaggca  10860
gctgagcagg ggcgccccgc gcacggccgc catggccgcg gcacgcgcgg ggggctccgg  10920
ggagggcgcg gggggtcagg ggctctgggt ctctgggaaa gggcggagag gggatcgaga  10980
cgggtgaggg aatccaggaa ggggcgggag agaggatggg gtgagcgagg gaatccggga  11040
aagggaggga gagtggatta gggtgggcga ggggacccgg gaaggggtgc tggggggctc  11100
cgaagccaga ggggctcagg ggtggtcggg gcgctccgag gtctggcggc taataggcgc  11160
tccggccccg cgtggcgcac tcccgcgcgg atagccgtct ccaaagcgct ggcggggccc  11220
ggggcggggg cgccggggct tccggagccg gctccccacc cccggggagg aggaggagga  11280
agagaaggag gagccgagag tggacggagg ggctgcgggg gggcgggggg cggggggcgg  11340
ggggctaggg gcggggcagg cgggcgggcg ctggcggcga gcgtcccaag cccggagact  11400
tgcgcctagg acagaggggc agggggcggg gcgactggga agacagaggg cctgagggaa  11460
ggaaaggtgg tggggagggc ctggggtgcg ggtctgaggg ggccgacatc cctcctcctt  11520
ctgccctagg cacccccctt aaggcgggac cccgagtcca ccggggctct gagccctccg  11580
cgggtgacca ggaaccctgg acggaaagcc gtggtgtcag gcctctgaga cctctctcaa  11640
ttcggagggc cacagaaagg ccaccccatc cttcccaggc tctggagcct ctgcccatgg  11700
gccctgctgc atcccagcgt caattcattc agtcatccta ccaacctctt caggtcggtg  11760
tggggccggg ccccgtgctg ggccccaggg agggacagca cagtgggaac tcactttcca  11820
gccaggaggc aggtgcaaaa ctgccctcag agtggccagc tgccccgctg gggtaggag   11880
tcccatgtaa gggcatgcca tccctcccct ccgggtccca acgtggacaa atagccattt  11940
atcaccttct tcttaccaga actcattttt taaaaagtgt ctaccatacc tccagctgcc  12000
acatggaccc agagggccca gaggacccag aaggcaggtg gattgagtgt caactgatcc  12060
caggatccat cagggatgtg caccttggtg cctggtgttt gccataaggc ttctccaggg  12120
caaatgttgg ctgccctaca acggccatca acaggcagag tggtcccatt agtatggcag  12180
ggcgtgacac agcacagtcc cccgtgactc aagcctagtc cctgtctcat actggaggaa  12240
tggggagcta aggacagagc tccgaggaca ttccccctta aaggaatgag gacacaagag  12300
aaagctcaca ggtagtccat gggccaagtg cagaggcaga cagccctaag ccacgattgt  12360
ctgcggggtt tggccccagt gaagtagtca ggtagggaag cctaggagcc cctgggatga  12420
ttgacagggc agagtttgga cctggggtca aaaggaaaga ggaaaagtgg gtcaggaagc  12480
acctgggtcc ccagagcagc cccgagtgag ttggagcagg cagcagccgg ggaggccaca  12540
gtggaggctg ctgggcctgg gatacatgcc accccctggg agcaggacca caaggaggcc  12600
ttgcctcctc tcacacctgg tcctgccaag accctgcctt tgctttctca ctgcatctcc  12660
ttgaaaaagc agtgggactg tgtcaggttc tggctctacc tcccaggcac cacatctcgg  12720
caggtagcct cagtgccgtc cacctgtgtc cctgttctcc ttgtcgttca tacaggatca  12780
tgcatgtgct gtgcctagca cacattcttg gcactcacac tgctgccttt tagctctcat  12840
catttgccct cagagatcaa cctgagctgt gcccactggg gcgctcagag cagaccctga  12900
gccccaacac ccaggctccc tgtgcacctg agcctgcctc tgcctgccac gtgcccccag  12960
gccagtcctg gtggcagcaa ggatccgcaa gctctcccct ttcctcatcc tctgcaaagc  13020
tctgaatcat ctttctcaaa acttgttctg ggaatttgct ccgttgcccc agttgagcat  13080
gtcaagcccg gcggcccaag gctggggtga agcagcgtgg cacgtcactt ccctgggaac  13140
```

-continued

```
aactcacaca tggattggat ttgggtccaa catcctctgc cagggaaaat agaagccata  13200
agaaaacaaa aaaggaacag aaggaggctt ttcttcagtc acagcgagtc accaacaaaa  13260
acatgtgcaa aagctctcat ggagagctgg gccacaagga gggccatgat gttgggggcc  13320
ctctgacacc aagggtgtgg gcaggtggat gggaggcagc tgccctccat gccaggctga  13380
tgtgcctccc tttgggtggt ggggctggga ctcccactcc acttgaagac ctgcaccaaa  13440
aagtccttta gccctgtgcc caggctctgc cacggggccg gtgaggggac ttctcccctc  13500
tgctgccaga gtgaagccag tcagggggat gggaggcttg tagccaagag cacctagtgg  13560
ctttcagggt cccttacccc tgccacttag cagggtctgc acctgcatcc aagtgttctc  13620
ctgggctaca gtggggggct ggtagacact ctggtgatcc actttcagct tcccacatgg  13680
atgtggcagg gactgctttg gcatttccct accccaaggg acagccactg cggcaggact  13740
gggctgggga gggtggggcc tgcgctgggg agggtgcccc ctgtcccttg ctgctgctgg  13800
aatgggaagg agagttgttg agagagccag aactgtccaa gggtggaagc tggcgaaact  13860
gacctgcagg gaacagggag acagggagca tggcccagtg agtaggtcct atgtagctct  13920
gaggccatca accctgccat gagggctgag accccaagag agaagttgag gttgggtcag  13980
gggcctgtta gtgccagctg aggaggggga caggccagcc tcctcccact gggacccaag  14040
ctatagctcc tgagcctcca gagctgcctg gtgcctcaac ctggtcagag gtggaaactc  14100
acctgccagc aggcccagtg tgcctgagtt ctgactgtgg ggatctgcag ggcacagaag  14160
gataagaggt catcagggcc tggggacagg caggagtggc agggtctggg aggctgggag  14220
cagaccctcc caacctgccc catggcctcc gtggcccccca ggacccccat ggcagcagct  14280
cagacacggg ttgtgcctca gaaggaagtg aagctgtgtg taccgagatg gcccagcaaa  14340
ccctttgtat gtaaacttcc gccacagccc agctgtccag caccagcatg tgtatctggg  14400
ggaggggggat aaatagaagg tctgggaggc ctgggatctg gccagcaggc tactgggatc  14460
acagatgcca gcccctccat atctccgctt gagtcctgga tctgcctcct gggaccaaag  14520
gggaaaggac caggctaggc tccttccttt ttgttcttcc ctcttggggg aggctcctag  14580
aaactccccc ttctctgccg cccaagtgcc tggatattac cagtggggtt agcctgtttg  14640
ggcccacaag atgggatggc tcccagagcc atgggacctg aggtctccca gacagtgtct  14700
agccaccctc acaactggca gaacaatttc cttggttttc aacaacttga aaaacatatg  14760
tgattttcca cagtccggtg cttctcaggc ctggctgctg agtgagcaga gttcatgctg  14820
aattccttcc actcaccaca gggcagacag caagcccagc tgtggggact cggttggggt  14880
gggggtcacc acagcaaggc gcggggagtg gggagggggg caggcttcca gcactgatga  14940
gtaattctgc tgcccgaaga tctgggaaga gggcatgtga caacttagtg caacaatctg  15000
cccagtgtta ggtcagaagg aaggagaggt cgttcaaaat ggagtctggt ggaaaaaata  15060
atgtttggcc ccacctcata cctccctcaa aattaactcc agattaatga ggtagatgtt  15120
agaagaggaa ccagggaagg actacaagaa aatatggagt ctttatttac attgtgaggt  15180
tttctttagg ttttgtttgt ttttgttttt gatatggagt ctcactctgt cacccaggct  15240
ggagtgcagt ggtgcgatcc cggctaactg caacctccgc ctcccaggtt caagagattc  15300
tcctgcctca gcctcccaag tatctgggga ttacaggcac atgccaccat gcccggcttt  15360
ttttttttt ttttttttt gtatttttag tagagatggg gtttcaccat gttgaccagg  15420
cagatctcaa actcctgacc tcaagtgatc cacccgcctc agcctcccaa agtgctgggc  15480
gcccggcatg tgtgcccagc ctatattgac attcttgatg gagaagtctc ttaaggaagg  15540
```

-continued

```
acagagaagt ttggttgcat aaaagttttt accttctgta catcaaaata tactgaaaat  15600
gaaaataaag agcaaacaaa atactgagaa agaatgcagt gcttagagag cgaacattcc  15660
tggcctcctg tagttttagg aagcagctgt ggcctcagac ccatctgctg tgaacctcta  15720
ctccatattt attgcacttt ctgtctgtga gcgtcggttt ctctcctcta taacaatagg  15780
ataataatga cactaccatg ccttgcaaaa atgctacaag ggttcactga gataaatctg  15840
gagagtcatg cctgaaaaat agtaagtcgt tgataaaggg aagctgctat taataaataa  15900
agctttttct tttttttttt tttgagatgg aatctcactc tggcgcctag gctggagtgc  15960
agtgatgcaa tcttggctca ctgcaacctc cgcctcctgt gttcaagcaa tcctcctact  16020
tcagcatcct cagtagctgg gactacaggt gcgcaccacc atgcccggct agtttttttac  16080
atttttaaag ctattaatag gccagccaca gtggctcatg cctataatcc cagcactttg  16140
ggaagctgag gcaggtggat c                                             16161
```